(12) United States Patent
Vriezen et al.

(10) Patent No.: US 9,532,520 B2
(45) Date of Patent: Jan. 3, 2017

(54) DROUGHT TOLERANT PLANTS

(75) Inventors: Willem Vriezen, BM Haelen (NL); Lisette Nitsch, KK Nijmegan (NL)

(73) Assignee: NUNHEMS B.V., Nunhem (NL)

( * ) Notice: Subject to any disclaimer, the term of this patent is extended or adjusted under 35 U.S.C. 154(b) by 507 days.

(21) Appl. No.: 13/376,926

(22) PCT Filed: Jun. 7, 2010

(86) PCT No.: PCT/EP2010/003745
§ 371 (c)(1),
(2), (4) Date: Dec. 8, 2011

(87) PCT Pub. No.: WO2010/142465
PCT Pub. Date: Dec. 16, 2010

(65) Prior Publication Data
US 2012/0084881 A1    Apr. 5, 2012

(30) Foreign Application Priority Data
Jun. 8, 2009 (EP) ................................... 09007544

(51) Int. Cl.
| *A01H 1/06* | (2006.01) |
| *A01H 3/04* | (2006.01) |
| *A01H 5/08* | (2006.01) |
| *A01H 5/00* | (2006.01) |
| *C12N 9/16* | (2006.01) |
| *C12N 15/82* | (2006.01) |

(52) U.S. Cl.
CPC *A01H 1/06* (2013.01); *A01H 3/04* (2013.01); *A01H 5/00* (2013.01); *A01H 5/08* (2013.01); *C12N 9/16* (2013.01); *C12N 15/8218* (2013.01); *C12N 15/8273* (2013.01); *C12N 15/8293* (2013.01)

(58) Field of Classification Search
None
See application file for complete search history.

(56) References Cited

U.S. PATENT DOCUMENTS

| 4,407,956 A | 10/1983 | Howell |
| 4,536,475 A | 8/1985 | Anderson |
| 4,684,611 A | 8/1987 | Schilperoort et al. |
| 5,034,322 A | 7/1991 | Rogers et al. |
| 5,164,316 A | 11/1992 | McPherson et al. |
| 5,254,799 A | 10/1993 | De Greve et al. |
| 5,447,858 A | 9/1995 | Key et al. |
| 5,591,616 A | 1/1997 | Hiei et al. |
| 5,641,876 A | 6/1997 | McElroy |
| 5,689,042 A | 11/1997 | Amasino et al. |
| 5,689,046 A | 11/1997 | Schroder et al. |
| 5,693,507 A | 12/1997 | Daniell et al. |
| 6,051,753 A | 4/2000 | Comai et al. |
| 6,063,985 A | 5/2000 | Chua et al. |
| 6,140,553 A | 10/2000 | D'Halluin |
| 6,455,760 B1 | 9/2002 | Zhao et al. |
| 6,563,026 B2 | 5/2003 | De Both et al. |
| 7,939,328 B1 | 5/2011 | Saito et al. |
| 2002/0138879 A1 | 9/2002 | Cai et al. |
| 2002/0152502 A1* | 10/2002 | da Costa e Silva et al. . 800/298 |
| 2002/0168707 A1 | 11/2002 | Graham |
| 2002/0178463 A1 | 11/2002 | Hiei et al. |
| 2015/0156978 A1* | 6/2015 | Vriezen .................... A01H 5/08 800/267 |

FOREIGN PATENT DOCUMENTS

| EP | 0067553 | 12/1982 |
| EP | 0223247 | 5/1987 |
| EP | 0120561 | 7/1987 |
| EP | 0270822 | 6/1988 |
| EP | 0116718 | 5/1990 |
| EP | 0120515 | 11/1990 |
| EP | 426641 | 5/1991 |
| EP | 309862 | 8/1992 |
| EP | 0242246 | 11/1992 |
| EP | 0140308 | 1/1993 |
| EP | 0223399 | 4/1994 |
| EP | 0270356 | 6/1994 |
| EP | 0342926 | 9/1994 |
| EP | 0240208 | 11/1994 |
| EP | 0465572 | 6/1995 |
| EP | 759085 | 9/1996 |
| EP | 1042462 | 7/1999 |
| EP | 1071762 | 9/1999 |
| EP | 983370 | 3/2000 |
| EP | 1080208 | 3/2005 |
| EP | 1068311 | 4/2011 |
| WO | WO 9209696 | 6/1982 |
| WO | WO 8402913 | 8/1984 |

(Continued)

OTHER PUBLICATIONS

Robertson. PI 636261. Germplasm Resource Information Network. 2003. pp. 1-2.*
Lim. PI 634776. Germplasm Resource Information Network. 2003. pp. 1-2.*
Rubio et al. Triple loss of function of protein phosphatases type 2C leads to partial constitutive response to endogenous abscisic acid. Plant Physiology. 2009. 150: 1345-1355.*
Ano et al. A new source of resistance to bacterial wilt of eggplants obtained from a cross: Solanum aethiopicum L x Solanum melogena L. Agronomie. 1991. 11: 555-560.*
Watanabe et al. Ethylmethanesulfonate (EMS) mutagenesis of Solanum lycopersicum cv. Micro-Tom for large-scale mutant screens. Plant Biotechnology. 2007. 24: 33-38.*
M. Koornneef et al., "The isolation and characterization of abscisic acid-insensitive mutants of Arabidopsis thaliana", Physiol Plantarum (1984) vol. 61, pp. 377-383.
Jeffrey Leung et al., "Arabidopsis ABA Response Gene ABI1: Features of a Calcium-Modulated Protein Phosphatase", Science vol. 264 (1994), pp. 1448-1452.
Knut Meyer et al., "A Protein Phosphatase 2C Involved in ABA Signal Transduction in Arabidopsis thaliana", Science vol. 264 (1994), pp. 1452-1455.

(Continued)

Primary Examiner — Shubo (Joe) Zhou
Assistant Examiner — Ashley K Buran
(74) Attorney, Agent, or Firm — Arent Fox LLP

(57) ABSTRACT

The present invention relates to the field of transgenic and non-transgenic plants with novel phenotypes. Provided are SlPP2C1 proteins and nucleic acid sequences encoding these, which are useful in conferring novel phenotypes to plants, especially drought tolerance.

20 Claims, 2 Drawing Sheets

(56) References Cited

FOREIGN PATENT DOCUMENTS

Figure 1:
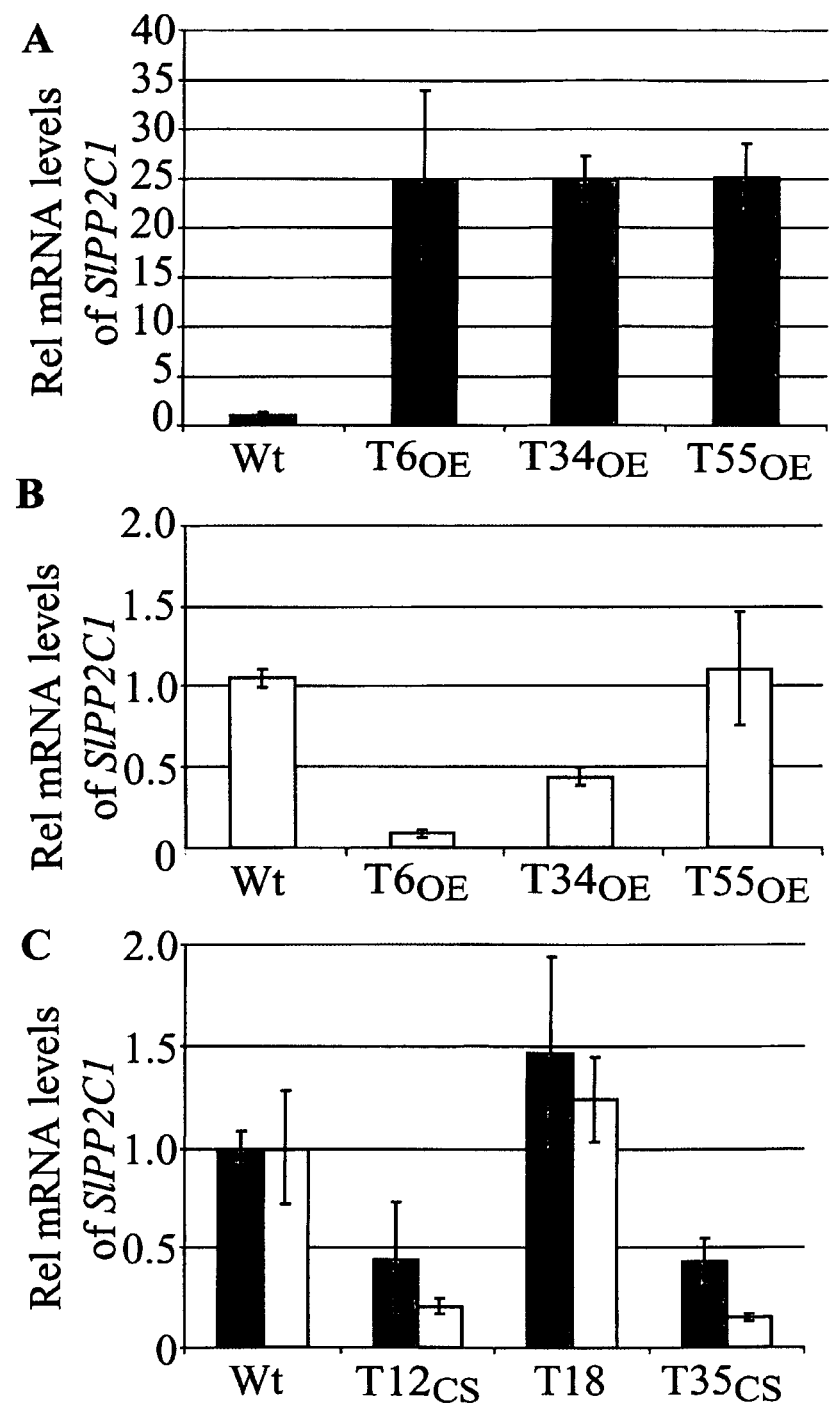

| WO | WO 8501856 | 5/1985 |
|---|---|---|
| WO | WO 9400977 | 1/1994 |
| WO | WO 9506722 | 3/1995 |
| WO | WO 9606932 | 3/1996 |
| WO | WO 9748819 | 12/1997 |
| WO | WO 0070067 | 11/2000 |
| WO | WO 0071733 | 11/2000 |
| WO | WO 2007088234 | 8/2007 |

OTHER PUBLICATIONS

Nathalie Bertauche et al., "Protein phosphatase activity of abscisic acid insensitive 1 (ABI1) protein from Arabidopsis thaliana", Eur J. Biochem vol. 241 (1996), pp. 193-200.
Jeffrey Leung et al., "The Arabidopsis ABSCISIC Acid-Insensitive2 (ABI2) and ABI1 Genes Encode Homologous Protein Phosphatases 2C involved in Abscisic Acid Signal Transduction", Plant Cell 9 (1997), pp. 759-771.
Scheen, "Mutational analysis of protein phosphatase 2C involved in abscisic acid signal transduction in higher plants", PNAS 95 (1998), pp. 975-980.
Francoise Gosti et al., "ABI1 Protein Phosphatase 2C Is a Negative Regulator of Abscisic Acid Signaling", Plant Cell 11 (1999), 1897-1909.
Sylvain Merlot et al., "The ABI1 and ABI2 protein phosphatases 2C act in a negative feedback regulatory loop of the abscisic acid signaling pathway", Plant J 25 (2001), pp. 295-303.
Danièle Moes et al., "Nuclear localization of the mutant protein phosphatase abi1 is required for insensitivity towards ABA responses in Arabidopsis", Plant J 54 (2008), pp. 806-819.
Alois Schweighofer et al., "Plant PP2C phosphatases: emerging functions in stress signaling", Trends in Plant Science vol. 9 (2004), pp. 236-243.
Pedro L. Rodriguez, "Protein phosphatase 2C (PP2C) function in higher plants", Plant Mol Biol 38 (1998), pp. 919-927.
Angela Saez et al, "Gain-of-function and loss-of-function phenotypes of the protein phosphatase 2C HAB1 reveal its role as a negative regulator of abscisic acid signalling", Plant J 37 (2004), pp. 354-369.
Josef M. Kuhn et al., "The Protein Phosphatase AtPP2CA Negatively Regulates Abscisic Acid Signal Transduction in Arabidopsis, and Effects of abh1 on AtPP2CA mRNA1[W]", Plant Physiol 140 (2006), pp. 127-139.
Tomo Yoshida et al., "ABA-Hypersensitive Germination3 Encodes a Protein Phosphatase 2C (AtPP2CA) That Strongly Regulates Abscisic Acid Signaling during Germination among Arabidopsis Protein Phosphatase 2Cs1[W] Tomo", Plant Physiology 140 (2006), pp. 115-126.
Noriyuki Nishimura et al., "ABA-Hypersensitive Germination1 encodes a protein phosphatase 2C, an essential component of abscisic acid signaling in Arabidopsis seed", Plant J 50 (2007), pp. 935-949.
Angela Saez et al., "Enhancement of Abscisic Acid Sensitivity and Reduction of Water Consumption in Arabidopsis by Combined Inactivation of the Protein Phosphatases Type 2C ABI1 and HAB11", Plant Physiol 141 (2006), pp. 1389-1399.
Henikoff & Henikoff, "Amino acid substitution matrices from protein blocks", PNAS 89 (1992), pp. 10915-10919.
Wim H. Vriezen et al., "Changes in tomato ovary transcriptome demonstrate complex hormonal regulation of fruit set", New Phytologist 177 (2008), pp. 60-76.
Liming Xiong et al., "Identification of Drought Tolerance Determinants by Genetic Analysis of Root Response to Drought Stress and Abscisic Acid1", Plant Physiology 142 (2006), pp. 1065-1074.
Hong Yu et al., "Activated Expression of an Arabidopsis HD-START Protein Confers Drought Tolerance with Improved Root System and Reduced Stomatal Density", The Plant Cell 20 (2008), pp. 1134-1151.

James J. English et al., "Suppression of Virus Accumulation in Transgenic Plants Exhibiting Silencing of Nuclear Genes", Plant Cell 8(2) (1996), pp. 179-188.
Ann Depicker et al., "Post-transcriptional gene silencing in plants", Curr Opin Cell Biol. 9(3) (1997), pp. 373-382.
Marina Byzova et al., "Transforming petals into sepaloid organs in Arabidopsis and oilseed rape: implementation of the hairpin RNA-mediated gene silencing technology in an organ-specific manner", Plant 218 (2004), pp. 379-387.
Anna Wielopolska et al., "A high-throughput inducible RNAi vector for plas", Biotechnol J. 6 (2005), pp. 583-590.
Wesley et al., "Posttranscriptional Gene Silencing in Plants", Methods Mol. Biol. 265 (2004), pp. 117-130.
Susan Varsha Wesley et al., "Custom Knock-Outs with Hairpin RNA-Mediated Gene Silencing Methods", Mol Biol. 236 (2003), pp. 273-286.
Helliwell & Waterhouse, "Constructs and methods for high-throughput gene silencing in plants", Methods 30(4) (2003), pp. 289-295.
Richard C. Gardner et al., "The complete nucleotide sequence of an infectious clone of cauliflower mosaic virus by MI3mp7 shotgun sequencing", Nucleic Acids Research 9 (1981), pp. 2871-2887.
A. Franck et al., "Nucleotide Sequence of Cauliflower Mosaic Virus DNA", Cell 21 (1980), pp. 285-294.
Rodger Hull et al., "Structure of the Cauliflower Mosaic Virus Genome", Virology 86 (1978), pp. 482-493.
Joan T. Odell et al., "Identification of DNA sequences required for activity of the cauliflower mosaic virus 35S promoter", Nature 313 (1985), pp. 810-812.
Bertrand Verdaguer et al., "Functional organization of the cassava vein mosaic virus (CsVMV) promoter", Plant Mol. Biol. 37 (1998), pp. 1055-1067.
Plan Christensen et al., "Maize polyubiquitin genes: structure, thermal perturbation of expression and transcript splicing, and promoter activity following transfer to protoplasts by electroporation", Plant Mol. Biol. 18 (1992), pp. 675-689.
Maria-Jesus Cornejo et al., "Activity of a maize ubiquitin promoter in transgenic rice", Plant Mol. Biol. 23 (1993), pp. 567-581.
De Pater, The promoter of the rice gene GOSZ is active in various different monocot tissues and binds rice nuclear factor ASF-1, Plant J. 2 (1992), pp. 834-844.
D.I. Last et al., "pEmu: an improved promoter for gene expression in cereal cells", Theor. Appl. Genet. 81 (1990), pp. 581-588.
Yong-Qiang An et al, "Strong, constitutive expression of the Arabiaopsis ACT2/ACT8 actin subclass in vegetative tissues", Plant J. 10 (1996), pp. 107-121.
Wanggen Zhang, "Analysis of Rice Act1 5' Region Activity in Transgenic Rice Plants", The Plant Cell, 3 (1991) pp. 1155-1165.
J. Velten et al., "Isolation of a dual plant promoter fragment from the Ti plasmid of Agrobacterium tumefaciens", EMBO J, 3 (1984) pp. 2723-2730.
Sharon Thoma et al., "Tissue-Specific Expression of a Gene Encoding a Cell Wall-Localized Lipid Transfer Protein from Arabidopsis", Plant Physiol., 105(1) (1994), pp. 35-45.
Mark G. M. Aarts et al., "Molecular Characterization of the CER7 Gene of Arabidopsis Involved in Epicuticular Wax Biosynthesis and Pollen Fertility", Plant Cell 7 (1995), pp. 2115-2127.
Tanya S. Hooker et al., "Significance of the Expression of the CER6 Condensing Enzyme for Cuticular Wax Production in Arabidopsis1", Plant Physiol 129 (2002), pp. 1568-1580.
Gerd Vogg et al., "Tomato fruit cuticular waxes and their effects on transpiration barrier properties: functional characterization of a mutant de® cient in a very-long-chain fatty acid b-ketoacyl-CoA synthase", J. Exp Bot. 55 (2004), pp. 1401-1410.
Jörg Stockhaus et al., "Organ-specfic and dosage-dependent expression of a leaf/stem specific gene from potato after tagging and transfer into potato and tobacco plants", Nucleic Acids Res. 15(8) (1987), pp. 3479-3491.
Jun Li et al., "DGP1, a drought-induced guard cell-specific promoter and its function analysis in tobacco plants", Sci China C Life Sci. 48(2) (2005), pp. 181-186.

(56) References Cited

OTHER PUBLICATIONS

Kazuko Yamaguchi-Shinozaki et al., "Characterization of the expression of a desiccation-responsive rd29 gene of Arabidopsis thaliana and analysis of its promoter in transgenic plants", Mol Gen Genet 236 (1993), pp. 331-340.
Takashi Aoyama et al., "A glucocorticoid-mediated transcriptional induction system in transgenic plants", Plant Journal 11 (1997), pp. 605-612.
C. Gatz et al., "Chemical Control of Gene Expression", Annu Rev Plant Physiol Plant Mol Biol. 48 (1997), pp. 89-108.
John Love et al., "Stringent control of transgene expression in Arabidopsis thaliana using the Top10 promoter system", Plant J. 21 (2000), pp. 579-588.
Tahar Ait-Ali et al., "Flexible control of plant architecture and yield via switchable expression of Arabidopsis gai", Plant Biotechnology Journal 1 (2001), pp. 337-343.
Deveaux et al., "The ethanol switch: a tool for tissue-specific gene induction during plant development". Plant J. 36, (2003), pp. 918-930.
A. Depicker et al., "Nopaline Synthase: Transcript Mapping and DNA Sequence", J. Molec. Appl. Genetics 1 (1982), pp. 561-573.
Gielen et al., "The complete nucleotide sequence of the TL-DNA of the Agrobacterium tumefaciens plasmid pTiAch5", EMBO J 3, (1984), pp. 835-846.
Velten and Schell, "Selection-expression plasmid vectors for use in genetic transformation of higher plants", Nucleic Acids Research 13, (1985), pp. 6981-6998.
Gould et al., "Transformation of Zea mays L. Using Agrobacterium tumefaciens and the Shoot Apex" Plant Physiol. 95, (1991), pp. 426-434.
Michael E. Fromm et al., "Inheritance and expression of chimeric genes in the progeny of transgenic maize plants", Bio/Technology 8, (1990), pp. 833-839.
Gordon-Kamm et al., "Transformation of Maize Cells and Regeneration of Fertile Transgenic Plants", The Plant Cell 2, (1990), pp. 603-618.
Ko Shimamoto et al., "Fertile transgenic rice plants regenerated from transformed protoplasts", Nature 338, (1989), pp. 274-276.
Swapan K. Datta et al., "Genetically Engineered Fertile Indica-Rice recovered from protoplasts", Bio/Technology 8, (1990), pp. 736-740.
Jeoung JM et al., "Optimization of sorghum transformation parameters using genes for green fluorescent protein and β-glucuronidase as visual markers", Hereditas 137 (2002), pp. 20-28.
Zuo-Yu Zhao et al., Agrobacterium-mediated sorghum transformation, Plant Mol Biol. 44, (2000), pp. 789-798.
An Gynheung et al., "Transformation of Tobacco, Tomato, Potato, and Arabidopsis thaliana Using a Binary Ti Vector System", Plant Physiol. 81, (1986), pp. 301-305.
Horsch R.B. et al., "Leaf disc transformation", Plant Molecular Biology Manual A5, Dordrecht, Netherlands, Kluwer Academic Publishers (1988), pp. 1-9.

Koornneef M. et al., "Transformation of Tomato", Nevins D.J. and R.A. Jones, eds. Tomato Biotechnology, New York, NY, USA, Alan R. Liss, Inc., (1986), pp. 169-178.
S. Sherman et al., "A rapid transformation method for Solanum tuberosum using binary Agrobacterium tumefaciens vectors", Plant Cell Rep. 7, (1988), pp. 13-16.
De Jong et al., Plant Journal 57, (2008), pp. 160-170.
Hyeon-Jin Sun et al., "A Highly Efficient Transformation Protocol for Micro-Tom, a Model Cultivar for Tomato Functional Genomics", Plant Cell Physiol. 47, (2006), pp. 426-431.
Sidorov VA et al. 1999, "Stable chloroplast transformation in potato: use of green fluorescent protein as a plastid marker", Plant J.19 (1999), pp. 209-216.
Lutz KA et al., "A novel approach to plastid transformation utilizes the phiC31 phage integrase", Plant J. 37(6) (2004), pp. 906-913.
Mc Bride et al., Amplification of a Chimeric Bacillus Gene in Chloroplasts Leads to an Extraordinary Level of an Insecticidal Protein in Tobacco, Bio/Technology 13, (1995), pp. 362-365.
David L. Smith et al., A Gene Coding for Tomato Fruit βGalactosidase II Is expressed during Fruit Ripening, Plant Physiol 117, (1998), pp. 417-423.
Xingnan Zheng et al., Overexpression of a NAC transcription factor enhances rice drought and salt tolerance Biochemical and Biophysical Research Communications 2009, 985-989.
Jaglo-Ottosen et al, Arabidopsis CBF1 Overexpression Induces COR Genes and Enhances Freezing Tolerance, Science 280, (1998), pp. 104-106.
Mie Kasuga et al, "Improving plant drought, salt, and freezing tolerance by gene transfer of a single stress-inducible transcription factor", Nat. Biotechnol. 17, (1999), pp. 287-291.
Joseph G. Dubouzet et al., "OsDREB genes in rice, Oryza sativa L., encode transcription activators that function in drought-, high-salt- and cold-responsive gene expression", Plant J. 33 (2003), pp. 751-763.
Miyazaki et al., "Tissue- and environmental response-specific expression of 10 PP2C transcripts in Mesembryanthemum crystallinum" Mol Gen Genet (1999) 261, pp. 307-316.
Xue Tongtong et al., "Genome-wide and expression analysis of protein phosphatase 2C in rice and Arabidopsis" BMC Genomics, BioMed Central, vol. 9, No. 1, 550 (2008), ISSN: 1471-2164.
Silvia Rubio et al., "Triple Loss of Function of Protein Phosphatases Type 2C Leads to partial Constitutive Response to Endogenous Abscisic Acid" Plant Physiology, (2009), vol. 150, pp. 1345-1355.
Database Geneseq [Online] Aug. 21, 2008, "Protein useful for plant improvement, SEQ ID 10219." XP002549993 retrieved from EBI accession No. GSP:ARO97176 Database accession No. ARO97176; -& WO 2006/076423 A (Monsanto Technology LLC) [US] Jul. 20, 2006.
Database EMBL [Online] Apr. 13, 2005, "Solanum lycopersicum CDNA, clone: FC05CG04, 5' end, expressed in fruit." XP002549994 retrieved from EBI accession No. EMBL:BW686303 Database accession No. BW686303.
International Search Report of PCT/EP2010/003745, mailed Sep. 22, 2010.

* cited by examiner

SEQUENCE LISTING

<160> NUMBER OF SEQ ID NOS: 22

<210> SEQ ID NO 1
<211> LENGTH: 1194
<212> TYPE: DNA
<213> ORGANISM: Solanum lycopersicum

<400> SEQUENCE: 1

```
atgattgata acgttaaagg tatgccgccg gcaaccgaga aaggttgccg gttaacggcg      60
ttgatagatt ccggtggact agcagaagta gatctgagtg agaaggagca aaattctact     120
cgacgtaggc gattggatga acgtttgttg aaatcgacga ctgagctacc ggaaaatttc     180
gatgtcttcg cagatgatta caggcattgt aagaggaaaa aaagtactgt aactgatact     240
gatgatcatc gagttcaact agcgttatct agtgaagtga aaaagtaag ggagagcttg      300 gtgacgtgct gttcacatgg atcgatatcg ttgatcggcc ggagaaggga aatggaagat     360
gcggtggcga tttatccgtg tttttcagt gaaggcggcg gcggcggcag caggaggtat      420
gattattttg gtgtttacga cgggcatgga gggtcacgtg tagcgaacgt gtgccgtgac     480
tttttgcacc gtttagtgat acagcaagtt tcggaaggag aagattacga tgggaagagt     540
attaactggg agaaagttat gacggagagt ttccgtaaaa tggacgaaaa ggtgaacaag     600 gaagggcgg agatggcgac gataggatca acggcggtgg tagcggtggt gggagtggag      660
gaatttgttg ttgcgaattg tggagattca agagctgtgc tttcacgtgc tggagttgcc     720
gtacctttgt ctattgatca taagcctgac agacctgatg agctggatag aattgaaaat     780
tcaggtggga aagtcataaa ttggaatgga caaagagtct taggagttct tgctacttca     840
agatccatag gtgatatgta cctcaaaccg tacgtgatac cagatcctga agtgatagtt     900
agcaaaagaa gcgatgaaga tgagttctta atacttgcaa gtgatggtct atgggatgtc     960
attccaaatg atgttgcgtg tgacgttaca agaagatgct tgaatggtca aacgttcaga    1020
aggtgcgatc aacaaaccaa atcctataag agagatgaag gcgtcaaaga aagtctcgca    1080
gcacgggcag cttccttcct tgcagagtta gcaattgctc ggggtagtag ggataacatc    1140
agcgtaattg tcgtcaattt gaatagatct gtacgttcat ccattgatag ttaa          1194
```

<210> SEQ ID NO 2
<211> LENGTH: 397
<212> TYPE: PRT

<213> ORGANISM: Solanum lycopersicum

<400> SEQUENCE: 2

```
Met Ile Asp Asn Val Lys Gly Met Pro Pro Ala Thr Glu Lys Gly Cys
1               5                   10                  15

Arg Leu Thr Ala Leu Ile Asp Ser Gly Gly Leu Ala Glu Val Asp Leu
            20                  25                  30

Ser Glu Lys Glu Gln Asn Ser Thr Arg Arg Arg Leu Asp Glu Arg
        35                  40                  45

Leu Leu Lys Ser Thr Thr Glu Leu Pro Glu Asn Phe Asp Val Phe Ala
    50                  55                  60

Asp Asp Tyr Arg His Cys Lys Arg Lys Ser Thr Val Thr Asp Thr
65                  70                  75                  80

Asp Asp His Arg Val Gln Leu Ala Leu Ser Ser Glu Val Lys Lys Val
                85                  90                  95

Arg Glu Ser Leu Val Thr Cys Cys Ser His Gly Ser Ile Ser Leu Ile
            100                 105                 110

Gly Arg Arg Arg Glu Met Glu Asp Ala Val Ala Ile Tyr Pro Cys Phe
        115                 120                 125

Phe Ser Glu Gly Gly Gly Gly Ser Arg Arg Tyr Asp Tyr Phe Gly
    130                 135                 140

Val Tyr Asp Gly His Gly Gly Ser Arg Val Ala Asn Val Cys Arg Asp
145                 150                 155                 160

Phe Leu His Arg Leu Val Ile Gln Gln Val Ser Glu Gly Glu Asp Tyr
                165                 170                 175

Asp Gly Lys Ser Ile Asn Trp Glu Lys Val Met Thr Glu Ser Phe Arg
            180                 185                 190

Lys Met Asp Glu Lys Val Asn Lys Glu Gly Ala Glu Met Ala Thr Ile
        195                 200                 205

Gly Ser Thr Ala Val Val Ala Val Gly Val Glu Glu Phe Val Val
    210                 215                 220

Ala Asn Cys Gly Asp Ser Arg Ala Val Leu Ser Arg Ala Gly Val Ala
225                 230                 235                 240

Val Pro Leu Ser Ile Asp His Lys Pro Asp Arg Pro Asp Glu Leu Asp
                245                 250                 255

Arg Ile Glu Asn Ser Gly Gly Lys Val Ile Asn Trp Asn Gly Gln Arg
            260                 265                 270

Val Leu Gly Val Leu Ala Thr Ser Arg Ser Ile Gly Asp Met Tyr Leu
        275                 280                 285

Lys Pro Tyr Val Ile Pro Asp Pro Glu Val Ile Val Ser Lys Arg Ser
    290                 295                 300

Asp Glu Asp Glu Phe Leu Ile Leu Ala Ser Asp Gly Leu Trp Asp Val
305                 310                 315                 320

Ile Pro Asn Asp Val Ala Cys Asp Val Thr Arg Arg Cys Leu Asn Gly
                325                 330                 335

Gln Thr Phe Arg Arg Cys Asp Gln Gln Thr Lys Ser Tyr Lys Arg Asp
            340                 345                 350

Glu Gly Val Lys Glu Ser Leu Ala Ala Arg Ala Ala Ser Phe Leu Ala
        355                 360                 365

Glu Leu Ala Ile Ala Arg Gly Ser Arg Asp Asn Ile Ser Val Ile Val
    370                 375                 380

Val Asn Leu Asn Arg Ser Val Arg Ser Ser Ile Asp Ser
385                 390                 395
```

```
<210> SEQ ID NO 3
<211> LENGTH: 19
<212> TYPE: DNA
<213> ORGANISM: Artificial Sequence
<220> FEATURE:
<223> OTHER INFORMATION: primer 1

<400> SEQUENCE: 3
tcggaaggag aagattacg                                                  19

<210> SEQ ID NO 4
<211> LENGTH: 18
<212> TYPE: DNA
<213> ORGANISM: Artificial Sequence
<220> FEATURE:
<223> OTHER INFORMATION: primer 2

<400> SEQUENCE: 4
tccacaattc gcaacaac                                                   18

<210> SEQ ID NO 5
<211> LENGTH: 21
<212> TYPE: DNA
<213> ORGANISM: Artificial Sequence
<220> FEATURE:
<223> OTHER INFORMATION: actin primer 1

<400> SEQUENCE: 5
ggactctggt gatggtgtta g                                               21

<210> SEQ ID NO 6
<211> LENGTH: 19
<212> TYPE: DNA
<213> ORGANISM: Artificial Sequence
<220> FEATURE:
<223> OTHER INFORMATION: actin primer 2

<400> SEQUENCE: 6
ccgttcagca gtagtggtg                                                  19

<210> SEQ ID NO 7
<211> LENGTH: 21
<212> TYPE: DNA
<213> ORGANISM: Artificial Sequence
<220> FEATURE:
<223> OTHER INFORMATION: ubiquitin primer 1

<400> SEQUENCE: 7
ccctggctga ttacaacatt c                                               21

<210> SEQ ID NO 8
<211> LENGTH: 20
<212> TYPE: DNA
<213> ORGANISM: Artificial Sequence
<220> FEATURE:
<223> OTHER INFORMATION: ubiquitin primer 2

<400> SEQUENCE: 8
tggtgtcagt gggttcaatg                                                 20

<210> SEQ ID NO 9
<211> LENGTH: 30
<212> TYPE: DNA
<213> ORGANISM: Artificial Sequence
<220> FEATURE:
<223> OTHER INFORMATION: S1PP2C1 primer 1
```

<400> SEQUENCE: 9
cacctgcagt caccgtcttc acattaaaat                                              30

<210> SEQ ID NO 10
<211> LENGTH: 25
<212> TYPE: DNA
<213> ORGANISM: Artificial Sequence
<220> FEATURE:
<223> OTHER INFORMATION: SlPP2C1 primer 2

<400> SEQUENCE: 10
atttgtatgg gaagcttaac tatca                                                   25

<210> SEQ ID NO 11
<211> LENGTH: 5683
<212> TYPE: DNA
<213> ORGANISM: Unknown
<220> FEATURE:
<223> OTHER INFORMATION: Solanum lycopersicon genomic SlPP2C DNA
<220> FEATURE:
<221> NAME/KEY: 5'UTR
<222> LOCATION: (2591)..(2675)
<223> OTHER INFORMATION: 5' UTR of mRNA
<220> FEATURE:
<221> NAME/KEY: exon
<222> LOCATION: (2676)..(3419)
<223> OTHER INFORMATION: exon 1 from translation start codon
<220> FEATURE:
<221> NAME/KEY: exon
<222> LOCATION: (4247)..(4352)
<223> OTHER INFORMATION: exon 2
<220> FEATURE:
<221> NAME/KEY: exon
<222> LOCATION: (4632)..(4975)
<223> OTHER INFORMATION: exon 3 up to translation stop codon
<220> FEATURE:
<221> NAME/KEY: 3'UTR
<222> LOCATION: (4976)..(5050)
<223> OTHER INFORMATION: 3' UTR of mRNA

<400> SEQUENCE: 11
gtacaaaaaa gggagacgtc gcagaggctg cagaggtccg ttgggttatt tcgttcctcc             60
acgcgctaga gagagagggg gagagtatct cgcgtgagag acgcgggaga gagggcgtgg            120
gggcaacgcg gtttctgttg gggtcgcgtg ggggagggtt tggcgtttct aggttctgtt            180
tgctgttctg gccgcgtgag ggaggaaaag agaggaggag agagtgtggg gagagacgcg            240
cgggggggag aggtcgcatg agggagaggt cgcgtgaggg tttccgtttt tgggtgattt            300
ttgttttttc tggaattggg actgttgggt cgtgcgaagg gggaagaaga gaagccgggt            360
cggtggtcgg gtcaaacgag gacggggcgg gttagatttt taagtttagt gggtcgcctg            420
ggcatatcaa atgggctggg aatttgagtt ggaacgggat tttgggcttg agggattggg            480
cctgggggtt aatgtgttgg gttgaggatt attaaataga atgggctgat ggaaggaata            540
aagggattgg gcttgagaat tgggttggtt tcgaatatac acaggatata ccggctatat            600
acacaactat gtaataccaa cgtgggtcaa aattgggtgt caacaatata tatatatata            660
tatatatgtg tgtgtgtgtg tgtgtgtgtg tgtgtgtgtg tgtaattaca acagaacaaa            720
gtgataatga taattagaca tattaaatca ttttacctca caaatcaaa atatgcaaaa             780 tatataacat ttttcattat acatccctct cctgcaaaaa tcagatcaaa taagacaaaa            840
aaaaaataat taacaaatca aaggtataaa aaatgaagaa taaggaaaat aaaaataaaa            900
tgaccatcat ggaatatctc aaagtggggt tttataggtg taatatttag gagttataat            960

-continued

```
ttttatatta aatattttga aggttatgaa tatgaaaggt taggagttag gaggtgtaat    1020
gttcattaac taatttatta atagcaatat atatatacac acataatatt attgtgtaaa    1080
aagaaataat ctaaaaaacc cttttttatta aaataaaaat atatatttttt ctcatcattg   1140 agacatgcca cataggctga ttgaagatcc tcatttatat atatattgat ttatccaaat    1200
cacttagaga tgtgttgctt agttttaaaa gggaaactaa gttgagataa ataaaagatt    1260
catatttcta gactcactta gagaagtgca ctcaatcgtc atcacttagg ttcaaatgaa    1320
ttcggtcaaa aataagctca aaattgtgac ctttaagttt aaaagagcaa gatcaaaata    1380
agctataaaa attgaattta attataatcc gtccagttct atcgaagagg ctcctttcca    1440
ataatgaatc tctccatttc ctcggattat ctatcacaga catgtcccat attgaacaat    1500
tttaaggaga ttttacgtaa atttgatgga ctcgaaagtt aattacttgt gtatattta     1560 atttgcaata ttatctatct tactaaattt taggtgtttc taaatatgct tagataagtg    1620
tatttcagat gcataggata aaatttaggt gtaactgatt ttgtatatat tatattcaag    1680
taaattcata tgtatctaga atatatagta aattaggttc gccgctcttc gatcttacgt    1740
gtcactctcc tgtgaatttg gtatcccata tacaagaaac acgtgtcctc taagtagtca    1800 atattttgt ccaccaaacg gcagaaggtt tagatagttt caccagaaac cttagcaact     1860
agaagacgcc acttgtccta tctccacatc ctactggtcc cacctaccca cgcaaaataa    1920
atgtcgatct taattaaaaa cttaaaattg tactcctcct cctttcgtta ttatttgcat    1980
aatttttatt tttaaattta aattatacaa attttaatta acatttaaga tgttttata    2040 aaaaattaca atttatagta cttttttaaat taaatatttta aattttgtt taacctttgt   2100 acattattaa tacaacgcat taataaacctt gatattattc gtatacctaa gttcaaaaga   2160
agggtaccgt accaaacaag acgttgattt tttgataatt gaataagaaa taaatttat     2220 ttgatataac ttatatatta tattaacaat ttaaaaattc gaataccgta taactaatct    2280
ttatataaat ttattcataa ttatttttta cattattaat attttacatc attttaatta    2340
agtattataa aagaaaggaa taattaataa tcacgtaaaa tattttcgcc acgtatttc     2400 ttcttccttc atccataccg cccacgtgtt tcagtcctcg tcctactcat cattggcgtt    2460
ttcatctttg gaactcaacc agccgcttca tcatcgccac gtggcataaa tcaatcatcc    2520
tatttctatc caacggttca ttttctctct acacttttgt ttaatggttc aattctctat    2580
tactttctct ctcttttttgg accgaattac gcaaaatatc ttatactact tccgttttat   2640
aatcttcgca atgcagtcac cgtcttcaca ttaaa atg att gat aac gtt aaa        2693
                                   Met Ile Asp Asn Val Lys
                                    1                5 ggt atg ccg ccg gca acc gag aaa ggt tgc cgg tta acg gcg ttg ata       2741
Gly Met Pro Pro Ala Thr Glu Lys Gly Cys Arg Leu Thr Ala Leu Ile
         10                  15                  20 gat tcc ggt gga cta gca gaa gta gat ctg agt gag aag gag caa aat       2789
Asp Ser Gly Gly Leu Ala Glu Val Asp Leu Ser Glu Lys Glu Gln Asn
         25                  30                  35 tct act cga cgt agg cga ttg gat gaa cgt ttg ttg aaa tcg acg act       2837
Ser Thr Arg Arg Arg Arg Leu Asp Glu Arg Leu Leu Lys Ser Thr Thr
 40                  45                  50 gag cta ccg gaa aat ttc gat gtc ttc gca gat gat tac agg cat tgt       2885
Glu Leu Pro Glu Asn Phe Asp Val Phe Ala Asp Asp Tyr Arg His Cys
 55                  60                  65                  70 aag agg aaa aaa agt act gta act gat act gat gat cat cga gtt caa       2933
Lys Arg Lys Lys Ser Thr Val Thr Asp Thr Asp Asp His Arg Val Gln
                 75                  80                  85
```

| | | | | | | | | | | | | | | | | |
|---|---|---|---|---|---|---|---|---|---|---|---|---|---|---|---|---|
| cta | gcg | tta | tct | agt | gaa | gtg | aaa | aaa | gta | agg | gag | agc | ttg | gtg | acg | 2981 |
| Leu | Ala | Leu | Ser | Ser | Glu | Val | Lys | Lys | Val | Arg | Glu | Ser | Leu | Val | Thr | |
| | | | 90 | | | | 95 | | | | | 100 | | | | |
| tgc | tgt | tca | cat | gga | tcg | ata | tcg | ttg | atc | ggc | cgg | aga | agg | gaa | atg | 3029 |
| Cys | Cys | Ser | His | Gly | Ser | Ile | Ser | Leu | Ile | Gly | Arg | Arg | Arg | Glu | Met | |
| | | 105 | | | | | 110 | | | | | 115 | | | | |
| gaa | gat | gcg | gtg | gcg | att | tat | ccg | tgt | ttt | ttc | agt | gaa | ggc | ggc | ggc | 3077 |
| Glu | Asp | Ala | Val | Ala | Ile | Tyr | Pro | Cys | Phe | Phe | Ser | Glu | Gly | Gly | Gly | |
| | 120 | | | | | 125 | | | | | 130 | | | | | |
| ggc | ggc | agc | agg | agg | tat | gat | tat | ttt | ggt | gtt | tac | gac | ggg | cat | gga | 3125 |
| Gly | Gly | Ser | Arg | Arg | Tyr | Asp | Tyr | Phe | Gly | Val | Tyr | Asp | Gly | His | Gly | |
| 135 | | | | 140 | | | | | 145 | | | | | 150 | | |
| ggg | tca | cgt | gta | gcg | aac | gtg | tgc | cgt | gac | ttt | ttg | cac | cgt | tta | gtg | 3173 |
| Gly | Ser | Arg | Val | Ala | Asn | Val | Cys | Arg | Asp | Phe | Leu | His | Arg | Leu | Val | |
| | | | | 155 | | | | | 160 | | | | | 165 | | |
| ata | cag | caa | gtt | tcg | gaa | gga | gaa | gat | tac | gat | ggg | aag | agt | att | aac | 3221 |
| Ile | Gln | Gln | Val | Ser | Glu | Gly | Glu | Asp | Tyr | Asp | Gly | Lys | Ser | Ile | Asn | |
| | | | 170 | | | | | 175 | | | | | 180 | | | |
| tgg | gag | aaa | gtt | atg | acg | gag | agt | ttc | cgt | aaa | atg | gac | gaa | aag | gtg | 3269 |
| Trp | Glu | Lys | Val | Met | Thr | Glu | Ser | Phe | Arg | Lys | Met | Asp | Glu | Lys | Val | |
| | | 185 | | | | | 190 | | | | | 195 | | | | |
| aac | aag | gaa | ggg | gcg | gag | atg | gcg | acg | ata | gga | tca | acg | gcg | gtg | gta | 3317 |
| Asn | Lys | Glu | Gly | Ala | Glu | Met | Ala | Thr | Ile | Gly | Ser | Thr | Ala | Val | Val | |
| | 200 | | | | | 205 | | | | | 210 | | | | | |
| gcg | gtg | gtg | gga | gtg | gag | gaa | ttt | gtt | gtt | gcg | aat | tgt | gga | gat | tca | 3365 |
| Ala | Val | Val | Gly | Val | Glu | Glu | Phe | Val | Val | Ala | Asn | Cys | Gly | Asp | Ser | |
| 215 | | | | 220 | | | | | 225 | | | | | 230 | | |
| aga | gct | gtg | ctt | tca | cgt | gct | gga | gtt | gcc | gta | cct | ttg | tct | att | gat | 3413 |
| Arg | Ala | Val | Leu | Ser | Arg | Ala | Gly | Val | Ala | Val | Pro | Leu | Ser | Ile | Asp | |
| | | | | 235 | | | | | 240 | | | | | 245 | | |

| | | |
|---|---|---|
| cat aag gtacacgttt ttaatctaaa ttgagttaag attaattcaa cttattaaaa | | 3469 |
| His Lys | | |
| tttagatttt aaaaagttat atgaaaaata ttagtagttg tcattgtttc ttatattgat | | 3529 |
| gaaaaaatat acttattaaa cctaaaattt gcagaagacg aacactttat tttttctcct | | 3589 |
| ttcgtttgca atttattagt tttactttca ttcttttatc tatgtaagaa agaatatatc | | 3649 |
| ttttttttca attctttaat tctattttttt aatatcacat attttgttat aatttatata | | 3709 |
| atattttttag tataaaatcg taagaccgaa tttatttatt ttttcatttt gtgtccagta | | 3769 |
| aaaatcaaaa cgtacacttt tctaaaagat atggctgtga ataatgtcaa aggattagcc | | 3829 |
| ctactcaaac acgaacaaag acgtgtcgtt ataattttac tttatatttt tttcgttgta | | 3889 |
| aatcctccta tataaccacg gggcctggca actttggtat gccttttatt taacactgtt | | 3949 |
| attgcagtga tcttaactcg ccgaaggtct aatgttgtat gggtcgttca acatataatt | | 4009 |
| aaactgacaa cgagtaatga tatgatcagt attcagtgat tgatgttagc ctttagcgct | | 4069 |
| gcgggtgatc aatgcttaag accatcaaat tgaaatcctg aatttgcgtg tagatatgat | | 4129 |
| agggatgaat taacttggtt ataaaaactt ctctcgacat ttgatagtgc caagtagatt | | 4189 |
| gtctttgatt tttgaaatgg aatgctttct gttgacggag ttcctgtatg ggcgcag | | 4246 |

| | | | | | | | | | | | | | | | | |
|---|---|---|---|---|---|---|---|---|---|---|---|---|---|---|---|---|
| cct | gac | aga | cct | gat | gag | ctg | gat | aga | att | gaa | aat | tca | ggt | ggg | aaa | 4294 |
| Pro | Asp | Arg | Pro | Asp | Glu | Leu | Asp | Arg | Ile | Glu | Asn | Ser | Gly | Gly | Lys | |
| | 250 | | | | | 255 | | | | | 260 | | | | | |
| gtc | ata | aat | tgg | aat | gga | caa | aga | gtc | tta | gga | gtt | ctt | gct | act | tca | 4342 |
| Val | Ile | Asn | Trp | Asn | Gly | Gln | Arg | Val | Leu | Gly | Val | Leu | Ala | Thr | Ser | |
| 265 | | | | 270 | | | | | 275 | | | | | 280 | | |

| | | |
|---|---|---|
| aga tcc ata g gtacgtcgaa gactcagctt actgcacttg taggtctttc | | 4392 |

Arg Ser Ile

| | |
|---|---|
| cctaattcat tctcatcttt gtcgaggcaa ccaacagaaa tggatatgac aaatcagatc | 4452 |
| attattgata aactagctgc tggaaattgg aatgatattg tgcaacatta ttatgtagcc | 4512 |
| cctgaccagt ccgttacaaa cctccaattg aaacattact aattatctta cttgttcgtg | 4572 |
| gcagagctga tcgtagtaaa tcatgcttct tatgatacct tattgattga tgatgccag | 4631 |

```
gt  gat atg tac ctc aaa ccg tac gtg ata cca gat cct gaa gtg ata    4678
    Gly Asp Met Tyr Leu Lys Pro Tyr Val Ile Pro Asp Pro Glu Val Ile
        285                 290                 295 gtt agc aaa aga agc gat gaa gat gag ttc tta ata ctt gca agt gat    4726
Val Ser Lys Arg Ser Asp Glu Asp Glu Phe Leu Ile Leu Ala Ser Asp
300                 305                 310                 315 ggt cta tgg gat gtc att cca aat gat gtt gcg tgt gac gtt aca aga    4774
Gly Leu Trp Asp Val Ile Pro Asn Asp Val Ala Cys Asp Val Thr Arg
                320                 325                 330 aga tgc ttg aat ggt caa acg ttc aga agg tgc gat caa caa acc aaa    4822
Arg Cys Leu Asn Gly Gln Thr Phe Arg Arg Cys Asp Gln Gln Thr Lys
            335                 340                 345 tcc tat aag aga gat gaa ggc gtc aaa gaa agt ctc gca gca cgg gca    4870
Ser Tyr Lys Arg Asp Glu Gly Val Lys Glu Ser Leu Ala Ala Arg Ala
        350                 355                 360 gct tcc ttc ctt gca gag tta gca att gct cgg ggt agt agg gat aac    4918
Ala Ser Phe Leu Ala Glu Leu Ala Ile Ala Arg Gly Ser Arg Asp Asn
    365                 370                 375 atc agc gta att gtc gtc aat ttg aat aga tct gta cgt tca tcc att    4966
Ile Ser Val Ile Val Val Asn Leu Asn Arg Ser Val Arg Ser Ser Ile
380                 385                 390                 395 gat agt taa gcttcccata caaatgaaca attttacgga tggatctttc            5015
Asp Ser
```

| | |
|---|---|
| cttttgattg tctgcagcaa taccattact gccttgcttg cttgttttct ttttcttttt | 5075 |
| ttttccattt agactgttat tggccttggt tattcacatt tgaatgattt ttaactgaca | 5135 |
| ggttagttgc tgtaatggaa gtctttgaag ttaccaacct caaccataca tttttttact | 5195 |
| aacaagattg acgaattcat aattttttg tttcgtattt gtactgtttc aacttccaga | 5255 |
| ttccttaatg agacatgata acaagcaacc tacatttaca gtttatcgta attcactgaa | 5315 |
| gttaccaagc atttatcaga aagagtaata tataggccaa tgcgtgtcat gacatagttt | 5375 |
| attcgagtct caatataaac taagagaaga gtaccataca atagatatag cagtagtgaa | 5435 |
| acctgcatat tacatgttaa tgtcttcaat gtttaatacc aaatacaaac cacatagata | 5495 |
| aatagccaca tctacattc ctgctgctat gcgtgtgaca agtgggaagg atatggttga | 5555 |
| gcttactcca gcagcaagga aaagaaatgg gtaattaatt tcatagaaaa tgcaccttct | 5615 |
| taaatcttga ctccactccc tgcggaacgt gggctatcgc ggagaccgct cacctccctc | 5675 |
| cttaaaaa | 5683 |

<210> SEQ ID NO 12
<211> LENGTH: 23
<212> TYPE: DNA
<213> ORGANISM: Artificial Sequence
<220> FEATURE:
<223> OTHER INFORMATION: Forward primer 3863

<400> SEQUENCE: 12
gtgacgtgct gttcacatgg atc                                          23

<210> SEQ ID NO 13

```
<211> LENGTH: 22
<212> TYPE: DNA
<213> ORGANISM: Artificial Sequence
<220> FEATURE:
<223> OTHER INFORMATION: Reverse primer 3861

<400> SEQUENCE: 13
tacggaaact ctccgtcata ac                                              22

<210> SEQ ID NO 14
<211> LENGTH: 1200
<212> TYPE: DNA
<213> ORGANISM: Solanum tuberosum

<400> SEQUENCE: 14
atgattgata acgttaaagg tttgccgccg gtagccgaaa aaggttgccg gttaacggcg      60
ttagtggatt ccggcggact agcagaagta gatctgagtg agaaggagcc aaatttcact     120
cgtcgtaggc gattgaatga acgtcggttg aaatcgtcgc ctgacctacc ggaaaatttc     180
aatgtcttcg ccgctgatta caggcattat aagaagaaaa aaccggaaaa cagtaccgta     240
actgatactg atgatcaagt tcaactagcg acatctagtg aagtgaaaaa agtaagggag     300
agcttggtca cgtgctgttc acatggatcg atatcgttga tcggccggag aagggaaatg     360
gaagatgcgg tggcgattta tccgagtttt ttcagtgaag gcagcagcag gaagtacgat     420
tattttggtg tttacgacgg gcatggaggg tcacgtgtag cgcacgcgtg ccgtgacttt     480
ttgcaccgtt tagtgataca gcaagtttcg gaaggagaag attatgatgg gaagagtatt     540
aattgggaga atgttatgat ggagagtttc cgtaaaatgg acgaaaaggt gaacaaggaa     600
ggggcggaga tggcgacgat aggatcaacg gccgttgtag cggtggtcgg agaggaggaa     660
tttgttgttg cgaactgtgg agattcaaga gctgtgcttt cacgtgctgg agttgcagta     720
cctttgtcta ttgatcataa gcctgacaga cctgatgagc tggatagaat tgaaaattca     780
ggtgggaaag tcataaattg gaatggacaa agagtcttag gagttcttgc tacttcaaga     840
tccataggtg atatgtacct caaaccatat gtcattccag atcctgaagt cttagttagc     900
caaagaagtg atgaagatga attcttatta cttgcaagtg atggtctatg ggatgtcatt     960
ccaaatgatg ttgcgtgtga cgttacaaga agatgcttga atggtcaaac gttcaggagg    1020
tgtgaccaac aaaccaaatc ccataagaga atgatcagt caagtgaagg tgtcaaagaa    1080
agtctcgcag cacgagcagc ttccttcctt gcagagttgg caattgctcg gggtagtagg    1140
gataacatca gtgtaattgt cgtcgatttg aatagatctg tatgttcatc cactgactga    1200

<210> SEQ ID NO 15
<211> LENGTH: 399
<212> TYPE: PRT
<213> ORGANISM: Solanum tuberosum

<400> SEQUENCE: 15

Met Ile Asp Asn Val Lys Gly Leu Pro Pro Val Ala Glu Lys Gly Cys
1               5                   10                  15

Arg Leu Thr Ala Leu Val Asp Ser Gly Gly Leu Ala Glu Val Asp Leu
            20                  25                  30

Ser Glu Lys Glu Pro Asn Phe Thr Arg Arg Arg Leu Asn Glu Arg
        35                  40                  45

Arg Leu Lys Ser Ser Pro Asp Leu Pro Glu Asn Phe Asn Val Phe Ala
    50                  55                  60

Ala Asp Tyr Arg His Tyr Lys Lys Lys Lys Pro Glu Asn Ser Thr Val
```

```
            65                  70                  75                  80
        Thr Asp Thr Asp Asp Gln Val Gln Leu Ala Thr Ser Ser Glu Val Lys
                        85                  90                  95
        Lys Val Arg Glu Ser Leu Val Thr Cys Cys Ser His Gly Ser Ile Ser
                    100                 105                 110
        Leu Ile Gly Arg Arg Glu Met Glu Asp Ala Val Ala Ile Tyr Pro
                115                 120                 125
        Ser Phe Phe Ser Glu Gly Ser Ser Arg Lys Tyr Asp Tyr Phe Gly Val
            130                 135                 140
        Tyr Asp Gly His Gly Gly Ser Arg Val Ala His Ala Cys Arg Asp Phe
        145                 150                 155                 160
        Leu His Arg Leu Val Ile Gln Gln Val Ser Glu Gly Glu Asp Tyr Asp
                        165                 170                 175
        Gly Lys Ser Ile Asn Trp Glu Asn Val Met Met Glu Ser Phe Arg Lys
                    180                 185                 190
        Met Asp Glu Lys Val Asn Lys Glu Gly Ala Glu Met Ala Thr Ile Gly
                195                 200                 205
        Ser Thr Ala Val Val Ala Val Val Gly Glu Glu Glu Phe Val Val Ala
        210                 215                 220
        Asn Cys Gly Asp Ser Arg Ala Val Leu Ser Arg Ala Gly Val Ala Val
        225                 230                 235                 240
        Pro Leu Ser Ile Asp His Lys Pro Asp Arg Pro Asp Glu Leu Asp Arg
                        245                 250                 255
        Ile Glu Asn Ser Gly Gly Lys Val Ile Asn Trp Asn Gly Gln Arg Val
                    260                 265                 270
        Leu Gly Val Leu Ala Thr Ser Arg Ser Ile Gly Asp Met Tyr Leu Lys
                275                 280                 285
        Pro Tyr Val Ile Pro Asp Pro Glu Val Leu Val Ser Gln Arg Ser Asp
            290                 295                 300
        Glu Asp Glu Phe Leu Leu Leu Ala Ser Asp Gly Leu Trp Asp Val Ile
        305                 310                 315                 320
        Pro Asn Asp Val Ala Cys Asp Val Thr Arg Arg Cys Leu Asn Gly Gln
                        325                 330                 335
        Thr Phe Arg Arg Cys Asp Gln Gln Thr Lys Ser His Lys Arg Asp Asp
                    340                 345                 350
        Gln Ser Ser Glu Gly Val Lys Glu Ser Leu Ala Ala Arg Ala Ala Ser
                355                 360                 365
        Phe Leu Ala Glu Leu Ala Ile Ala Arg Gly Ser Arg Asp Asn Ile Ser
            370                 375                 380
        Val Ile Val Val Asp Leu Asn Arg Ser Val Cys Ser Ser Thr Asp
        385                 390                 395

<210> SEQ ID NO 16
<211> LENGTH: 14
<212> TYPE: PRT
<213> ORGANISM: Solanum lycopersicum
<220> FEATURE:
<221> NAME/KEY: VARIANT
<222> LOCATION: (2)..(2)
<223> OTHER INFORMATION: Xaa may be any amino acid or Glu

<400> SEQUENCE: 16

Asp Xaa Phe Leu Ile Leu Ala Ser Asp Gly Leu Trp Asp Val
1               5                   10

<210> SEQ ID NO 17
```

```
<211> LENGTH: 7
<212> TYPE: PRT
<213> ORGANISM: Solanum lycopersicum
<220> FEATURE:
<221> NAME/KEY: VARIANT
<222> LOCATION: (3)..(3)
<223> OTHER INFORMATION: Xaa may be any amino acid or Tyr

<400> SEQUENCE: 17

Gly Val Xaa Asp Gly His Gly
1               5

<210> SEQ ID NO 18
<211> LENGTH: 7
<212> TYPE: PRT
<213> ORGANISM: Solanum lycopersicum
<220> FEATURE:
<221> NAME/KEY: misc_feature
<222> LOCATION: (3)..(3)
<223> OTHER INFORMATION: Xaa can be any naturally occurring amino acid

<400> SEQUENCE: 18

Asp Val Xaa Asp Gly His Gly
1               5

<210> SEQ ID NO 19
<211> LENGTH: 7
<212> TYPE: PRT
<213> ORGANISM: Solanum lycopersicum
<220> FEATURE:
<221> NAME/KEY: misc_feature
<222> LOCATION: (3)..(3)
<223> OTHER INFORMATION: Xaa can be any naturally occurring amino acid

<400> SEQUENCE: 19

Gly Val Xaa Asp Gly His Asp
1               5

<210> SEQ ID NO 20
<211> LENGTH: 7
<212> TYPE: PRT
<213> ORGANISM: Solanum lycopersicum
<220> FEATURE:
<221> NAME/KEY: misc_feature
<222> LOCATION: (3)..(3)
<223> OTHER INFORMATION: Xaa can be any naturally occurring amino acid

<400> SEQUENCE: 20

Asp Val Xaa Asp Gly His Asp
1               5

<210> SEQ ID NO 21
<211> LENGTH: 7
<212> TYPE: PRT
<213> ORGANISM: Solanum lycopersicum
<220> FEATURE:
<221> NAME/KEY: misc_feature
<222> LOCATION: (3)..(3)
<223> OTHER INFORMATION: Xaa can be any naturally occurring amino acid

<400> SEQUENCE: 21

Gly Val Xaa Asp Asp His Gly
1               5

<210> SEQ ID NO 22
<211> LENGTH: 174
<212> TYPE: DNA
<213> ORGANISM: Artificial Sequence
<220> FEATURE:
```

-continued

```
<223> OTHER INFORMATION: SlPP2C1 transcript (174 bp)

<400> SEQUENCE: 22
tcggaaggag aagattacga tgggaagagt attaactggg agaaagttat gacggagagt       60
ttccgtaaaa tggacgaaaa ggtgaacaag gaaggggcgg agatggcgac gataggatca      120
acggcggtgg tagcggtggt gggagtggag gaatttgttg ttgcgaattg tgga            174
```

DROUGHT TOLERANT PLANTS

This application is a U.S. National Stage of International Application PCT/EP2010/003745, filed Jun. 7, 2010, which claims priority to EP 09007544.1, filed Jun. 8, 2009, the contents of each are hereby incorporated by reference in their entirety.

FIELD OF THE INVENTION

The present invention relates to the field of plant biotechnology and plant breeding. Provided are drought tolerant plants, especially drought tolerant vegetable species such as tomato (*Solanum lycopersicum*), and methods for making genetically modified or mutant drought tolerant plants. The invention provides a novel gene, referred to as SlPP2C1, encoding the SlPP2C protein which is a negative regulator of abscisic acid (ABA) response. Down-regulation, knockout or silencing of the SlPP2C1 gene results in plants having significantly increased drought tolerant. Provided are also plants, seeds, fruit and plant parts, comprising a mutant SlPP2C1 allele in their genome and having significantly increased drought tolerance. In another embodiment methods for making drought tolerant plants comprising one or more mutant SlPP2C1 alleles in their genome are provided herein.

BACKGROUND OF THE INVENTION

The phytohormone abscisic acid (ABA) is important for the regulation of abiotic stress responses (such as drought, salinity, cold shock, wounding, pathogen attack) and seed development and dormancy. Screens for mutants with altered abiotic stress responses or seed dormancy have been used frequently and resulted in the identification of genes important for ABA biosynthesis and ABA signal transduction. Via such a screen the *Arabidopsis* ABA-insensitive mutants abi1-1 and abi2-1 have been identified (Koornneef et al. 1984, Physiol Plantarum 61: 377-383).

Cloning and characterization of the AtABI1 gene revealed that it encodes for a serine/threonine protein phosphatase type 2C (PP2C, Leung et al. 1994, Science 264: 1448-1452; Meyer et al. 1994, Science 264: 1452-1455). AtABI2 also encodes for a protein phosphatase type 2C. abi1-1 and abi2-1 mutants carry mutations in the AtABI1 and AtABI2 genes, which result in identical Gly-to-Asp substitutions at equivalent positions (Leung et al. 1997, Plant Cell 9: 759-771). Both mutants were shown to have reduced phosphatase activity (Bertauche et al. 1996, Eur J Biochem 241: 193-200; Leung et al. 1997, supra), which would suggest that AtABI1 and AtABI2 are positive regulators of ABA sensitivity. However, constitutive over-expression of AtABI1 inhibited ABA action in maize protoplast, and reduction-of-function mutants of AtABI1 and AtABI2 were shown to have hypersensitive responses to ABA (Scheen 1998, PNAS 95:975-980; Gosti et al. 1999, Plant Cell 11: 1897-1909; Merlot et al. 2001, Plant J 25:295-303). Altogether, it was therefore concluded that AtABI1 and AtABI2 are negative regulators of the ABA response. The exact mechanism by which the mutations in abi1-1 and abi2-1 induce ABA insensitivity is still unknown, although it might be related to the preferential nuclear localization of the mutated proteins (Moes et al. 2008, Plant J 54: 806-819). AtABI1 and AtABI2 are important for seed dormancy but also for seedling growth and regulation of stomatal aperture, suggesting that these proteins act before major branch points that control tissue-specific ABA signaling cascades (Leung et al. 1997, supra).

Seventy-six PP2Cs have been identified in *Arabidopsis*, of which one subgroup subgroup PP2C-A), consisting of nine genes, has been associated with ABA signal transduction (Schweighofer et al. 2004, Trends in Plant Science Vol 9: 236-243). Several of the *Arabidopsis* genes belonging to this group were also found to encode for negative regulators of the ABA response. For example AtP2C-HA (Rodriguez et al. 1998, Plant Mol Biol 38: 879-883)(also named AtHAB1, Saez et al. 2004, Plant J 37: 354-369) is a repressor of the ABA signalling pathway that regulates numerous ABA responses such as stomatal closure, seed germination and inhibition of vegetative growth. Also HAB2 seems to have a similar regulatory role. AtPP2CA (Kuhn et al. 2006, Plant Physiol 140:127-139) has also been described as being a negative regulator of ABA, with the mutant showing ABA hypersensitivity. Interestingly, the gene disruption mutant showed an ABA hypersensitive stomatal closure response, while transpiration (water loss) of the mutant was no different than in wild type plants. Also Yoshida et al. (2006, Plant Physiology 140: 115-126) studied a missense loss-of-function mutation in AtPP2CA, which had $\frac{1}{100}^{th}$ protein phosphatase activity of the wild type, and whereby the mutant *Arabidopsis* plants showed ABA hypersensitivity during seed germination, but mutant plants did not show any change in drought tolerance compared to wild type (page 124, LH Column, last paragraph).

ABI1 and ABI2 are repressors of ABA signalling pathways that regulate many ABA responses, such as stomatal closure, osmotic water permeability of plasma membranes, drought-induced resistance and rhizogenesis, response to glucose, high light stress, seed germination and inhibition of vegetative growth. AHG1 (At5g51760) is a negative regulator of ABA during seed germination (Nishimura et al. 2007, Plant J 50: 935-949) and AHG3 (At3g11410) is a negative regulator of ABA during seed germination and cold acclimation. Three other, At5g9220, At2g29380 and At1g07430, may after all not be involved in ABA signalling as null mutations did not reveal any change in sensitivity to ABA (Yoshida et al, 2006: Plant Physiology 140:115-126).

ABA biosynthesis and signalling is, thus, extremely complex, and although various genes have been identified in *Arabidopsis* which appear to be involved (group PP2C-A), their role in ABA dependent responses, such as abiotic stress, seed dormancy and seedling growth is to a large extent unclear. In addition, protein sequences show little conservation and amino acid sequences share little sequence identity. The genes are grouped together phylogenetically, based on protein domains (or motifs) such as the catalytic domain (protein serine/threonine phosphatase like domain) which is typically located at the C-terminal of the proteins. The N-terminal varies considerably and may play a role in substrate binding or provide specific attachment sites to signalling complexes. In addition to the in vivo function being unclear, also little is known about the subcellular localization, substrates and specificity of the enzymes or how these monomeric enzymes are regulated in vivo.

WO2007/088234 describes that combined inactivation of ABI1 and HAB1 strengthens the response to ABA leads to *Arabidopsis* plants which are resistant to salinity and hydric stress. Tomato orthologs of ABI1 (SGN-U231558) and HAB1 (SGN-U217609) are presented in FIGS. 6 and 7. See also Saez et al. 2006, Plant Physiol 141:1389-1399.

Although abi1 hab1 double mutants lead to drought tolerance in *Arabidopsis thaliana*, there remains a need for providing genes which are suitable for generating drought tolerance in crop plants, especially in field crops (e.g. rice, maize, soybean, wheat, barley, rye, *sorghum, Brassica*, etc.) and vegetable crops (e.g. tomato, cucumber, onion, carrot, cabbage, cauliflower, broccoli, watermelon, melon, lettuce, leek, spinach, radish, potato, artichoke, corn salad, pumpkin, squash, bean, peas, pepper, etc.). Especially in vegetable crops water shortage can be a big problem, as roots of many crops are shallow and as products are often sold fresh and water shortage can lead to reduced vegetable quality and reduced yield. Fruit and seed vegetables, such as tomatoes, are sensitive to water shortage during flowering and during fruit- and seed development. Fruit-set can be seriously reduced by water shortage during fruit development. Common practice to deal with potential water stress situations is to irrigate crops and/or to plant cultivars or varieties with drought tolerance, in as far as these are available. Also mulches and row covers may be used.

Despite breeding efforts, tomato plants remain sensitive to drought and no commercial cultivar with drought tolerance is available.

The present invention provides new genes, referred to as SlPP2C1, suitable for generating drought tolerant crop plants, especially tomato plants and other vegetable plants. The present invention also provides methods of generating drought tolerant plants. Also provided are the drought tolerant plants, seeds and plant parts (harvested fruit, etc.) themselves.

GENERAL DEFINITIONS

The term "nucleic acid sequence" (or nucleic acid molecule) refers to a DNA or RNA molecule in single or double stranded form, particularly a DNA encoding a protein or protein fragment according to the invention. An "isolated nucleic acid sequence" refers to a nucleic acid sequence which is no longer in the natural environment from which it was isolated, e.g. the nucleic acid sequence in a bacterial host cell or in the plant nuclear or plastid genome.

The terms "protein" or "polypeptide" are used interchangeably and refer to molecules consisting of a chain of amino acids, without reference to a specific mode of action, size, 3 dimensional structure or origin. A "fragment" or "portion" of a SlPP2C1 protein may thus still be referred to as a "protein". An "isolated protein" is used to refer to a protein which is no longer in its natural environment, for example in vitro or in a recombinant bacterial or plant host cell.

The term "gene" means a DNA sequence comprising a region (transcribed region), which is transcribed into an RNA molecule (e.g. an mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites.

A "chimeric gene" (or recombinant gene) refers to any gene, which is not normally found in nature in a species, in particular a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense (reverse complement of the sense strand) or inverted repeat sequence (sense and antisense, whereby the RNA transcript forms double stranded RNA upon transcription). A "cis-gene" is a chimeric gene wherein preferably all of the gene sequences, but at least the transcribed sequence, are/is from a plant species which is sexually compatible with the species into which the gene is introduced.

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi). The coding sequence may be in sense-orientation and encodes a desired, biologically active protein or peptide, or an active peptide fragment. In gene silencing approaches, the DNA sequence is preferably present in the form of an antisense DNA or an inverted repeat DNA, comprising a short sequence of the target gene in antisense or in sense and antisense orientation (inverted repeat). "Ectopic expression" refers to expression in a tissue in which the gene is normally not expressed.

An "active protein" or "functional protein" is a protein which has protein activity as measurable in vitro, e.g. by an in vitro activity assay, and/or in vivo, e.g. by the phenotype conferred by the protein. A "wild type" protein is a fully functional protein, as present in the wild type plant. A "mutant protein" is herein a protein comprising one or more mutations in the nucleic acid sequence encoding the protein, whereby the mutation results in (the mutant nucleic acid molecule encoding) a "reduced-function" or "loss-of-function" protein, as e.g. measurable by the protein activity in vitro compared to the activity of the wild type protein, e.g. by an activity assay, and/or in vivo, e.g. by the phenotype conferred by the mutant allele.

A "mutation" in a nucleic acid molecule coding for a protein is a change of one or more nucleotides compared to the wild type sequence, e.g. by replacement, deletion or insertion of one or more nucleotides. A "point mutation" is the replacement of a single nucleotide, or the insertion or deletion of a single nucleotide.

A "non-sense" mutation is a (point) mutation in a nucleic acid sequence encoding a protein, whereby a codon is changed into a stop codon. This results in a premature stop codon being present in the mRNA and in a truncated protein. A truncated protein may have reduced function or loss of function.

A "mis-sense" mutation is a (point) mutation in a nucleic acid sequence encoding a protein, whereby a codon is changed to code for a different amino acid. The resulting protein may have reduced function or loss of function.

A "splice-site" mutation is a mutation in a nucleic acid sequence encoding a protein, whereby RNA splicing of the pre-mRNA is changed, resulting in an mRNA having a different nucleotide sequence and a protein having a different amino acid sequence than the wild type. The resulting protein may have reduced function or loss of function.

A "frame-shift" mutation is a mutation a nucleic acid sequence encoding a protein by which the reading frame of the mRNA is changed, resulting in a different amino acid sequence. The resulting protein may have reduced function or loss of function.

A mutation in a regulatory sequence, e.g. in a promoter of a gene, is a change of one or more nucleotides compared to the wild type sequence, e.g. by replacement, deletion or insertion of one or more nucleotides, leading for example to reduced or no mRNA transcript of the gene being made.

"Silencing" refers to a down-regulation or completely inhibition of gene expression of the target gene or gene family.

A "target gene" in gene silencing approaches is the gene or gene family (or one or more specific alleles of the gene) of which the endogenous gene expression is down-regulated or completely inhibited (silenced) when a chimeric silencing gene (or 'chimeric RNAi gene') is expressed and for example produces a silencing RNA transcript (e.g. a dsRNA or hairpinRNA capable of silencing the endogenous target gene expression). In mutagenesis approaches, a target gene is the endogenous gene which is to be mutated, leading to a change in (reduction or loss of) gene expression or a change in (reduction or loss of) function of the encoded protein.

A "sense" RNA transcript is generally made by operably linking a promoter to a double stranded DNA molecule wherein the sense strand (coding strand) of the DNA molecule is in 5' to 3' orientation, such that upon transcription a sense RNA is transcribed, which has the identical nucleotide sequence to the sense DNA strand (except that T is replaced by U in the RNA). An "antisense" RNA transcript is generally made by operably linking a promoter to the complementary strand (antisense strand) of the sense DNA, such that upon transcription an antisense RNA is transcribed.

A "transcription regulatory sequence" is herein defined as a nucleic acid sequence that is capable of regulating the rate of transcription of a (coding) sequence operably linked to the transcription regulatory sequence. A transcription regulatory sequence as herein defined will thus comprise all of the sequence elements necessary for initiation of transcription (promoter elements), for maintaining and for regulating transcription, including e.g. attenuators or enhancers. Although mostly the upstream (5') transcription regulatory sequences of a coding sequence are referred to, regulatory sequences found downstream (3') of a coding sequence are also encompassed by this definition.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary to join two protein encoding regions, contiguous and in reading frame so as to produce a "chimeric protein". A "chimeric protein" or "hybrid protein" is a protein composed of various protein "domains" (or motifs) which is not found as such in nature but which a joined to form a functional protein, which displays the functionality of the joined domains. A chimeric protein may also be a fusion protein of two or more proteins occurring in nature.

The term "domain" as used herein means any part(s) or domain(s) of the protein with a specific structure or function that can be transferred to another protein for providing a new hybrid protein with at least the functional characteristic of the domain. Specific domains can also be used to identify protein members belonging to the SlPP2C1 group of proteins, such as SlPP2C1 orthologs from other plant species. Examples of domains found in SlPP2C1 proteins are the serine/threonine phosphatase 2C (PP2C or PP2C-like) catalytic domain comprises within about amino acid 84-391 of SEQ ID NO: 2 or the N-terminal region of the SlPP2C protein (amino acid 1-83 of SEQ ID No: 2).

The terms "target peptide" refers to amino acid sequences which target a protein to intracellular organelles such as plastids, preferably chloroplasts, mitochondria, or to the extracellular space (secretion signal peptide). A nucleic acid sequence encoding a target peptide may be fused (in frame) to the nucleic acid sequence encoding the amino terminal end (N-terminal end) of the protein.

A "nucleic acid construct" or "vector" is herein understood to mean a man-made nucleic acid molecule resulting from the use of recombinant DNA technology and which is used to deliver exogenous DNA into a host cell. The vector backbone may for example be a binary or superbinary vector (see e.g. U.S. Pat. No. 5,591,616, US2002138879 and WO9506722), a co-integrate vector or a T-DNA vector, as known in the art and as described elsewhere herein, into which a chimeric gene is integrated or, if a suitable transcription regulatory sequence is already present, only a desired nucleic acid sequence (e.g. a coding sequence, an antisense or an inverted repeat sequence) is integrated downstream of the transcription regulatory sequence. Vectors usually comprise further genetic elements to facilitate their use in molecular cloning, such as e.g. selectable markers, multiple cloning sites and the like (see below).

A "host cell" or a "recombinant host cell" or "transformed cell" are terms referring to a new individual cell (or organism) arising as a result of at least one nucleic acid molecule, especially comprising a chimeric gene encoding a desired protein or a nucleic acid sequence which upon transcription yields an antisense RNA or an inverted repeat RNA (or hairpin RNA) for silencing of a target gene/gene family, having been introduced into said cell. The host cell is preferably a plant cell or a bacterial cell. The host cell may contain the nucleic acid construct as an extra-chromosomally (episomal) replicating molecule, or more preferably, comprises the chimeric gene integrated in the nuclear or plastid genome of the host cell.

The term "selectable marker" is a term familiar to one of ordinary skill in the art and is used herein to describe any genetic entity which, when expressed, can be used to select for a cell or cells containing the selectable marker. Selectable marker gene products confer for example antibiotic resistance, or more preferably, herbicide resistance or another selectable trait such as a phenotypic trait (e.g. a change in pigmentation) or a nutritional requirements. The term "reporter" is mainly used to refer to visible markers, such as green fluorescent protein (GFP), eGFP, luciferase, GUS and the like.

The term "ortholog" of a gene or protein refers herein to the homologous gene or protein found in another species, which has the same function as the gene or protein, but (usually) diverged in sequence from the time point on when the species harbouring the genes diverged (i.e. the genes evolved from a common ancestor by speciation). Orthologs of the tomato SlPP2C1 gene may thus be identified in other plant species based on both sequence comparisons (e.g. based on percentages sequence identity over the entire sequence and/or over specific domains) and/or functional analysis. The terms "homologous" and "heterologous" refer to the relationship between a nucleic acid or amino acid sequence and its host cell or organism, especially in the context of transgenic organisms. A homologous sequence is thus naturally found in the host species (e.g. a tomato plant transformed with a tomato gene), while a heterologous sequence is not naturally found in the host cell (e.g. a tomato plant transformed with a sequence from potato plants). Depending on the context, the term "homolog" or "homologous" may alternatively refer to sequences which are descendent from a common ancestral sequence (e.g. they may be orthologs).

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

"Sequence identity" and "sequence similarity" can be determined by alignment of two peptide or two nucleotide sequences using global or local alignment algorithms. Sequences may then be referred to as "substantially identical" or "essentially similar" when they (when optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimises the number of gaps. Generally, the default parameters are used, with a gap creation penalty=10 and gap extension penalty=0.5 (both for nucleotide and protein alignments). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may for example be determined using computer programs, such as the GCG Wisconsin Package, Version 10.3, available from Accelrys Inc., 9685 Scranton Road, San Diego, Calif. 92121-3752 USA or EMBOSS (http://www.ebi.ac.uk/Tools/webservices/services/emboss). Alternatively percent similarity or identity may be determined by searching against databases such as FASTA, BLAST, etc., but hits should be retrieved and aligned pairwise to compare sequence identity.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". It is further understood that, when referring to "sequences" herein, generally the actual physical molecules with a certain sequence of subunits (e.g. amino acids) are referred to.

As used herein, the term "plant" includes the whole plant or any parts or derivatives thereof, such as plant organs (e.g., harvested or non-harvested storage organs, bulbs, tubers, fruits, leaves, etc.), plant cells, plant protoplasts, plant cell tissue cultures from which whole plants can be regenerated, plant calli, plant cell clumps, and plant cells that are intact in plants, or parts of plants, such as embryos, pollen, ovules, fruits (e.g., harvested tissues or organs, such as harvested tomatoes, etc.), tubers (e.g. potatoes) flowers, leaves, seeds, tubers, bulbs, clonally propagated plants, roots, root-stocks, stems, root tips and the like. Also any developmental stage is included, such as seedlings, immature and mature, etc.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of 1 locus or gene (or a series of phenotypical characteristics due to this single locus or gene), but which can otherwise differ from one another enormously as regards the other loci or genes.

"F1, F2, etc." refers to the consecutive related generations following a cross between two parent plants or parent lines. The plants grown from the seeds produced by crossing two plants or lines is called the F1 generation. Selfing the F1 plants results in the F2 generation, etc. "F1 hybrid" plant (or F1 seed) is the generation obtained from crossing two inbred parent lines. An "M1 population" is a plurality of mutagenized seeds/plants of a certain plant line or cultivar. "M1, M2, M3, M4, etc." refers to the consecutive generations obtained following selfing of a first mutagenized seed/plant (M1).

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "locus" (loci plural) means a specific place or places or a site on a chromosome where for example a gene or genetic marker is found. The SlPP2C1 locus is thus the location in the genome where the SlPP2C1 gene is found.

"Wild type allele" (WT) refers herein to a version of a gene encoding a functional protein (wild type protein). The wild type SlPP2C1 allele is, for example, depicted in SEQ ID NO: 1. "Mutant allele" refers herein to an allele comprising one or more mutations in the coding sequence (mRNA or cDNA) or genomic sequence compared to the wild type allele. Such mutation(s) (e.g. insertion, inversion, deletion and/or replacement of one or more nucleotides) may lead to the encoded protein having reduced in vitro and/or in vivo functionality (reduced function) or no in vitro and/or in vivo functionality (loss of function), e.g. due to the protein e.g. being truncated or having an amino acid sequence wherein one or more amino acids are deleted, inserted or replaced. Such changes may lead to the protein having a different 3D conformation, being targeted to a different sub-cellular compartment, having a modified catalytic domain, having a modified substrate affinity and/or specificity, etc.

"Drought tolerance" or "significantly enhanced drought tolerance" or "drought tolerant plant" refers herein to a (on average) significantly enhanced ability of a plant line, cultivar or variety to withstand water shortage/water stress/drought compared to suitable control plants (e.g. wild type plants), i.e. the symptoms associated with water stress (e.g. wilting of the leaves) are (statistically) significantly reduced in drought tolerant plants compared to the controls exposed to the same water stress conditions and/or (average) recovery and/or survival rate and/or harvestable yield of the plants after exposure to water shortage/water stress/drought conditions is significantly increased compared to the control plants, such as wild type plants. There are various methods for determining whether a plant is drought tolerant, as will be explained elsewhere herein. Preferably a drought tolerant plant has significantly enhanced drought tolerance during all developmental stages, but at least during one of the following developmental stages: as mature plant, during flowering or anthesis, during fruit set and fruit development, during seed development, during fruit ripening. Preferably the plant has in addition also drought tolerance at least at the seed stage and/or during the seedling stage and/or from seedling stage to (and including) mature plant.

"Wild type plant" refers herein to a plant comprising a wild type (WI) SlPP2C1 allele encoding a functional protein (e.g. in contrast to "mutant plants", comprising a mutant SlPP2C1 allele). Such plants are suitable controls in phenotypic assays. Preferably wild type and/or mutant plants are "cultivated plants", i.e. varieties, breeding lines or cultivars of a species, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species, or so-called heirloom varieties or cultivars, i.e. varieties or cultivars commonly grown during earlier periods in human history, but which are not used in modern agriculture.

"Drought" refers preferably both to short term water shortage or stress (artificial, e.g. no irrigation of the soil and/or natural, e.g. no rain fall), e.g. equal to or less than 30 days, 20 days, 15, days, 14 days, 10 days, 9, 8, 7, 6, 5 days, or less and/or long term water shortage or stress (artificial, e.g. no irrigation of the soil and/or natural, e.g. no rain fall), e.g. equal to or more than 31 days, 35 days, 40 days, 45 days, 50 days, 60 days, 70 days, 80 days, 90 days or more.

"Variants" of the SlPP2C1 gene or protein include both natural allelic variants found within the species *S. lycopersicum*, as well as orthologs found in other plant species, such as other dicotyledonous plant species, or monocotyledonous species.

DETAILED DESCRIPTION OF THE INVENTION

The present inventors set out to study genes which are differentially expressed during tomato fruit set, by carrying out transcriptome analysis (cDNA-AFLP) of pollinated ovaries and $GA_3$ (gibberellic acid) treated ovaries (Vriezen et al. 2008, New Phytologist 177:60-76). One gene, which was relatively highly expressed in unpollinated ovaries and less expressed in pollinated ovaries, correlating with ABA (abscisic acid) levels (high in unpollinated ovaries and low after pollination) was characterized further by generating transgenic plants, in order to study the role of this gene in ABA signalling. The tomato gene was named SlPP2C1 (*Solanum lycopersicum* PP2C1), as it encodes a protein of 397 amino acids which comprises a serine/threonine phosphatase 2C catalytic domain in the C-terminal region between about amino acid 84 to 391 (as determined by InterProScan).

It was found that SlPP2C1 is involved in ABA signalling and that over-expression of this gene under control of the CaMV 35S promoter leads to plants which are less sensitive to the phytohormone ABA than wild type plants, while plants in which the gene was co-suppressed (having significantly lower SlPP2C1 transcript levels in at least leaf tissue than wild type plants) had a higher ABA sensitivity (see Examples). Reduced levels of the (wild type) SlPP2C1 protein, thus, enhanced ABA sensitivity, meaning that the SlPP2C1 protein is a negative regulator of ABA signalling.

Surprisingly, it was further found that the tomato plants in which SlPP2C1 transcript levels were significantly reduced compared to wild type plants showed no wilting at all after 9 days of water deprivation, while wild type plants had wilted leaves and SlPP2C1 over-expressing plants showed severe signs of wilting. This was even more surprising as the SlPP2C1 gene and SlPP2C1 protein did not have any significant sequence identity with any known negative regulators of ABA that have been shown to play a role in drought tolerance in *Arabidopsis*, such as ABI1 and HAB1, or with any of the proteins of group A, see Table 1 below.

TABLE 1

Sequence identity between *Arabidopsis* proteins
(putatively) involved in ABA signalling
(Schweigerhofer et al. 2004, supra, see FIG. 1,
group A therein) and SlPP2C1 protein

| *Arabidposis* PP2C subgroup A | SlPP2C1 protein (% sequence identity) |
| --- | --- |
| At5g51760 (AHG1) | 32.3 |
| At3g11410 (AtPP2CA, AHG3) | 38.8 |
| At5g59220 | 38.6 |
| At1g07430 (AIP1) | 37.5 |
| At2g29380 | 39.8 |
| At1g17550 (HAB2) | 33.5 |
| At1g72770 (HAB1) | 32.0 |
| At4g26080 (ABI1) | 36.0 |
| At5g57050 (ABI2) | 37.6 |

Sequence identity is determined using pairwise alignments over the entire length with Needle (Emboss), Blossum 62 matrix, GAP opening penalty=10, GAP extension penalty=0.5

Sequence identity of SlPP2C1 to *Arabidopsis* PP2C, subgroup A, proteins is, thus, low. Notably, null mutations (T-DNA insertions, whereby no mRNA was detectable by RT-PCR) in the protein to which the highest similarity is found, At2g29380, did not show any changes in ABA sensitivity in *Arabidopsis* (Yoshida et al, 2006, Plant Physiology 140:115-126). In addition, this gene is expressed in roots and siliques of *Arabidopsis*, but not in leaves and inflorescences (see FIG. 5 of Xue et al. 2008. BMC Genomics 9:550).

The finding that SlPP2C1 is involved in drought tolerance in tomato can be used to generate transgenic and/or non-transgenic plants with enhanced drought tolerance and, preferably, desired agronomic characteristics. The different embodiments of the invention are described herein below and in the non-limiting Examples. Parts described herein as being applicable to transgenic approaches are generally also applicable to non-transgenic approaches and vice versa, unless indicated otherwise.

In one embodiment transgenic plants in which endogenous SlPP2C1 expression is down-regulated or silenced, at least in leaf tissue, and which are drought tolerant are provided. In another embodiment non-transgenic plants comprising one or more mutant SlPP2C1 alleles (either in homozygous or heterozygous form) and wherein said mutant allele(s) encode(s) an SlPP2C1 protein which has reduced functionality in vitro and/or in vivo compared to the wild type protein, or even no functionality, and whereby the mutation results in the plants (mutant line or progeny thereof) having significantly enhanced drought tolerance compared to plants lacking the mutant allele(s) (wild type plants), are provided herein. Such non-transgenic, drought tolerant plants are in one embodiment of the invention generated using TILLING or Eco-TILLING, but can also be generated using other known mutagenesis methods combined with breeding methods. Thus, in one embodiment the mutant SlPP2C1 allele is induced and identified by humans, using mutagenesis techniques ("induced mutant"), while in another embodiment of the invention the mutant SlPP2C1 allele is a "natural mutant", meaning it is found in natural plant populations. "Induced mutants" are preferably generated in cultivated germplasm and are thus directly present in agronomically valuable lines. On the other hand "natural mutants" or "spontaneous mutants" or "natural variants" or "natural allelic variants/variation" are based on natural variation (polymorphisms/mutations) found in a species and are, thus, likely present in plant material of inferior agronomic quality, not cultivated in modern agriculture, e.g. wild plants. The later alleles then need to be transferred into a cultivated plant having good agronomic characteristics, which is an embodiment of the invention.

Drought stress or dehydration stress is one of the most serious abiotic stresses plants have to cope with world-wide. Four-tenths of the world's agricultural land lies in arid or semi-arid regions. Apart from that, also plants grown in regions with relatively high precipitation may suffer spells of drought throughout the growing season. Many agricultural regions have low rain-fall and rely on irrigation to maintain yields and product quality. Conferring or enhancing the tolerance of crop plants to short and long spells of drought and reducing the water requirement of crops grown in irrigated agriculture is clearly important. The plants provided herein have a lower irrigation requirement and/or higher yield and/or higher percentage survival when grown in regions experiencing short drought spells or longer periods of drought.

Nucleic Acid Sequences and Proteins According to the Invention

In one embodiment of the invention nucleic acid sequences and amino acid sequences of SlPP2C1 are provided, as well as methods for isolating or identifying "variants" thereof for example allelic variants within the species (*Solanum lycopersicum*) or within the genus *Solanum*, or orthologs of SlPP2C1 of other plant species, such as other vegetable species or field crop species.

The wild type SlPP2C1 protein (derived from tomato cultivar Moneymaker) is depicted in SEQ ID NO: 2. It is a protein of 397 amino acids which comprises a (putative) serine/threonine phosphatase 2C catalytic domain in the C-terminal region between about amino acid 84 to 391. In particular, the domain comprises amino acids Asp-Xaa-Phe-Leu-Ile-Leu-Ala-Ser-Asp-Gly-Leu-Trp-Asp-Val (with Xaa being any amino acid, but preferably Glu, see amino acid 307-320 of SEQ ID NO: 2) (SEQ ID NO: 16). There is also a (putative) manganese/magnesium aspartate binding site from amino acid 147 to 149 (DGH or Asp-Gly-His, where Asp binds magnesium or manganese). Alternatively, the domain comprising or consisting of amino acids 144 to 150, i.e. GVXDGHG (where X is any amino acid, preferably Y) (SEC) ID NO: 17) may be involved in interaction with protein kinases.

An "SlPP2C1 protein" (including "variants" thereof, such as proteins encoded by allelic variants of the gene or by orthologs of the gene) may be defined by their amino acid sequence identity to SEQ ID NO: 2 over the entire length, i.e. proteins having a sequence identity of at least about 47%, 48%, 49%, 50% or more (such as but not limited to 55%, 60%, 70%, 80%, 85%, 90%, 95%, 98%, 99% or more) to SEQ ID NO: 2 (as determined by pairwise alignment using Emboss "Needle", Blossum 62 matrix, GAP opening penalty=10, GAP extension penalty=0.5) and having an in vivo function which is essentially similar to that of SlPP2C1.

Also included herein are loss-of-function mutants of the wild type SlPP2C1 proteins (or of variants thereof, as defined above) or reduced-function mutants of wild type SlPP2C1 proteins (or of variants thereof), as described elsewhere, and plants or plant parts comprising one or more nucleotides encoding such mutants and having enhanced drought tolerance compared to plants comprising a nucleic acid sequence encoding a wild type protein.

Preferably, a SlPP2C1 protein according to the invention also comprises at least a catalytic serine/threonine phosphatase domain in the C-terminal region, i.e. a domain comprising at least 60%, 70%, 80%, 90% or preferably at least 95%, 98%, 99% or more amino acid sequence identity to amino acid 84 to 391 of SEQ ID NO: 2 (as determined by pairwise alignment using Emboss "Needle", Blossum 62 matrix, GAP opening penalty=10, GAP extension penalty=0.5). In one embodiment an SlPP2C1 protein according to the invention comprises the sequence Asp-Xaa-Phe-Leu-Ile-Leu-Ala-Ser-Asp-Gly-Leu-Trp-Asp-Val (with Xaa being any amino acid, but preferably Glu) or a sequence which has 90% or 95% or 98% or more sequence identity to this sequence (as determined by pairwise alignment using Emboss "Needle", Blossum 62 matrix, GAP opening penalty=10, GAP extension penalty=0.5). Preferably an SlPP2C1 protein further comprises at least one DGH motif, i.e. at least one DGH sequence or GVXDGHG sequence (where X is any amino acid, preferably Y).

A "function which is essentially similar to the function of SlPP2C1" refers herein to the protein having a proven function in sensitivity/tolerance to drought stress and/or in determining ABA sensitivity of the plant tissue. Plants overexpressing SlPP2C1, or a variant thereof, in at least leaf tissue, are significantly more susceptible to drought stress than wild type plants and/or have a significantly reduced ABA sensitivity compared to controls (e.g. wild type plants or plants transformed with an empty vector). Vice versa, plants with reduced levels of fully functional (wild type) SlPP2C1 protein, or a variant thereof, in at least the leaf tissue, are significantly less susceptible to drought stress than wild type plants and/or have a significantly enhanced ABA sensitivity compared to controls.

Thus, the function of a (putative) SlPP2C1 protein can be tested using a variety of known methods, preferably by comparing the phenotype of transformants constitutively expressing the protein being tested to the phenotype of SlPP2C1 over-expressing transformants of the same host species (and variety) (preferably comprising a chimeric SlPP2C1 encoding gene stably integrated into the host's genome), allowing a direct comparison of the functional effect on the phenotype of the transformants.

Similarly, transformants in which the SlPP2C1 gene (or variant) is silenced or down-regulated (e.g. mRNA of SlPP2C1 is significantly reduced at least in leaf tissue compared to wild type or control transformants) can be used to determine the function. A "significant reduction" of the mRNA of SlPP2C1 transcript refers to the target mRNA being present at a level of less than or equal to 90%, 80%, 70%, 60%, 50% 40%, 30%, 20% or less (10%, 5% or 0%) of the transcript level found in the wild type or control transformants (e.g. empty vector transformant). It is understood that in any transformation experiments a certain degree of variation in the phenotype of transformants is seen, normally due to position effects in the genome and/or due to copy number. A skilled person will know how to compare transformants to one another, e.g. by selecting single copy number events and analysing their phenotypes. Other methods of determining or confirming in vivo gene/protein function include the generation of knock-out mutants or reduced-function mutants or transient expression studies. Promoter-reporter gene expression studies may also provide information as to the spatio-temporal expression pattern and the role of the protein.

Constitutive (over)expression of a SlPP2C1 gene, or a gene encoding a variant thereof, should result in one or more of the following phenotypic changes compared to the wild type plants or control transformants:
  Significantly increased sensitivity to water stress (i.e. significantly reduced drought tolerance) and/or
  Significantly reduced ABA sensitivity.

A "significantly increased sensitivity to water stress" or "significantly reduced drought tolerance" refers to an average, statistically significant increase of leaf wilting symptoms of a plurality of plants comprising the SlPP2C1 allele by at least 10% compared to control levels and can, for example, be tested as described in the Examples or equivalent experiments. In short, a plurality (e.g. at least 10, 15, 20 or more of a transgenic line) of transformed plants and control plants of the same age (e.g. mature plants) are saturated with water at the start of the experiment and are then not watered for an extended period of time, e.g. at least about 7, 8, 9, 10, 11, 12, 13, 14 days or more, e.g. 3 weeks or 4 weeks or more (depending on the plant species). When the control plants start to show wilting of the leaves ("slight wilting" or "moderate wilting"), all plants are assessed for signs of wilting of the leaves using e.g. visual assessment. Wilting symptoms of leaves can, for example, be scored on a scale of 4-1, as "highly/severely wilted" (4), "moderate wilted" (3), "slightly wilted" (2) or "no wilting" (1). Plants are said to have a significantly reduced drought tolerance if (average) wilting is increased by at least 10%, preferably at least 20%, 30%, 40%, 50%, 60%, 70%, 80%, 90% or 100% compared to the wild type (or empty vector transformed) control. Alternatively or in addition, field trials can be carried out to test and/or confirm whether or not a significantly reduced drought tolerance is seen in the field under spells of water-stress.

Other assays may be used, of course. For example, a period of water deprivation may be followed by a period of recovery (watering) and the percentage of plant survival may be assessed, see e.g. Zheng et al. (2009, Biochemical and Biophysical Research Communications 379: 986, LH Column). Plants are said to have a significantly reduced drought tolerance if the percentage survival is reduced by at least 10%, preferably at least 20%, 30%, 40%, 50%, 60%, 70%, 80%, 90% or 100% compared to the wild type (or empty vector transformed) control. See also Xiong et al. 2006 (Plant Physiology 142: 1065-1074) and Yu et al. 2008 (The Plant Cell 20: 1134-1151).

"Significantly reduced ABA sensitivity" can also be tested as described in the Examples by testing seed germination percentages on one or more different ABA concentrations and/or root elongation on one or more different ABA concentrations. In summary, seed germination on medium comprising ABA is at least 5%, 10%, 20%, 30%, 40%, 50% or more, higher for the SlPP2C1 overexpressing transformant than for the control seeds on the same ABA concentration. For example, on 1 or 3 µM ABA, 50% of wild type seeds germinate, while 55%, 60% or more of transformed (SlPP2C1 overexpressing) seeds germinate. Thus, seed germination of overexpressing transformants is inhibited less by ABA. Root growth/elongation of overexpressing transformants is also inhibited less by ABA.

Down-regulation or silencing of a SlPP2C1 gene, or a gene encoding a variant member, should result in one or more of the following phenotypic changes compared to the wild type plants or control transformants:
  Significantly reduced sensitivity to water stress (i.e. significantly enhanced drought tolerance) and/or
  significantly enhanced ABA sensitivity.

A "significantly reduced sensitivity to water stress" or "significantly enhanced drought tolerance" refers to an average, statistically significant decrease of leaf wilting symptoms of a plurality of plants, in which the SlPP2C1 gene is down-regulated or silenced, by at least 10% compared to control levels (e.g. wild type plants or empty vector transformants) and can, for example, be tested as described in the Examples or using equivalent methods. In short, a plurality of transformed plants (e.g. at least 10, 15, 20 or more of a transgenic line) and controls of the same age are saturated with water at the start of the experiment and are then not watered for an extended period of time, e.g. at least about 7, 8, 9, 10, 11, 12, 13, 14 days or more, e.g. 3 weeks or 4 weeks or more (depending on the plant species). When the control plants start to show wilting of the leaves ("slight wilting" or "moderate wilting"), all plants are assessed for signs of wilting of the leaves using e.g. visual assessment. Wilting symptoms of leaves can, for example, be scored on a scale of 1 to 4, as "highly/severely wilted" (4), "moderately wilted" (3), "slightly wilted" (2) or "no wilting" (1). Plants are said to have a significantly enhanced drought tolerance if (average) wilting is reduced by at least 10%, preferably at least 20%, 30%, 40%, 50%, 60%, 70%, 80%, 90% or 100% compared to the control plants. Alternatively or in addition field trials can be used to determine whether a significantly enhanced drought tolerance is conferred by the down-regulation or silencing of endogenous SlPP2C1 gene(s).

Other assays may be used, of course. For example, a period of water deprivation may be followed by a period of recovery (watering) and the percentage of plant survival may be assessed, see e.g. Zheng et al. (2009, Biochemical and Biophysical Research Communications 379: 986, LH Column). Plants are said to have a significantly enhanced drought tolerance if the percentage survival is enhanced by at least 10%, preferably at least 20%, 30%, 40%, 50%, 60%, 70%, 80%, 90% or 100% compared to the wild type (or empty vector transformed) control. See also Xiong et al. 2006 (Plant Physiology 142: 1065-1074) and Yu et al. 2008 (The Plant Cell 20: 1134-1151).

The above assays, or equivalent assays, can also be used to determine whether plant comprising a mutant SlPP2C1 allele (e.g. a loss-of-function or a reduced-function mutant) has significantly enhanced drought tolerance, as will be described further down.

"Significantly enhanced ABA sensitivity" can also be tested as described in the Examples. In summary, average seed germination on medium comprising ABA is at least 10%, 20%, 30%, 40%, 50%, or more, lower for the SlPP2C1 down-regulated or silenced transformants than for the control plants (e.g. wild type) on the same ABA concentration. For example, on 1 or 3 µM ABA, 50% of wild type seeds germinate, while less than 40%, 35%, 30%, or less, of transformed (SlPP2C1 silenced) seeds germinate. Thus, seed germination of down-regulated or silenced transformants is inhibited more by ABA. Root growth of down-regulated or silenced transformants is also inhibited more by ABA.

The exact methods used may vary, depending for example on the plant species. Assays for determining drought tolerance and/or ABA sensitivity in vegetable species or in field crops are known in the art. It is also understood that alternative methods exist to assess the phenotypes. Such methods are within the scope of the skilled person.

The above methods can be used to test whether any putative SlPP2C1 gene, such as an allele from a wild or cultivated tomato plant or from a tomato breeding line or PI (plant introduction) line or from a different species (e.g. tobacco, or other vegetable species or from field crop species) is indeed a SlPP2C1 variant, which can then be used to generate transgenic and/or non-transgenic plants having (significantly) enhanced drought tolerance compared to suitable controls, such as the wild type plant. It is understood that regarding transgenic plants, preferably plants having good agronomic characteristics are transformed and regenerated, i.e. cultivated plants (for example high yielding cultivars or breeding lines) and that the most suitable controls are empty vector transformants of the same line or a plurality of plants of the non-transformed line as such.

In addition, in vitro phosphatase activity assays can be carried out to test protein activity/functionality, see e.g. Gosti et al. 1999, Plant Cell 11: 1897-1910, Material and Methods—PP2C Activities, page 1907, where the protein is expressed in *E. coli* and the enzyme activity is assayed using $^{32}P$ labeled casein as substrate. Such activity assays are also suitable for determining whether specific types of mutant SlPP2C1 proteins (e.g. generated by TILLING or other methods, see elsewhere herein) or chimeric proteins retain all or partial functionality. See also Bertauche et al, 1996, Eur. J. Biochem 241: page 195 for a phosphates assay and page 194 for expression in *E. coli*.

A SlPP2C1 protein has "reduced function in vitro" if the percentage of de-phosphorylation of $^{32}P$-casein by the mutant protein is equal to or less than 70% of the wild type protein (under the same assay conditions, e.g. 1 or 2 µg protein incubated with $^{32}P$-casein for 2 hours at 30 degrees Celsius in the presence of 20 mM magnesium acetate, and in the presence of okadaic acid), preferably equal to or less than about 60%, 50%, 40%, 30%, 20%, 10% ("reduction of function") or about 0% of the wild type protein (i.e. complete "loss of function"). A protein having reduced function in vitro can be used to infer that the protein also has "reduced function or no function in vivo", i.e. in planta, e.g. at least in the leaf tissue and/or fruit tissue. For example, a plant comprising one (heterozygous) or two (homozygous) alleles encoding a mutant protein having reduced or no function in vitro results in the plant having significantly enhanced drought tolerance (compared to plants lacking the mutant allele/having wild type alleles) and therefore also reduced function or no function in vivo. The in vivo reduced-function or loss-of-function of the protein is confirmed by drought tolerance assays (e.g. in the field or as described in the Examples) of plants homozygous or heterozygous for the mutant allele.

Other putative SlPP2C1 genes/proteins can be identified in silico, e.g. by identifying nucleic acid or protein sequences in existing nucleic acid or protein database (e.g. GENBANK, SWISSPROT, TrEMBL) and using standard sequence analysis software, such as sequence similarity search tools (BLASTN, BLASTP, BLASTX, TBLAST, FASTA, etc.). Putative amino acid sequences or nucleic acid sequences comprising or encoding an SlPP2C1 protein (as defined above) are selected, cloned or synthesized de novo and tested for in vivo functionality by e.g. overexpression or silencing in a plant host. It is noted that the designation SlPP2C1 is also used herein for proteins which are derived from species other than *Solanum lycopersicum*, i.e. the prefix Sl does herein not limit the protein as being from a particular species.

One putative ortholog of the tomato SlPP2C1 gene and protein is the potato protein of SEQ ID NO: 15 (StPP2C1), encoded by the cDNA of SEQ ID NO: 14 (StPP2C1). The StPP2C1 protein has 89.1% amino acid sequence identity with SlPP2C1 and 91.5% nucleotide sequence identity with SlPP2C1 (using Emboss-Needle, Gap opening=10.0, Gap extension=0.5, and Blosum62 for proteins or dnafull for nucleic acids).

The SlPP2C1 proteins according to the invention may be isolated from natural sources, synthesized de novo by chemical synthesis (using e.g. a peptide synthesizer such as supplied by Applied Biosystems) or produced by recombinant host cells (e.g. *E. coli*). The SlPP2C1 proteins according to the invention may be used to raise mono- or polyclonal antibodies, which may for example be used for the detection of SlPP2C1 proteins in tissue samples, such as leaves (immunochemical analysis methods and kits).

In one embodiment reduced-function or loss-of-function mutant SlPP2C1 proteins are provided and plants and plant parts comprising one or more SlPP2C1 alleles, which encode reduced-function or loss-of-function mutants. Any type of mutation may lead to a reduction in function or loss of function of the encoded protein, e.g. insertion, deletion or replacement of one or more nucleotides in the cDNA (SEQ ID NO: 1, or variants) or in the corresponding genomic SlPP2C1 sequence (SEQ ID NO: 11, or variants). The "corresponding genomic sequence" is the endogenous DNA sequence (depicted in SEQ ID NO: 11, or variants thereof) from which SEQ ID NO: 1 mRNA (cDNA), or variant mRNA is transcribed. The wild type genomic region which is transcribed into mRNA comprises nucleotides 2591 to 5050, which includes the 5' UTR (nucleotides 2591-2675 of SEQ ID NO: 11), two introns and the 3' UTR (nucleotides 4976-5050 of SEQ ID NO: 11). The in vitro and/or in vivo function of such proteins can be tested as described above. Plants comprising a nucleic acid sequence encoding such mutant reduced-function or loss-of-function proteins and having enhanced drought tolerance, can for example be generated using TILLING or identified using EcoTILLING, as described further below.

In one embodiment of the invention (cDNA or genomic) nucleic acid sequences encoding such mutant proteins comprise one or more non-sense and/or mis-sense mutations, e.g. transitions (replacement of purine with another purine (A↔G) or pyrimidine with another pyrimidine (C↔T)) or transversions (replacement of purine with pyrimidine, or vice versa (C/T↔A/G). In one embodiment the non-sense and/or mis-sense mutation(s) is/are in the nucleotide sequence encoding the C-terminal region, preferably in the (putative) catalytic domain of amino acid 84 to 391 of SEQ ID NO: 2 (or of an essentially similar domain in a variant SlPP2C1 protein, i.e. in a domain comprising at least 80%, 90%, 95%, 98%, 99% amino acid identity to this domain). In another embodiment the non-sense and/or mis-sense mutation(s) is/are in the nucleic acid sequence encoding amino acid 307-320 of SEQ ID NO: 2 (or a variant thereof). In another embodiment the non-sense and/or mis-sense mutation(s) is/are in the nucleic acid sequence encoding the putative magnesium binding site, i.e. Asp-Gly-His (amino acid 147-149 of SEQ ID NO:2 or variant thereof) and/or in the nucleic acid sequence encoding the putative protein kinase interaction domain (amino acids 144-150 of SEQ ID NO: 2 or of an essentially similar domain in a variant SlPP2C1 protein).

In a specific embodiment nucleic acid sequences encoding such mutant proteins comprise one or more mis-sense mutations in amino acids Gly148, Ser171, Ala155, Gly132 of SEQ ID NO: 2 (or the equivalent amino acid in a variant SlPP2C1 protein). Also mutant plants, seeds and plant parts comprising one or more of the above mis-sense mutations and having significantly enhanced stress tolerance, especially drought tolerance, are encompassed herein.

In a specific embodiment of the invention drought tolerant plants comprising a mutant loss-of-function or reduced-function SlPP2C1 allele are provided, for example whereby the mutant allele comprises a mis-sense mutation in the nucleotide sequence encoding GVXDGHG (with X being any amino acid, preferably Y) (SEQ ID NO: 17), or an essentially similar sequence (comprising at least 80%, 90%, 95%, 98%, 99% amino acid identity to this domain), resulting in at least one amino acid being replaced, e.g. resulting in for example DVXDGHG (SEQ ID NO: 18) or GVXDGHD (SEQ ID NO: 19) or DVXDGHD (SEQ ID NO: 20) or GVXDDHG (SEQ ID NO: 21).

The function of specific domains, such as the N-terminal or the catalytic domain or the magnesium binding and/or protein kinase interaction domain, can be analyzed by deleting all or part of the domain(s) in a SlPP2C1 protein or the introduction of one or more mutations into the domain, and analysis of the resulting effect on the function of the SlPP2C1 protein. Likewise, plants comprising spontaneous or induced mutations (e.g. generated by TILLING or identified by EcoTILLING) can be analyzed for the mutation and the phenotype of the plant comprising the mutation, in particular drought tolerance.

In one embodiment, the loss-of-function or reduced-function SlPP2C1 protein is a truncated protein, i.e. a protein fragment of any one of the SlPP2C1 proteins defined further above (including variants thereof). In general EMS (Ethyl methanesulfonate) induces substitutions of guanine/cytosine to adenin/thymine. In case of a glutamine (Gln or Q, encoded by the nucleotides CAA or CAG) or arginine (Arg or R, encoded by the nucleotides CGA) codon, a substitution of the cytosine for thymine can lead to the introduction of a stop codon in the reading frame (for example CAA/CAG/CGA to TAA/TAG/TGA) resulting in a truncated protein. The truncated protein may, for example, comprise amino acids 1 to any one of the Gln (encoded by CAA or CAG) or Arg amino acids (encoded by CGA) downstream of the start codon of SEQ ID NO: 2, or of a variant of SEQ ID NO: 2. Alternatively, the truncated protein may, for example, comprise or consist of amino acids 1-5, 1-1-20, 1-28, 1-33. 1-35, 1-36, 1-40, 1-43, 1-44, 1-46, 1-48, 1-49, 1-5-. 1-51, 1-54, 1-57, 1-66, 1-70, 1-71, 1-72, 1-73, 1-83 of SEQ ID NO: 2, or 1-85, 1-88, 1-91, 1-93, 1-94, 1-97, 1-104, 1-106, 1-110, 1-120 1-130, 1-141, 1-149, 1-151, 1-160, 1-170, 1-200, 1-301, 1-302, 1-305, 1-307, or other truncated proteins of SlPP2C1 (SEQ ID NO: 2), or of a variant thereof.

Also provided are nucleic acid sequences (genomic DNA, cDNA, RNA) encoding SlPP2C1 proteins, such as for example SlPP2C1 depicted in SEQ ID NO:2 or variants thereof as defined above (including any chimeric or hybrid proteins or mutated proteins or truncated proteins described), or any SlPP2C1 protein from another species. Due to the degeneracy of the genetic code various nucleic acid sequences may encode the same amino acid sequence. Any nucleic acid sequence encoding an SlPP2C1 protein (as defined above, including variants thereof) is herein referred to as SlPP2C1. The nucleic acid sequences provided include naturally occurring, artificial or synthetic nucleic acid sequences. A nucleic acid sequences encoding SlPP2C1 is provided for in SEQ ID NO: 1 (cDNA sequence from tomato) and SEQ ID NO: 11 (genomic DNA from tomato encoding wild type SlPP2C1 protein). The corresponding genomic sequence can be isolated using routine methods, such as PCR using specific or degenerate primers based on SEQ ID NO: 1 or SEQ ID NO: 11.

It is understood that when sequences are depicted in as DNA sequences while RNA is referred to, the actual base sequence of the RNA molecule is identical with the difference that thymine (T) is replace by uracil (U).

Also provided are nucleic acid sequences (genomic DNA, cDNA, RNA) encoding mutant SlPP2C1 proteins, i.e. reduced function or loss-of-function SlPP2C1 proteins, as described above. For example, SlPP2C1 nucleic acid sequences comprising one or more non-sense and/or mis-sense mutations in the wild type SlPP2C1 coding sequence, rendering the encoded protein non-functional or having a reduced function in vivo and/or in vitro. Also sequences with other mutations are provided, such as splice-site mutants, i.e. mutations in the genomic SlPP2C1 sequence leading to aberrant splicing of the pre-mRNA, and/or frame-shift mutations, and/or insertions and/or deletions of one or more nucleic acids.

Also included are variants and fragments of SlPP2C1 nucleic acid sequences, such as nucleic acid sequences hybridizing to SlPP2C1 nucleic acid sequences, e.g. to SEQ ID NO: 1, under stringent hybridization conditions as defined. Variants of SlPP2C1 nucleic acid sequences also include nucleic acid sequences which have a sequence identity to SEQ ID NO: 1 or SEQ ID NO: 11 (nucleotides 2676-4975) of at least 50% or more, preferably at least 55%, 60%, 70%, 80%, 85%, 90%, 95%, 98%, 99% or more (as determined by Emboss "needle" using default parameters, i.e. gap creation penalty=10, gap extension penalty=0.5, scoring matrix nwsgapdna). It is clear that many methods can be used to identify, synthesise or isolate variants or fragments of SlPP2C1 nucleic acid sequences, such as nucleic acid hybridization, PCR technology, in silico analysis and nucleic acid synthesis, and the like. Variants of SEQ ID NO: 1 or SEQ ID NO: 11 (nucleotides 2676-4975) may either encode wild type, functional SlPP2C1 proteins (e.g. alleles from other tomato varieties or breeding lines or wild accessions, or orthologs from other species than tomato), or they may encode reduced-function or loss-of function mutant alleles of any of these, as for example generated or identified by methods such as TILLING or EcoTILLING, or other methods.

Fragments include parts of any of the above SlPP2C1 nucleic acid sequences (or variants), which may for example be used as primers or probes or in gene silencing constructs. Parts may be contiguous stretches of at least about 10, 15, 19, 20, 21, 22, 23, 25, 50, 60, 100, 200, 300, 450, 500, 600, 700, 800, 900, or more, nucleotides in length, of either the coding strand (sense strand) or the complementary strand (anti-sense strand). Also included are, therefore, fragments of SlPP2C1 nucleic acid sequences, whereby a fragment of at least about 20, 30, 40, 50, 60, 100, 150, 200 300, 450, 500, 600, 700, 800, 900 nucleotides in length comprises at least 50, 60, 70, 75%, more preferably at least 80, 90, 95, 98, 99% or more (100%) nucleic acid sequence identity to another fragment of a SlPP2C1 nucleic acid sequence of about the same length (as determined by pairwise alignment using Emboss "needle" using default parameters, i.e. gap creation penalty=10, gap extension penalty=0.5, scoring matrix nwsgapdna).

Primer pairs which can be used for PCR amplification of SlPP2C1 transcripts (mRNA or corresponding cDNA) from plant tissue DNA sample are, for example, depicted in SEQ ID NO: 3 and 4 and in primer pair of SEQ ID NO: 9 and 10. Such primer pairs can be used to detect and quantify SlPP2C1 expression in plant tissue, e.g. in tomato leaf tissue. Likewise other specific or degenerate primers can be designed based on SEQ ID NO: 1 or SEQ ID NO: 11 (nucleotides 2676-4975) and used to amplify variants alleles of SlPP2C1 from other tomato lines or from other species.

Once a specific mutant SlPP2C1 allele has been generated and/or identified (e.g. by TILLING or EcoTILLING), also primers or probes specific for the mutant allele can be designed and an assay can be developed which detects the presence and/or absence of the mutant allele in a plant or plant part (using allele specific detection assays). Molecular marker assays for detection and/or transfer (e.g. by MAS, marker assisted selection) of the mutant allele can be developed. E.g. a SNP detection assay or a CAPS marker can be developed which detects the presence of mutant SlPP2C1 nucleic acid sequence in DNA of plants and/or which can be used for transfer of the allele into other plants.

In one embodiment mutant nucleic acid sequences are provided, whereby the SlPP2C1 nucleic acid sequence comprises one or more mutations leading to either a loss-of-function mutant of the SlPP2C1 protein or a reduced-function mutant of the SlPP2C1 protein. This aspect of the invention will be described in more detail elsewhere herein.

Plants can also be identified or generated (e.g. by homologous recombination, or by insertion, deletion or replacement of one or more nucleotides, etc.) which have one or more mutations in the SlPP2C1 regulatory region(s), e.g. the promoter, whereby SlPP2C1 gene expression, i.e. mRNA levels (of SEQ ID NO: 1 or variants) is/are significantly reduced in the plant compared to the wild type and whereby the plant has significantly enhanced drought tolerance.

The nucleic acid sequence described above, or fragments thereof, particularly DNA sequence, encoding the SlPP2C1 proteins of this invention (or variants of these) can be inserted in expression vectors (in co-suppression approaches) or into gene silencing vectors to generate drought tolerant plants.

In one embodiment of the invention SlPP2C1 gene expression is downregulated in a host cell, plant or specific tissue(s), by e.g. RNAi approaches, as described elsewhere.

In another embodiment plants comprising one or more mutant SlPP2C1 alleles are provided, whereby the mutation(s) confer enhanced drought tolerance on the plant compared to plants lacking the mutant allele(s). Mutant alleles are preferably generated by mutagenesis of the plant or seed and by identifying those plants or seeds which comprise one or more mutations in the target PP2C1 allele(s) and whereby the mutation results in abolishment of transcription or translation (so that no SlPP2C1 protein is produced), or in translation of a reduced-function or loss-of-function SlPP2C1 protein. The reduction of functional, wild type SlPP2C1 protein, at least in leaf tissue, confers enhanced drought tolerance onto the plant, plant part or seed.

In another embodiment of the invention PCR primers and/or probes and kits for detecting the SlPP2C1 DNA sequences are provided. Degenerate or specific PCR primer pairs to amplify SlPP2C1 DNA from samples can be synthesized based on SEQ ID NO: 1 or SEQ ID NO: 11 (e.g. based on nucleotides 2676-4975 or 2591-5050) as known in the art (see Dieffenbach and Dveksler (1995) PCR Primer: A Laboratory Manual, Cold Spring Harbor Laboratory Press, and McPherson at al. (2000) PCR-Basics: From Background to Bench, First Edition, Springer Verlag, Germany). Likewise, DNA fragments of SEQ ID NO: 1 or SEQ ID NO: 11 (or variants thereof) can be used as hybridization probes. A SlPP2C1 detection kit may comprise either SlPP2C1 specific primers and/or SlPP2C1 specific probes, and an associated protocol to use the primers or probe to detect SlPP2C1 DNA in a sample. Such a detection kit may, for example, be used to determine, whether a plant has been transformed with an SlPP2C1 gene (or part thereof) of the invention or whether a plant comprises one or more mutant SlPP2C1 alleles. Because of the degeneracy of the genetic code, some amino acid codons can be replaced by others without changing the amino acid sequence of the protein.

In another embodiment antibodies that bind specifically to a SlPP2C1 protein, or mutant SlPP2C1 protein, according to the invention are provided. In particular monoclonal or polyclonal antibodies that bind to SlPP2C1, or to fragments or variants thereof (e.g. mutant proteins), are encompassed herein. An antibody can be prepared by using a SlPP2C1 protein according to the invention as an antigen in an animal using methods known in the art, as e.g. described in Harlow and Lane "Using Antibodies: A laboratory manual" (New York: Cold Spring Harbor Press 1998) and in Liddell and Cryer "A Practical Guide to Monoclonal Antibodies" (Wiley and Sons, 1991). The antibodies can subsequently be used to isolate, identify, characterize or purify the SlPP2C1 protein to which it binds, for example to detect the SlPP2C1 protein in a sample, allowing the formation of an immunocomplex and detecting the presence of the immunocomplex by e.g. ELISA (enzyme linked immunoassay) or immunoblot analysis. Also provided are immunological kits, useful for detecting the SlPP2C1 proteins, protein fragments or epitopes in a sample provided. Samples may be cells, cell supernatants, cell suspensions, tissues, etc. Such a kit comprises at least an antibody that binds to a SlPP2C1 protein and one or more immunodetection reagents. The antibodies can also be used to isolate/identify other SlPP2C1 proteins, for example by ELISA or Western blotting.

It is clear that many methods can be used to identify, synthesise or isolate variants or fragments of SlPP2C1 nucleic acid sequences, such as nucleic acid hybridization, PCR technology, in silico analysis and nucleic acid synthesis, and the like. Thus, an SlPP2C1-protein encoding nucleic acid sequence may be a sequence which is chemically synthesized or which is cloned from any plant species.

Transgenic Drought Tolerant Plants

Transgenic plants, seeds and plant parts are provided in which SlPP2C1 is silenced, preferably at least in leaf tissue or aerial tissue, and which have enhanced drought tolerance compared to wild type (non-transgenic) control plants or other control plants (e.g. empty vector transformants).

In one embodiment of the invention a homologous or heterologous nucleic acid sequence is used to silence the endogenous SlPP2C1 gene(s) of the host species to be transformed. For example, a potato SlPP2C1 gene, such as StPP2C1 of SEQ ID NO: 14 (or variant or fragment thereof) may be used to silence SlPP2C1 gene expression in transgenic tomato or aubergine plants. Alternatively, homologous SlPP2C1 nucleic acid sequences may be used. For example a sequence originating from a particular plant species (e.g. from tomato) is reintroduced into said species (tomato). Thus, in one embodiment, the SlPP2C1 DNA corresponds to, or is a modification/variant of the endogenous SlPP2C1 DNA of the species which is used as host species in transformation. Thus, a tomato SlPP2C1 cDNA or genomic DNA (or a variant or fragment thereof) is preferably used to transform tomato plants. In addition (for regulatory approval and public acceptance reasons) the homologous or heterologous nucleic acid sequence may be operably linked to a transcription regulatory sequence, especially a promoter, which also originates from a plant species or even from the same plant which is to be transformed.

To generate plants comprising a chimeric gene, which upon expression results in silencing of the expression of an endogenous SlPP2C1 gene or gene family, methods known in the art can be used.

"Gene silencing" refers to the down-regulation or complete inhibition of gene expression of one or more target genes, e.g. SlPP2C1 genes, in a host cell or tissue. It is understood that in any transformation experiments a certain degree of variation in the phenotype of transformants is seen, normally due to position effects in the genome and/or due to copy number. Generally, "weak" and "strong" gene silencing plants are distinguished herein (all of which are embodiments of the invention), wherein "weak" gene silencing (RNAi) events refer to plants or plant parts wherein the endogenous target gene expression is reduced by about 15, 20 or 30% compared to the control tissue and "strong" gene silencing (RNAi) events refer to plants or plant parts wherein the endogenous target gene expression is reduced by at least about 50, 60, 70, 80, 90% or more compared to the control tissue (e.g. wild type). Silencing can be quantified by, for example, quantifying the transcript level of the target gene (e.g. using quantitative RT-PCR) and/or by determining and optionally quantifying the enzymatic activity of the target SlPP2C1 protein and/or by assessing and optionally quantifying resulting phenotype (enhanced drought tolerance and/or enhanced ABA sensitivity).

Without limiting the scope of the invention, plants having an optimal silencing level can be selected, so that resulting plants have significantly enhanced drought tolerance under the climatic conditions to which they are exposed in the field, while having minimal negative side-effects, such as reduced yield, reduced number of fruits, etc. compared to controls. Preferably survival and/or yield are increased in the drought tolerant plants.

The use of inhibitory RNA to reduce or abolish gene expression is well established in the art and is the subject of several reviews (e.g Baulcombe 1996, Plant Cell 8(2):179-188; Depicker and Van Montagu, 1997, Curr Opin Cell Biol. 9(3): 373-82). There are a number of technologies available to achieve gene silencing in plants, such as chimeric genes which produce antisense RNA of all or part of the target gene (see e.g. EP 0140308 B1, EP 0240208 B1 and EP 0223399 B1), or which produce sense RNA of the target gene (also referred to as "co-suppression"), see EP 0465572 B1.

The most successful approach so far has however been the production of both sense and antisense RNA of the target gene ("inverted repeats"), which forms double stranded RNA (dsRNA) or a stem-loop structure (hairpin RNA, hpRNA) in the cell and silences the target gene(s) upon transcription from an upstream promoter. Methods and vectors for dsRNA and hpRNA production and gene silencing have been described in EP 1068311, EP 983370 A1, EP 1042462 A1, EP 1071762 A1 and EP 1080208 A1.

A chimeric gene for plant transformation may, therefore, comprise a transcription regulatory region which is active in plant cells operably linked to a sense and/or antisense DNA fragment (or a complete nucleic acid sequence) of or complementary or substantially similar to, a SLPP2C1 target gene or gene family.

Generally short (sense and anti-sense) stretches of the target gene sequence, such as 17, 18, 19, 20, 21, 22, 23, 24, 25 or 26 nucleotides of coding and/or non-coding sequence of the target gene are sufficient. Longer sequences can also be used, such as at least about 50, 100, 200, 250, 500, 1000 or more nucleotides. Even DNA corresponding to, or being complementary to, the complete transcript RNA or mRNA may be used to make a sense and/or antisense construct. Preferably, the sense and antisense fragments/sequences are separated by a spacer sequence, such as an intron, which forms a loop (or hairpin) upon dsRNA formation.

In principle, any SlPP2C1 gene or gene family can be targeted. For example, one or several specific SlPP2C1 alleles may be silenced by choosing a nucleic acid region of their primary or mRNA transcripts specific for these alleles (see Byzova et al. Plant 2004 218: 379-387 for allele specific silencing in an organ specific manner). Similarly, a whole gene family may be targeted for silencing by choosing one or more conserved regions of the transcripts for making the silencing construct. As mentioned above, the DNA region used in sense and/or antisense orientation does not need to be part of the coding region, but may also correspond to, or be complementary to, parts of the primary transcript (comprising a 5' and 3' untranslated sequence and introns, as depicted in nucleotides 2591-5050 of SEQ ID NO: 11) or to parts of the mRNA transcript (where any introns have been removed and a polyA tail has been added). It is understood that in a DNA sequence which corresponds to an RNA sequence the U is replaced by a T. It is also noted that in a chimeric gene which transcribes a dsRNA or hpRNA targeting capable of silencing SlPP2C1 gene expression upon transcription in a host cell, the sense and antisense regions need not be of equal length and one region may be longer than the other.

Thus, for example SEQ ID NO: 1 or variants thereof as described above, or fragments of any of these, or the genomic sequence or primary transcript sequence of SEQ ID NO: 1 (as depicted in SEQ ID NO: 11 from nucleotide 2591 to 5050), may be used to make a SlPP2C1 gene silencing gene and vector and a transgenic plant in which one or more SlPP2C1 genes are silenced in all or some tissues or organs, or upon induction (see e.g. Wielopolska et al. Plant Biotechnol J. 2005 6:583-90). A convenient way of generating hairpin constructs is to use generic vectors such as pHANNIBAL, pHELLSGATE, pSTARGATE vectors based on the Gateway® technology (see Wesley et al. 2004, Methods Mol Biol. 265:117-30; Wesley et al 2003, Methods Mol Biol. 236:273-86 and Helliwell & Waterhouse 2003, Methods 30(4):289-95), incorporated herein by reference. See also http://www.pi.csiro.au/rnai/ for other gene silencing vectors, such as inducible silencing vectors and vectors for silencing of multiple target genes and for the program MatchPoint which can be used to find the best sequence to use for silencing the target gene.

By choosing conserved nucleic acid sequences all SlPP2C1 gene family members in a host plant can be silenced. The silencing of all family members of a host plant is a specific embodiment.

In one embodiment the promoter, which is operably linked to the sense and/or antisense nucleic acid sequence (to make a chimeric silencing/RNAi gene) is selected from a constitutive promoter, an inducible promoter (e.g. stress inducible, light inducible, chemically inducible, etc.), a hormone inducible promoter (e.g. ethylene or ABA inducible, etc.) a leaf specific promoter or promoter active in aerial tissue. Also early dehydration responsive promoters, such as RD2, are encompassed herein, as well as other stress inducible promoters, such as RD29 (Yamaguchi-Shinozaki and Shinozaki 1993, Mol Gen Genet 236: 331-340).

In certain embodiments a fruit specific promoter may be suitable. Also, the promoter of an SlPP2C gene itself may be used for silencing approaches. The promoter from tomato is comprised in SEQ ID NO: 11 from nucleotide 1-2675, especially the promoter comprises or consists of about 2000 nucleotides upstream of the ATG translation start codon at position 2676-2679 of SEQ ID NO: 11) or functional fragments thereof (e.g. 1500 bp, 1000 bp or less upstream of ATG). Optionally a 3' UTR may be operably linked to the 3' end of the chimeric gene, so that the operably linked DNA elements include promoter—SlPP2C1 RNAi gene—3' UTR.

Preferred constitutive promoters include: the strong constitutive 35S promoters or enhanced 35S promoters (the "35S promoters") of the cauliflower mosaic virus (CaMV) of isolates CM 1841 (Gardner et al., 1981, Nucleic Acids Research 9, 2871-2887), CabbB-S (Franck et al., 1980, Cell 21, 285-294) and CabbB-JI (Hull and Howell, 1987, Virology 86, 482-493); the 35S promoter described by Odell et al. (1985, Nature 313, 810-812) or in U.S. Pat. No. 5,164,316, promoters from the ubiquitin family (e.g. the maize ubiquitin promoter of Christensen et al., 1992, Plant Mol. Biol. 18, 675-689, EP 0 342 926, see also Cornejo et al. 1993, Plant Mol. Biol. 23, 567-581), the gos2 promoter (de Pater et al., 1992 Plant J. 2, 834-844), the emu promoter (Last et al., 1990, Theor. Appl. Genet. 81, 581-588), Arabidopsis actin promoters such as the promoter described by An et al. (1996, Plant J. 10, 107), rice actin promoters such as the promoter described by Zhang et al. (1991, The Plant Cell 3, 1155-1165) and the promoter described in U.S. Pat. No. 5,641,876 or the rice actin 2 promoter as described in WO070067; promoters of the Cassava vein mosaic virus (WO 97/48819, Verdaguer et al. 1998, Plant Mol. Biol. 37, 1055-1067), the pPLEX series of promoters from Subterranean Clover Stunt Virus (WO 96/06932, particularly the S7 promoter), a alcohol dehydrogenase promoter, e.g., pAdh1S (GenBank accession numbers X04049, X00581), and the TR1' promoter and the TR2' promoter (the "TR1'promoter" and "TR2'promoter", respectively) which drive the expression of the 1' and 2' genes, respectively, of the T-DNA (Velten et al., 1984, EMBO J 3, 2723-2730), the Figwort Mosaic Virus promoter described in U.S. Pat. No. 6,051,753 and in EP426641, histone gene promoters, such as the Ph4a748 promoter from Arabidopsis (PMB 8: 179-191), or others.

Alternatively, a promoter can be utilized which is not constitutive but rather is specific for one or more tissues or organs of the plant (tissue preferred/tissue specific, including developmentally regulated promoters). For example, a promoter active in leaf tissue or aerial plant parts, or epidermis specific promoters or guard cell specific promoters may be used.

Epidermal specific promoters, such as for example the Arabidopsis LTP1 promoter (Thoma et al, 1994, Plant Physiol. 105(1):35-45), the CER1 promoter (Aarts et al 1995. Plant Cell. 7:2115-27), and the CER6 promoter (Hooker et al 2002, Plant Physiol 129:1568-80) and the orthologous tomato LeCER6 (Vogg et al, 2004, J. Exp Bot. 55: 1401-10), provide specific expression in above ground epidermal surfaces.

Also suitable are leaf or photosynthetic tissue specific promoters, such as the light inducible ribulose 1,5-bisphosphate carboxylase small subunit promoter (Pssu) from Arabidopsis as described in U.S. Pat. No. 5,034,322 or from sunflower, from pea (U.S. Pat. No. 5,254,799) or from Zea mays; the potato ST-LS1 promoter which is stem and leaf specific (Stockhaus et al. 1987, Nucleic Acids Res. 15(8): 3479-91); the promoter of the chlorophyll a/b binding protein (CAB).

Guard cell specific promoters, such as the DGP1 promoter (Li et al., Sci China C Life Sci. 2005 48(2):181-6) may be used or drought-stress inducible promoters like RD29 (Yamaguchi-Shinozaki and Shinozaki 1993, supra), which is active in almost all the organs and tissues of vegetative plants during water deficiency.

The skilled person can easily test various promoters for their specificity and suitability in the methods according to the invention. In addition, the specificity of promoters may be modified by deleting, adding or replacing parts of the promoter sequence. Such modified promoters can be operably linked to reporter genes in order to test their spatiotemporal activity in transgenic plants.

Another alternative is to use a promoter whose expression is inducible. Examples of inducible promoters are chemical inducible promoters, such as dexamethasone as described by Aoyama and Chua (1997, Plant Journal 11: 605-612) and in U.S. Pat. No. 6,063,985 or by tetracycline (TOPFREE or TOP 10 promoter, see Gatz, 1997, Annu Rev Plant Physiol Plant Mol Biol. 48: 89-108 and Love et al. 2000, Plant J. 21: 579-88). Other inducible promoters are for example inducible by a change in temperature, such as the heat shock promoter described in U.S. Pat. No. 5,447,858, by anaerobic conditions (e.g. the maize ADH1S promoter), by light (U.S. Pat. No. 6,455,760), by pathogens (e.g. EP759085 or EP309862) or by senescence (SAG12 and SAG13, see U.S. Pat. No. 5,689,042) or by drought (see above). Obviously, there are a range of other promoters available. Examples of other inducible promoters are the Adh1 promoter which is inducible by hypoxia or cold stress, the Hsp70 promoter which is inducible by heat stress, and the PPDK promoter which is inducible by light. One preferred promoter is the ethanol-inducible promoter system, as described in Ait-ali et al. (2001, Plant Biotechnology Journal 1, 337-343), wherein ethanol treatment activates alcR, which in turn induces expression of the alc:35S promoter. See also Deveaux et al. (2003, The ethanol switch: a tool for tissue-specific gene induction during plant development. Plant J. 36, 918-930).

Optionally, the promoter-SlPP2C1 RNAi gene may further comprise a 3' end transcription regulation signals ("3' end" or "3' UTR") (i.e. transcript formation and polyadenylation signals). Polyadenylation and transcript formation signals include those of the nopaline synthase gene ("3' nos") (Depicker et al., 1982 J. Molec. Appl. Genetics 1, 561-573), the octopine synthase gene ("3' ocs") (Gielen et al., 1984, EMBO J 3, 835-845) and the T-DNA gene 7 ("3' gene 7") (Velten and Schell, 1985, Nucleic Acids Research 13, 6981-6998), which act as 3'-untranslated DNA sequences in transformed plant cells, and others.

The chimeric SlPP2C1 silencing gene (i.e. the promoter operably linked to a nucleic acid sequence which upon transcription in a plant cell is capable of silencing the endogenous SlPP2C1 gene expression) can be stably inserted in a conventional manner into the nuclear genome of a single plant cell, and the so-transformed plant cell can be used in a conventional manner to produce a transformed plant that has an altered phenotype due to SlPP2C1 silencing in certain cells at a certain time. In this regard, a T-DNA vector, comprising a promoter operably linked to a sense and/or antisense SlPP2C1 sequence (and optionally a 3' UTR), may be introduced into *Agrobacterium tumefaciens* and used to transform the plant cell, and thereafter, a transformed plant can be regenerated from the transformed plant cell using the procedures described, for example, in EP 0 116 718, EP 0 270 822, PCT publication WO84/02913 and published European Patent application EP 0 242 246 and in Gould et al. (1991, Plant Physiol. 95, 426-434). The construction of a T-DNA vector for *Agrobacterium* mediated plant transformation is well known in the art. The T-DNA vector may be either a binary vector as described in EP 0 120 561 and EP 0 120 515 or a co-integrate vector which can integrate into the *Agrobacterium* Ti-plasmid by homologous recombination, as described in EP 0 116 718.

Preferred T-DNA vectors each contain a promoter operably linked to SlPP2C1 silencing gene between T-DNA border sequences, or at least located to the left of the right border sequence. Border sequences are described in Gielen et al. (1984, EMBO J 3, 835-845). Of course, other types of vectors can be used to transform the plant cell, using procedures such as direct gene transfer (as described, for example in EP 0 223 247), pollen mediated transformation (as described, for example in EP 0 270 356 and WO85/01856), protoplast transformation as, for example, described in U.S. Pat. No. 4,684,611, plant RNA virus-mediated transformation (as described, for example in EP 0 067 553 and U.S. Pat. No. 4,407,956), liposome-mediated transformation (as described, for example in U.S. Pat. No. 4,536,475), and other methods such as those described methods for transforming certain lines of corn (e.g., U.S. Pat. No. 6,140,553; Fromm et all, 1990, Bio/Technology 8, 833-839; Gordon-Kamm et al., 1990, The Plant Cell 2, 603-618) and rice (Shimamoto et al., 1989, Nature 338, 274-276; Datta et al. 1990, Bio/Technology 8, 736-740) and the method for transforming monocots generally (PCT publication WO92/09696). For cotton transformation see also WO 00/71733, and for rice transformation see also the methods described in WO92/09696, WO94/00977 and WO95/06722. For *sorghum* transformation see e.g. Jeoung J M et al. 2002, Hereditas 137: 20-8 or Zhao Z Y et al. 2000, Plant Mol Biol. 44:789-98). For tomato or tobacco transformation see also An G. et al., 1986, Plant Physiol. 81: 301-305; Horsch R. B. et al., 1988, In: Plant Molecular Biology Manual A5, Dordrecht, Netherlands, Kluwer Academic Publishers. pp 1-9; Koornneef M. et al., 1986, In: Nevins D. J. and R. A. Jones, eds. Tomato Biotechnology, New York, N.Y., USA, Alan R. Liss, Inc. pp 169-178). For potato transformation see e.g. Sherman and Bevan (1988, Plant Cell Rep. 7: 13-16). Tomato transformation and regeneration can also be carried out according to De Jong et al. (2008) Plant Journal 57:160-170 and Sun et al. (2006) Plant Cell Physiol. 47: 426-431.

Likewise, selection and regeneration of transformed plants from transformed cells is well known in the art. Obviously, for different species and even for different varieties or cultivars of a single species, protocols are specifically adapted for regenerating transformants at high frequency.

Besides transformation of the nuclear genome, also transformation of the plastid genome, preferably chloroplast genome, is included in the invention. One advantage of plastid genome transformation is that the risk of spread of the transgene(s) can be reduced. Plastid genome transformation can be carried out as known in the art, see e.g. Sidorov V A et al. 1999, Plant J. 19: 209-216 or Lutz K A et al. 2004, Plant J. 37(6):906-13.

Any plant may be a suitable host, such as monocotyledonous plants or dicotyledonous plants, but most preferably plants which would benefit from being drought tolerant, such as but not limited to: tomato, pepper, cucumber, aubergine lettuce, artichoke, leek, melon, watermelon, carrot, *Brassicas* (*B. oleracea, B. napus, B. juncea*), onion, lamb's lettuce, artichoke, potato, spinach, grape, pea, beans, soybean, and many others.

Preferred hosts are of the family Solanaceae, such as species of the genus *Solanum*, e.g. tomato (*S. lycopersicum*), tree tomato (*S. betaceum*, syn. *Cyphomandra betaceae*) and other *Solanum* species, such as aubergine/eggplant (*Solanum melongena*), potato (*Solanum tuberosum*), pepino (*S. muricatum*), cocona (*S. sessiliflorum*) and naranjilla (*S. quitoense*). The family Solanaceae also includes peppers (*Capsicum annuum, Capsicum frutescens*).

In a preferred embodiment the host is of the family Solanaceae. In a more preferred embodiment the host is of the genus *Solanum*. In an even more preferred embodiment the host is of the species *S. lycopersicum*. Preferably, the host is a cultivated tomato of the species *S. lycopersicum*, i.e. a line or variety yielding high yields, such as fruit of at least 50 g average fresh weight or more, e.g. at least about 80 g, 90 g, 100 g, 200 g, 300 g, or even up to 600 g (beef tomato types). Also small types, such as cherry or cocktail tomato are encompassed, as are full-flesh tomatoes such as the Nunhems variety Intense, e.g. lacking gel in the seed cavities. The host tomato plant may be determinate or indeterminate, of various fruit sizes and shapes, such as Roma type, cluster type, round. It may be a processing type tomato or a fresh market type. Also both open pollinated and hybrids are encompassed herein. In one embodiment the drought tolerant tomato plant is an F1 hybrid plant, grown from an F1 hybrid seed. To make F1 hybrid seeds of a transgenic plant according to the invention, two inbred parent lines may be made, each comprising a copy of the transgene in their genomes. When these plants are cross-fertilized, the F1 seeds are collected, which produce transgenic F1 hybrid plants with high yield and drought tolerance due to the transgene.

The embodiments described herein for 'host' plants also apply to non-transgenic mutant plants described elsewehere herein, whereby instead of a transgene a mutant SlPP2C1 allele is present endogenously.

Other suitable hosts are other vegetable species and various species bearing fleshy fruits (grapes, peaches, plums, strawberry, mango, papaya, etc.). Also Cucurbitaceae, such as melon (*Citrullus lanatus, Cucumis melo*) and cucumber (*Cucumis sativus*) and squashes and marrows (*Cucurbita*) are suitable hosts. Likewise Rosaceae are suitable hosts, such as apple, pear, plum, etc.

Also field crops with enhanced drought tolerance are provided according to the invention. For example maize/corn (*Zea* species, e.g. *Z. mays, Z. diploperennis* (chapule), *Zea luxurians* (Guatemalan teosinte), *Zea mays* subsp. *huehuetenangensis* (San Antonio Huista teosinte), *Z. mays* subsp. *mexicana* (Mexican teosinte), *Z. mays* subsp. *parviglumis* (Balsas teosinte), *Z. perennis* (perennial teosinte) and *Z. ramosa*), wheat (*Triticum* species), barley (e.g. *Hordeum vulgare*), oat (e.g. *Avena sativa*), sorghum (*Sorghum bicolor*), rye (*Secale cereale*), soybean (*Glycine* spp, e.g. *G. max*), cotton (*Gossypium* species, e.g. *G. hirsutum, G. barbadense*), *Brassica* spp. (e.g. *B. napus, B. juncea, B. oleracea, B. rapa*, etc), sunflower (*Helianthus annus*), tobacco (*Nicotiana* species), alfalfa (*Medicago sativa*), rice (*Oryza* species, e.g. *O. sativa indica* cultivar-group or *japonica* cultivar-group), forage grasses, pearl millet (*Pennisetum* spp. e.g. *P. glaucum*).

Other hosts include ornamental species (e.g. *Rose, Petunia, Chrysanthemum, Lily, Gerbera* species), woody trees (e.g. species of *Populus, Salix, Quercus, Eucalyptus*), fibre species e.g. cotton, flax (*Linum usitatissimum*) and hemp (*Cannabis sativa*).

Basically, any crop plant species is suitable. A crop plant or cultivated plant refers herein to a plant species which is cultivated and bred by humans and excludes weeds such as *Arabidopsis thaliana*, or wild relatives, such as the tomato relatives *Solanum pennellii, Solanum chilense, Solanum chmielewskii, Solanum habrochaites, Solanum pimpinellifolium* and others (although mutant SlPP2C1 alleles may be derived from such plants and transferred into cultivated tomato by breeding methods, see further down). A crop plant may be cultivated for food purposes (e.g. vegetable crops or field crops), or for ornamental purposes (e.g. production of flowers for cutting, grasses for lawns, etc.). A crop plant as defined herein also includes plants from which non-food products are harvested, such as oil for fuel, plastic polymers, pharmaceutical products, cork, fibers and the like.

Thus, in one embodiment of the invention transgenic plants comprising a transcription regulatory element (especially a promoter as described above) operably linked to nucleic acid molecule which upon transcription is capable of silencing the endogenous SlPP2C1 gene expression in the host cells.

The construction of chimeric genes and vectors for, preferably stable, introduction of SlPP2C1 silencing gene into the genome of host cells is generally known in the art. To generate a chimeric gene the sense and/or antisense SlPP2C sequence is operably linked to a promoter sequence, suitable for expression in the host cells, using standard molecular biology techniques. The promoter sequence may already be present in a vector so that the nucleic sequence is simply inserted into the vector downstream of the promoter sequence. The vector is then used to transform the host cells and the chimeric gene is inserted in the nuclear genome or into the plastid, mitochondrial or chloroplast genome and expressed there using a suitable promoter (e.g., Mc Bride et al., 1995 Bio/Technology 13, 362; U.S. Pat. No. 5,693,507).

The resulting transformed plant can be used in a conventional plant breeding scheme to produce more transformed plants with the same characteristics or to introduce the gene in part into other varieties of the same or related plant species. An "elite event" can be selected, which is a transformation event having the transgene inserted in a particular location in the genome, which results in good expression of the desired phenotype (e.g. optimal silencing and drought tolerance).

In one embodiment of the invention it is desired to enhance water loss, i.e. to decrease drought tolerance of specific tissues and/or to decrease ABA sensitivity of specific tissues, for example fruits, by overexpressing SlPP2C1 in at least such tissues. For example, to achieve fruits (e.g. tomatoes) with an increased water loss and therefore a more solid fruit flesh and/or enhanced taste, a fruit specific or fruit preferred promoter is suitable, operably linked to a nucleic acid sequence encoding a functional SlPP2C protein (SEQ ID NO: 2 or a variant thereof). To confer expression to fruits, a tomato fruit and peel specific promoter e.g. beta-galactosidase II (Smith et al., 1998, Plant Physiol 117: 417-23) or tomato epicuticular wax promoter LeCER6 (Vogg et al, 2004, supra) can be used. Or a fruit skin or epidermal promoter can be identified and isolated by one skilled in the art, using microarrays and confirmation by transformation of promoter reporter gene fusions. Such promoters can also be used for SlPP2C1 silencing in specific tissues, such as fruits.

The transgenic plants, or parts thereof, in which SlPP2C1 is silenced, have significantly enhanced drought tolerance. Significantly enhanced drought tolerance (as described above) is used herein to refer to an enhanced ability of transformants (compared to wild type or control transformants) to tolerate one or more periods of drought (water deprivation/depletion leading to e.g. visible leaf wilting symptoms in control plants), as described above. Preferably, the plants are able to recover subsequently, thereby leading to a reduced overall yield loss, as more plants per $m^2$ survive and/or the yield of the surviving plants is not significantly reduced.

Significantly enhanced drought tolerance can be assessed in controlled environments (green house or growth chambers) as described above or using equivalent methods. For example, an alternative method is the following: at least about 10 transformants per transformation event and at least 10 control plants are placed for various time periods (ranging from a few hours to 1-4 weeks or more) into the environment without watering them, until leaf wilting or loss of turgor is caused on control plants, and subsequently watering the plants again for e.g. at least 1 week, 2 weeks or longer, while their recovery phenotype is analyzed. Transformants with enhanced drought tolerance survive at least 2, 3, 4, 5, 6, 7 days, preferably at least 2-5 days longer without water than control-transformants (e.g. transformed with an empty vector) or wild type plants do under the same conditions, and which show irreversible tissue damage. Alternatively, % survival can be calculated at a certain timepoint, whereby the drought tolerant plants have a % survival which is at least 10%, 20%, 30%, or more, higher than that of the control. This alternative method may also be used for determining whether mutant plants (i.e. non-transgenic plants comprising one or more mutant SlPP2C1 alleles) have significantly enhanced drought tolerance. It is understood that when mutant plants are analyzed for their phenotype, the control plants are preferably near isogenic lines of the mutant, which comprise the wild type allele(s). The period of water deprivation/stress and the period of recovery may vary depending on the plant species. For example, in rice 9.5 hours water stress followed by 10 days of recovery (watering) are suitable for determining whether a plant line or transformation event has enhanced drought tolerance compared to the control, as the percentage survival is significantly increased in the drought tolerant line (see e.g. Zheng et al. Biochemical and Biophysical Research Communications 2009, 985-989).

Ultimately, field trials are used to show that transformants (or mutant plants described further down) have significantly enhanced drought tolerance compared to wild type plants.

As already mentioned, transformants having an optimal silencing level can be selected by e.g. analysing copy number (Southern blot analysis), mRNA transcript levels (e.g. RT-PCR using SlPP2C1 primer pairs) or by analysing the presence and/or level of SlPP2C1 protein in various tissues (e.g. SDS-PAGE; ELISA assays, etc). Optimal transgenic events are then used for further crossing/backcrossing/selfing until a high performing elite event with a stable transgene is obtained. In one embodiment especially the transgenic seeds derived from such plants are provided, which may be sold as being "drought tolerant".

Transformants expressing one or more SlPP2C1 genes according to the invention may also comprise other transgenes, such as other genes conferring drought tolerance or conferring tolerance to other biotic or abiotic stresses. To obtain such plants with "stacked" transgenes, other transgenes may either be introgressed into the SlPP2C1 transformants, or the transformants may be transformed subsequently with one or more other genes, or alternatively several chimeric genes may be used to transform a plant line or variety. For example, several chimeric genes may be present on a single vector, or may be present on different vectors which are co-transformed.

In one embodiment the following genes are combined with SlPP2C1 silencing according to the invention: Genes encoding other AP2/EREBP type transcription factors, preferably ones which have a role in the plant's response to environmental stresses, such as for example the CBF1, CBF2, CBF3 and/or CBF4 encoding genes from *Arabidopsis* (Jaglo-Ottosen et al 1998, Science 280, 104-106, 1998; Kasuga et al 1999 Nat. Biotechnol. 17, 287-291) or orthologs thereof from other species (Dubouzet et al 2003, Plant J. 33: 751), with insect resistance genes such as *Bacillus thuringiensis* toxin genes (encoding insecticidal proteins, such as cry genes, vip genes, etc. see http://www.biols.susx.ac.uk/home/ for a list of available genes), fungal resistance genes, herbicide resistance genes, or other genes.

The stacked transformants may thus have an even broader environmental stress tolerance, to for example salinity, cold stress, insect resistance, pathogen resistance, heat stress, water stress, etc.

Whole plants, seeds, cells, tissues and progeny (such as F1, F2 seeds/plants, etc) of any of the transformed plants described above are encompassed herein and can be identified by the presence of the transgene in the DNA, for example by PCR analysis. Also "event specific" PCR diagnostic methods can be developed, where the PCR primers are based on the plant DNA flanking the inserted chimeric gene, see U.S. Pat. No. 6,563,026. Similarly, event specific AFLP fingerprints or RFLP fingerprints may be developed which identify the transgenic plant or any plant, seed, tissue or cells derived therefrom.

It is understood that the transgenic plants according to the invention preferably do not show non-desired phenotypes, such as yield reduction, less fruits per plant, enhanced susceptibility to diseases or undesired architectural changes (dwarfing, deformations) etc. and that, if such phenotypes are seen in the primary transformants, these can be removed by normal breeding and selection methods (crossing/backcrossing/selfing, etc.). Any of the transgenic plants described herein may be homozygous or hemizygous for the transgene.

Non-Transgenic Drought Tolerant Plants and Methods for Making these

It is also an embodiment of the invention to use non-transgenic methods, e.g. target mutant generation and identification systems such as TILLING (Targeting Induced Local Lesions IN Genomics; McCallum et al., 2000, Nat Biotech 18:455, and McCallum et al. 2000, Plant Physiol. 123, 439-442, Henikoff et al. 2004, Plant Physiol. 135: 630-636 incorporated herein by reference) and selection to generate plant lines which comprise at least one mutation in an endogenous SlPP2C1 allele and whereby the plants comprising the mutant SlPP2C1 allele in heterozygous or homozygous form have significantly enhanced drought tolerance and/or a significantly enhanced sensitivity to ABA compared to plants lacking the mutant allele (having wild type allele(s) at the SlPP2C1 locus). Thus, in one embodiment of the invention plants comprising one or more mutant SlPP2C1 alleles in the genome and having significantly enhanced drought tolerance compared to plants lacking said mutant allele(s), but comprising wild type alleles instead, are provided herein, as well as plant parts (e.g. harvested fruit, harvested leaves, etc.), seeds, clonal propagations of such plants, progeny of such plants comprising the mutant allele.

A "significantly reduced sensitivity to water stress" or "significantly enhanced drought tolerance" refers to a (statistically significant) reduced leaf wilting symptoms of a plurality of plants comprising the mutant allele(s) by at least 10% compared to control levels (e.g. same plants lacking the mutant allele, such as the non-mutated plants) and can for example be tested as described herein for transgenic plants or using equivalent alternative methods. In short, a plurality of mutant plants (preferably at least 10, 15, 20 or more plants of a line comprising a particular mutation in the SlPP2C1 allele) and controls of the same age are saturated with water at the start of the experiment and are then not watered for an extended period of time, e.g. 7, 8, 9, 10, 11, 12, 13, 14, 15 days or more. When the controls start to show wilting of the leaves ("slight wilting" or "moderate wilting"), all plants are assessed for signs of wilting of the leaves using e.g. visual assessment. Wilting symptoms of leaves can be scored on a scale of 1 to 4, as "highly wilted" (4), "moderate wilting" (3), "slightly wilted" (2) or "no wilting" (1), for example. Mutant plants are said to have a significantly enhanced drought tolerance if average wilting is reduced by at least 10%, preferably at least 20%, 30%, 40%, 50%, 60%, 70%, 80%, 90% or 100% compared to the wild type control plants. For example, if 10 plants are scored for wilting symptoms (w) per line, the control may have an average score of w=40/10=4.0, while the drought tolerant line may have an average score of w=36/10=3.6 or less, e.g. w=3.4, 3.2, 2.0, 1.4, or 1.0.

Alternatively or in addition field trials can be used to determine whether a significantly enhanced drought tolerance is conferred on the line by the mutant SlPP2C1 allele. For example, a plurality of plants comprising a particular mutant SlPP2C1 allele (preferably at least 10, 20, 30 or more plants of a line) are planted in the field together with control plants and not watered for an extended period of time, such as 1, 2, 3, 4 weeks or more. When the control plants show wilting, wilting symptoms may be assessed as described above. Alternatively % recovery and/or % survival after being supplied with water (recovery) may be assessed. When leaf wilting or loss of turgor is caused on control plants, plants are watered again (e.g. for 1 week, 2 weeks or more) while their recovery phenotype is analyzed. Mutants with enhanced drought tolerance survive at least 2, 3, 4, 5, 6, 7 days, preferably at least 2-5 days longer without water than control-plants (e.g. wild type or near isogenic lines) under the same conditions, and which show irreversible tissue damage. Similarly, % survival can be calculated, with the drought tolerant mutant plant line having a (average) % survival which is increased by at least 10%, 20%, 30%, or more, compared to that of the control.

As mentioned earlier, other assays for drought tolerance may be used. The most suitable assay may differ for different crop species, i.e. for tomato plants a different assay may be suitable than for lettuce or rice. For example a statistically significant increase in plants (comprising the mutant allele) recovering from a period of drought may be measured and/or a significantly reduced plant mortality after a period of drought may be measured in plants comprising the mutant allele compared to plants lacking it. See e.g. the methods described in Zheng et al. (2009, supra), Yu et al. (2008, supra) or Xiong et al. 2006 (supra).

"Significantly enhanced ABA sensitivity" can also be tested as described in the Examples for transgenic plants. In summary, average seed germination on medium comprising ABA is at least 10%, 20%, 30%, 40%, 50% or more lower for the plant comprising the SlPP2C1 mutant allele than for the control on the same ABA concentration. For example, on 1 or 3 µM ABA, 50% of wild type seeds germinate, while less than 40%, 35%, 30%, or less, of mutant seeds germinate. Thus, seed germination of plants comprising the mutant allele is inhibited more by ABA. Root growth of plants comprising the mutant allele is also inhibited more by ABA.

Preferably the plants phenotyped for drought tolerance and/or ABA sensitivity as described above are homozygous for the mutant SlPP2C1 allele, although heterozygous plants may also be phenotyped and may also show enhanced drought tolerance and/or enhanced ABA sensitivity. To generate plants comprising the mutant allele in homozygous form, selfing can be used, optionally combined with genotyping (detecting the presence of the mutant allele e.g. by PCR using allele specific primers and/or sequencing). If TILLING populations are used the mutant plants (M1) are preferably selfed one or more times to generate for example M2 populations or preferably M3 or M4 populations for phenotyping. In M2 populations the mutant allele is present in a ratio of 1 (homozygous for mutant allele):2 (heterozygous for mutant allele):1 (homozygous for wild type allele). Segregation of drought tolerance should correlate with segregation of the mutant allele.

The plant comprising the mutant SlPP2C1 allele, or a variant thereof, and having enhanced drought tolerance may be of any species, as the tomato sequences provided herein can be used to generate and identify plants comprising mutations in homologs and orthologs of the gene, as described further below. The endogenous SlPP2C1 variant nucleic acid sequence in the plant can be identified, which can then be used as target gene in the generation and/or identification of plants comprising a mutant allele of the SlPP2C1 variant. Thus, the mutant drought tolerant plant may be a dicotyledonous or monocotyledonous species. Preferably the plant is a cultivated plant, although it is also an embodiment herein to identify mutant alleles in wild plants or non-cultivated plants and transfer these by breeding techniques into cultivated plants.

In one embodiment, the plant comprising at least one mutant SlPP2C1 allele (in homozygous or heterozygous form) and having significantly enhanced drought tolerance (and/or significantly increased sensitivity to ABA), is of the family Solanaceae, i.e. encompassing the genera *Solanum, Capsicum, Nicotiana* and others. In another embodiment the plant is of the genus *Solanum*, e.g. encompassing cultivated tomato, potato, eggplant, and others.

In one embodiment, a drought tolerant potato plant comprises a mutant SlPP2C1 allele (e.g. StPP2C1 of SEQ ID NO: 14 or a variant thereof), encoding a reduced-function or loss of function protein (e.g. a reduced function or loss of function StPP2C1 protein of SEQ ID NO: 15 or a variant thereof).

In a specific embodiment the plant is of the species *S. lycopersicum*. Any *S. lycopersicum* may be generated and/or identified having at least one mutant SlPP2C1 allele in its genome and being drought tolerant. The tomato plant may, thus, be any cultivated tomato, any commercial variety, any breeding line or other, it may be determinate or indeterminate, open pollinated or hybrid, producing fruits of any shape and size. The mutant allele generated and/or identified in a particular tomato plant, or in a sexually compatible relative, may be easily transferred into any other tomato plant by breeding (crossing with a plant comprising the mutant allele and then selecting progeny comprising the mutant allele).

The plant may be any species of the family Solanaceae or of the genus *Solanum*, which species is either mutagenized itself to generate the mutant allele (e.g. by TILLING) or in which one or more natural or spontaneous mutations in the SlPP2C1 gene (or variant) is/are identified, e.g. by Ecotilling.

The mutant allele is in one embodiment generated or identified in a cultivated plant, but may also be generated and/or identified in a wild plant or non-cultivated plant and then transferred into an cultivated plant using e.g. crossing and selection (optionally using interspecific crosses with e.g. embryo rescue to transfer the mutant allele). Thus, a mutant SlPP2C1 allele may be generated (human induced mutation using mutagenesis techniques to mutagenize the target SlPP2C1 gene or variant thereof) and/or identified (spontaneous or natural allelic variation) in other *Solanum* species include for example *S. cheesmanii, S. chilense, S. habrochaites, S. chmielewskii, S. lycopersicum×S. peruvianum, S. glandulosum, S. hirsutum, S. minutum, S. parviflorum, S. pennellii, S. peruvianum, S. peruvianum* var. *humifusum* and *S. pimpinellifolium*, and then transferred into a cultivated *Solanum* plant, e.g. *Solanum lycopersicum* by traditional breeding techniques. The term "traditional breeding techniques" encompasses herein crossing, selfing, selection, double haploid production, embryo rescue, protoplast fusion, etc. as known to the breeder, i.e. methods other than genetic modification by which alleles can be transferred.

Preferably the mutation(s) in the SlPP2C1 allele cause(s) the plant to have a significantly enhanced drought tolerance and/or significantly enhanced ABA sensitivity compared to plants lacking the mutant allele(s) (i.e. comprising wild type SlPP2C1 alleles), as described above.

Without limiting the invention, the mutation in SlPP2C1 (SEQ ID NO: 1, or variants thereof, or in the corresponding genomic sequence, e.g. SEQ ID NO: 11 from nucleotides 2676 to 4975, or variants thereof), result in reduced functionality or loss-of function of the SlPP2C1 protein, for example through single base transition(s), mis-sense or non-sense mutations, or insertion or deletion of one or more amino acids or a frame-shift in the coding sequence, which in turn results in the changed phenotype. The presence and type of mutation(s) can be analyzed by sequencing the gene, using SlPP2C1 specific primers. A "significant reduction" of the SlPP2C1 protein's functionality is preferably determined indirectly in vivo by the phenotype (i.e. significantly enhanced drought tolerance) in plants heterozygous or, preferably, homozygous for the mutant allele. The drought tolerant phenotype co-segregates with the mutant allele. However, a "significant reduction" of the protein's functionality can also be determined in vitro by protein phosphatase assays, whereby the mutant SlPP2C1 protein phosphatase activity is reduced by at least 10, 20, 30, 40, 50, 60, 70, 80, 90 (reduced-function) or 100% (loss of function mutation). To do this, the mutant allele is cloned and expressed e.g. in E. coli, followed by an in vitro phosphatase assay as for example described by Gosti et al. 1999, Plant Cell 11: 1897-1910, Material and Methods—PP2C Activities, page 1907.

In one embodiment of the invention a plant (preferably a tomato plant) is provided, which comprises one or more mutations in SEQ ID NO:1 or SEQ ID NO: 11 (from nucleotides 2676 to 4975), or in a nucleic acid sequence comprising at least about 45%, 50%, 60%, 70%, 80%, 90%, 95%, 98%, 99% or more sequence identity to SEQ ID NO: 1 (as defined) or to SEQ ID NO: 11 (from nucleotides 2676 to 4975), or in the corresponding genomic sequence of any one of these, whereby the mutation results in the encoded SlPP2C1 protein (or variant) having reduced activity (compared to the wild type functional protein) or no activity in vivo and/or in vitro and wherein said plant comprises significantly enhanced drought tolerance compared to a plant (preferably tomato) comprising a nucleic acid sequence encoding a wild type SlPP2C1 protein (or variant).

In one embodiment a plant (preferably a tomato plant) is provided, which comprises one or more mutations in the nucleotide sequence encoding the protein of SEQ ID NO: 2, or a protein comprising at least 45%, 50%, 60%, 70%, 80%, 85%, 90%, 95%, 98%, 99% or more sequence identity to SEQ ID NO: 2 (as defined), and wherein the (tomato) plant comprises significantly enhanced drought tolerance compared to a (tomato) plant lacking said one or more mutations.

In one embodiment a drought tolerant plant (preferably a tomato plant) comprising a mutant SlPP2C1 allele is provided, characterized in that the mutation is a loss-of-function or reduced-function mutation of the encoded SlPP2C1 protein, said protein being a protein comprising at least 45%, 48%, 49%, 50%, 60%, 70%, 80%, 85%, 90%, 95%, 98%, 99% or more amino acid sequence identity to SEQ ID NO: 2.

The plant (e.g. the tomato plant) is preferably homozygous for the mutant SlPP2C1 allele.

Mutant plants can be distinguished from non-mutants by molecular methods, such as the mutation(s) present in the SlPP2C1 genomic DNA or mRNA (cDNA), SlPP2C1 protein levels and/or protein activity, etc., and by the modified phenotypic characteristics compared to the wild type. The mutant allele can be transferred into other plants which are sexually compatible with the mutant plant using traditional crossing and selection. Thus, the mutant allele can be used to generate drought tolerant tomato varieties of any type, e.g. open pollinate varieties, hybrid varieties, F1 hybrids, Roma type, cherry type, determinate or indeterminate types, etc. In one embodiment the plant (preferably S. lycopersicum) comprising the mutant SlPP2C1 allele and having enhanced drought tolerance is an F1 hybrid plant or a F1 seed, from which an F1 hybrid plant is grown. The inbred parents used to make the F hybrid preferably both comprise the same mutant SlPP2C1 allele in their genome in homozygous form.

In another embodiment, the plant comprising the mutant SlPP2C1 allele (e.g. tomato) is crossed with another plant of the same species or of a closely related species, to generate a hybrid plant (hybrid seed) comprising the mutant SlPP2C1 allele. Such a hybrid plant is also an embodiment of the invention. Also a method for transferring a mutant SlPP2C1 allele to another plant is provided, comprising providing a plant comprising a mutant SlPP2C1 allele in its genome, crossing said plant with another plant and obtaining the seeds of said cross. Optionally plants obtained from these seeds may be further selfed and/or crossed and progeny selected comprising the mutant allele and having enhanced drought tolerance.

In one embodiment, the parents used to make the F1 hybrid comprise different mutant SlPP2C1 alleles in homozygous form, so that the hybrid comprises two different mutant SlPP2C1 alleles. For example, parent 1 may comprise loss-of-function mutant while parent 2 comprises a reduced-function mutant. The F1 hybrid then comprises one allele from each parent. Thus, also tomato plants comprising two different mutant SlPP2C1 alleles at the SlPP2C1 locus and having enhanced drought tolerance are provided herein.

Plants comprising a mutant SlPP2C1 allele, encoding a loss-of-function or reduced-function protein (e.g. a truncated protein as a result of a non-sense mutation, a protein having a modified amino acid sequence, resulting e.g. in a modified catalytic site, a modified folding, etc., for example due to a mis-sense mutation, frame-shift mutation and/or a splice site mutation), can be generated and/or identified by using mutagenesis methods or by screening natural populations for natural variants in the SlPP2C1 allele. In one embodiment of the invention TILLING is used to generate such plants and/or to identify such mutagenesis induced mutations and/or EcoTILLING is used to identify plants, such as wild plants or non-cultivated plants, comprising natural (spontaneous) mutations in the SlPP2C1 gene, which can then be transferred into cultivated plants by traditional breeding techniques. However, any other mutagenesis method may be used and it is understood that both human induced mutants, UV or X-ray mutagenesis, chemical mutagens etc. and spontaneous mutants of the SlPP2C1 gene generated in or transferred into cultivated plants or crop plants by traditional breeding are encompassed herein.

In one specific embodiment according to the invention the drought tolerant mutant plant is a plant of a different species than tomato, e.g. a monocotyledonous cultivated plant, preferably a rice, maize, wheat or barley plant comprising a mutant SlPP2C1 allele in its genome. When using methods such as TILLING, the amplification of the target gene fragment may be based on SEQ ID NO: 1, or fragments thereof (e.g. using specific or degenerate primers, for example designed based on one or more of the conserved domains of SlPP2C1), or one may first isolate the SlPP2C1 ortholog and base primer design on the orthologous sequence.

TILLING (Targeting Induced Local Lesions IN Genomes) is a general reverse genetic technique that uses traditional chemical mutagenesis methods to create libraries of mutagenized individuals that are later subjected to high throughput screens for the discovery of mutations. TILLING combines chemical mutagenesis with mutation screens of pooled PCR products, resulting in the isolation of mis-sense and non-sense mutant alleles of the targeted genes. Thus, TILLING uses traditional chemical mutagenesis (e.g. EMS or MNU mutagenesis) or other mutagenesis methods (e.g. radiation such as UV) followed by high-throughput screening for mutations in specific target genes, such as SlPP2C1 according to the invention. S1 nucleases, such as CEL1 or ENDO1, are used to cleave heteroduplexes of mutant and wildtype target DNA and detection of cleavage products using e.g. electrophoresis such as a LI-COR gel analyzer system, see e.g. Henikoff et al. Plant Physiology 2004, 135: 630-636. TILLING has been applied in many plant species, such as tomato (see http://tilling.ucdavis.edu/index.php/Tomato_Tilling), rice (Till et al. 2007, BMC Plant Biol 7: 19), *Arabidopsis* (Till et al. 2006, Methods Mol Biol 323: 127-35), *Brassica*, maize (Till et al. 2004, BMC Plant Biol 4: 12), etc. Also EcoTILLING, whereby mutants in natural populations are detected, has been widely used, see Till et al. 2006 (Nat Protoc 1: 2465-77) and Comai et al. 2004 (Plant J 37: 778-86). In one embodiment herein, classical TILLING is modified and instead of using enzyme based mutant detection (enzymatic digestion with a single-strand specific nuclease and high resolution polyacrylamide gel electrophoresis), two different high throughput detection systems can be used which have previously obly been used in humans. These detection protocols are adaptations of CSCE (Conformation Sensitive Capillary Electrophoresis, see Rozycka et al. 2000, Genomics 70, 34-40) or of HRM (High Resolution Melting, see Clin Chem 49, 853-860). See also the Examples. Thus, non-transgenic plants, seeds and tissues comprising a mutant SlPP2C1 allele in one or more tissues and comprising one or more of the phenotypes conferred by a reduced-function or loss-of-function SlPP2C1 protein according to the invention (e.g. enhanced drought tolerance as described above) and methods for generating and identifying such plants is encompassed herein.

Also a method for generating and/or identifying a mutant SlPP2C1 allele suitable for generating drought tolerant plants and/or a method for generating a plant comprising enhanced drought tolerance is provided, comprising the steps of:
  (a) mutagenizing plant seeds (e.g. by EMS mutagenesis) to generate an M1 population or providing mutagenized plant seeds or providing plants comprising natural variation,
  (b) optionally selfing the plants of (a) one or more times to generate an M2, M3 or M4 families,
  (c) preparing DNA of the plants of (a) or (b) and pooling DNA of individuals,
  (d) PCR amplification of all or part of the SlPP2C1 target gene (genomic or cDNA), or a variant thereof, from the DNA pools,
  (e) detecting the presence of mutated SlPP2C1 allele(s) in the PCR amplification products and thereby also in the DNA pools,
  (f) selecting the corresponding individual plants comprising the mutant SlPP2C1 allele(s),
  (g) optionally sequencing the mutant SlPP2C1 allele of the plant;
  (h) phenotyping the plants of (f), or progeny thereof, for drought tolerance and/or ABA sensitivity, and
  (i) selecting drought tolerant plants, and optionally
  (j) breeding with the plant of (i) to generate cultivated a drought tolerant plant having good agronomic characteristics.

Step (a) may also be simply providing such plants.

In step (c) alternatively plant tissue may be pooled and DNA isolated from the pooled tissue samples, to provide a DNA pool of different individuals.

In step (d) primers which amplify all or part of the target gene, SlPP2C1 (SEQ ID NO: 1) or a variant thereof, are designed using standard methods, such as CODDLE (http://www.proweb.org/doddle) Primers may be designed to amplify e.g. at least about 100, 200, 250, 300, 400, 500, 600, 800 bp or at least about 1000 bp or more of the target gene, i.e. of SEQ ID NO: 1, or of a variant of SEQ ID NO: 1, or of the genomic sequence of SEQ ID NO: 1 (i.e. further comprising introns, e.g. for tomato SEQ ID NO:11 from nucleotides 2676-4975). The genomic sequence can be easily isolated and its sequence determined as described in the Examples. Preferably a fragment comprising all or part of a conserved domain of the SlPP2C1 protein is amplified by the primer, e.g. the C-terminal domain or the putative magnesium binding domain described.

For plant species other than tomato, it may be desirable to first identify the sequence of the endogenous SlPP2C1 gene in order to be able to design good primer sequences. The sequence may be identified in silico or by, for example, designing degenerate PCR primers and amplifying all or part of the SlPP2C1 gene variant (ortholog of the tomato SlPP2C1 gene) from the genome of the plant species. The sequence of the endogenous SlPP2C1 gene is then preferably used to design suitable primers for TILLING.

Step (e) may make use of S1 nucleases, such as CEL1, to detect mismatches between the PCR amplification product, i.e. between the wild type SlPP2C1 PCR product and the mutant SlPP2C1 PCR product which form heteroduplexes. Alternatively, step (e) may use CSCE or HRM for detection. In CSCE homoduplexes (WT/WT or mutant/mutant fragments) are formed and heteroduplexes (mutan/WT fragments). Because of the mismatch formed, heteroduplexes migrate at a different speed than the homoduplexes through capillaries, thus allowing the identification of pools containing a mutation within the target fragment. HRM is also a non-enzymatic technique. During the PCR amplification of the target gene fragments LCgreen Plus+TM molecules are incorporated between each annealed base pair of the double stranded DNA molecule, which—when captured in the molecule—will emit fluorescence. A LightScanner records the fluorescence intensity while the plate is progressively heated. At a certain temperature the PCR products start to melt and release the LCgreen Plus+TM, whereby fluorescence decreases. DNA pools containing a mutation (heteroduplexes) are identified because their melting temperature is lower than that of homoduplexes.

Step (j) may involve traditional breeding methods and phenotypic and/or marker assisted selection methods. Many different drought tolerant varieties can be generated this way.

Extensive protocols for carrying out TILLING have been published, see e.g. http://blocks.fhcrc.org/%7Esteveh/TILLING_publications.html and Till et al. (2006) Nature Protocols 1:2465-2477; Till et al. (2006) Methods Mol Biol. 323:127-135 and Till et al. (2003) Methods Mol Biol. 236:205-220, all incorporated herein by reference.

Once a plant comprising a mutant allele which confers the desired phenotype has been identified, this allele can be transferred to other plants by traditional breeding techniques, e.g. by crossing the plant with another plant and collecting progeny of the cross. In step (j) the allele may thus be used to generate plants which are drought tolerant and which provide good agronomic characteristics.

As mentioned, it is understood that other mutagenesis and/or selection methods may equally be used to generate mutant plants according to the invention. Seeds may for example be radiated or chemically treated to generate mutant populations. Also direct gene sequencing of SlPP2C1 may be used to screen mutagenized plant populations for mutant alleles. For example KeyPoint screening is a sequence based method which can be used to identify plants comprising mutant SlPP2C1 alleles (Rigola et al. PloS One, March 2009, Vol 4(3):e4761).

Thus, non-transgenic mutant plants which produce lower levels of (functional) wild type SlPP2C1 protein in one or more tissues (particularly at least in leaf tissue) are provided, or which completely lack functional SlPP2C1 protein in specific tissues or which produce a non-functional SlPP2C1 protein in certain tissues, e.g. due to mutations in one or more endogenous SlPP2C1 alleles. These mutants may be generated by mutagenesis methods, such as TILLING or variants thereof, or they may be identified by EcoTILLING or by any other method. SlPP2C1 alleles encoding non-functional or reduced-functional SlPP2C1 protein may be isolated and sequenced or may be transferred to other plants by traditional breeding methods.

In one embodiment a plant having enhanced drought tolerance due to the mutant allele of tomato plants 2, 3, 5, 7 or 10 of Example 4 being present in the genome is provided herein, and progeny and parts thereof comprising the allele.

Any part of the plant, or of drought tolerant progeny thereof, is provided, including harvested fruit, harvested tissues or organs, seeds, pollen, flowers, etc.

Also provided are kits for detecting whether or not a plant comprises a mutant SlPP2C1 allele according to the invention. Such a kit may comprise PCR primers or probes detection of the allele in a tissue sample.

Plant (and corresponding seed) comprising one or more mutant SlPP2C1 alleles according to the invention may be marketed and/or labelled as having (enhanced) "drought tolerance" or as being "drought resistant".

Preferably, the drought tolerant mutant plants also have good other agronomic characteristics, i.e. they do not have reduced fruit numbers and/or reduced yield compared to wild type plants and/or product quality is not reduced. Preferably yield and/or survival rate of such plants is higher under both long term and/or short term drought stress. In a preferred embodiment the plant is a tomato plant and the fruit is a tomato fruit, such as a processing tomato, fresh market tomato of any shape or size or colour. Thus, also harvested products of plants or plant parts comprising one or two mutant SlPP2C1 alleles are provided. This includes downstream processed products, such as tomato paste, ketchup, tomato juice, cut tomato fruit, canned fruit, dried fruit, peeled fruit, etc. The same applies for other plant species.

Plants, or plant parts, comprising one or more mutant SlPP2C1 alleles and being drought tolerant may be field crops (e.g. rice, maize, soybean, wheat, barley, rye, sorghum, *Brassica*, etc.) or vegetable crops (e.g. tomato, cucumber, onion, carrot, cabbage, cauliflower, broccoli, watermelon, melon, lettuce, leek, spinach, radish, potato, artichoke, corn salad, pumpkin, squash, bean, peas, pepper).

Different in vivo expression of wild type SlPP2C1 alleles (or variants, including orthologs) may also lead to plants having significantly enhanced drought tolerance. For example wild type SlPP2C1 alleles comprising promoters having a different expression pattern, especially reduced expression, than the alleles found in cultivated tomato plants may be identified (e.g. in wild relatives of tomato) and introgressed (transferred through crossing) into cultivated tomato. Or alleles having mutations in the SlPP2C1 promoter may be identified or generated and used to generate plants having enhanced drought tolerance.

SEQUENCES

SEQ ID NO 1: cDNA sequence of the wild type SlPP2C1 allele from tomato
SEQ ID NO 2: protein sequence of the SlPP2C1 protein encoded by SEQ ID NO: 1
SEQ ID NO 3 and 4: primer 1 and 2 for amplifying SlPP2C1 cDNA (Q PCR)
SEQ ID NO 5 and 6: primer pair for amplifying actin cDNA
SEQ ID NO 7 and 8: primer pair for amplifying ubiquitin cDNA
SEQ ID NO 9 and 10: primer pair for amplifying full length SlPP2C1 cDNA
SEQ ID NO 11: genomic sequence of the wild type SlPP2C1 allele from tomato; transcription regulatory elements (e.g. promoter elements) are comprised in nucleotides 1-2675; protein encoding sequences (exons) consist of nucleotides 2676-3419 (exon 1), 4247-4351 (exon 2) and 4632-4975 (exon 3). The primary RNA is depicted in nucleotides 2591-5050.
SEQ ID NO 12 and 13: primers used to detect SlPP2C1 mutations in mutagenized tomato plants (see Example 4)
SEQ ID NO 14: putative potato SlPP2C1 cDNA (termed StPP2C1 herein)
SEQ ID NO 15: putative potato SlPP2C1 protein (termed StPP2C1 herein)

FIGURE LEGENDS

FIG. 1: A) Relative mRNA levels of SlPP2C1 in leaf (dark grey bars) of transgenic lines (T6$_{OE}$, T34$_{OE}$, T55$_{OF}$) are 25-fold higher as compared to wild type (Wt). B) Relative mRNA levels of SlPP2C1 in pollinated ovaries (light grey bars) in T55$_{OE}$ are similar to wild type, while the levels in T6$_{OE}$ and T34$_{OE}$ are lower as compared to wild type. C) Relative mRNA levels in transgenic lines T12$_{CS}$ and T35$_{CS}$ are lower in both leaves (dark grey bars) and unpollinated ovaries (light grey bars) as compared to wild type and T18. Mean values of biological replicas are shown with SE, wild type levels were set to one.

Figure 2:
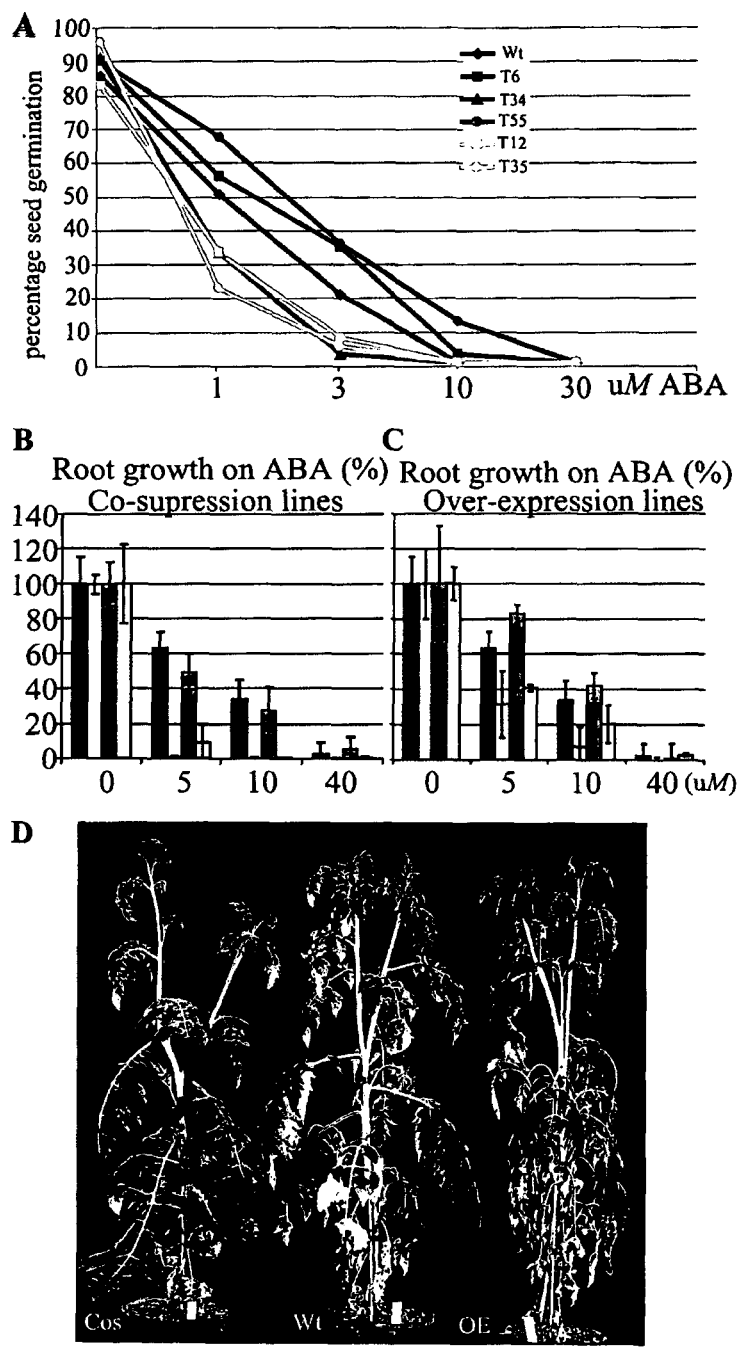

FIG. 2: A) Seed germination is inhibited less by ABA in the over-expression lines T6$_{OE}$ and T55$_{OE}$ and more in the co-suppression lines T12$_{CS}$ and T35$_{CS}$ as compared to wild type (Wt). Line T34$_{OE}$ behaves atypically. Dark grey lines represent over-expression lines, light grey lines represent co-suppression lines and black line represents wild type. B) Root growth is inhibited more by ABA in the co-suppression lines T12$_{CS}$ (white) and T35$_{CS}$ (light grey) as compared to T18 (dark grey) and wild type (black). C) Root growth is inhibited less by ABA in the over-expression line T34$_{OE}$ (dark grey), but more in T6$_{OE}$ (white) and T55$_{OE}$ (light grey), as compared to wild type (black). Mean root growth percentage is depicted with SD. D) Nine days after the start of water with-holding co-suppression lines are not wilted at all, while wild type shows moderate wilting and over-expression lines show severe wilting.

The following non-limiting Examples describe the use of SlPP2C1 genes for modifying plant phenotypes. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, and Sambrook and Russell (2001) *Molecular Cloning: A Laboratory Manual*, Third Edition, Cold Spring Harbor Laboratory Press, NY; and in Volumes 1 and 2 of Ausubel et al. (1994) *Current Protocols in Molecular Biology, Current Protocols*, USA. Standard mate-

EXAMPLES

Example 1

Isolation and Characterization of SlPP2C1

1.1 Materials and Methods 1.1.1 Plant Material

Tomato plants (*Solanum lycopersicum* L. cv. Moneymaker) were grown under greenhouse conditions from March to October under 16/8 h day-night rhythm. Supplementary lights (600 Watt high pressure sodium lights, Philips, Eindhoven, The Netherlands) turned on below 200 W/m$^2$ and turned off above 300 W/m$^2$. Temperature was kept above 20° C. during the light period and 17° C. during the dark period with the PRIVA Integro versie 724 system. Plants were watered daily and given fertilizer weekly. Leaf and ovary tissues were dissected form adult tomato plants and root and hypocotyls from 10-day-old seedlings. Tissues were harvested between 11.00 hrs and 13.00 hrs and directly frozen in liquid nitrogen.

1.1.2 SlPP2C1 Gene-Expression Analysis and Q-PCR cDNA-AFLP was preformed as described in Vriezen et al. (2008, New Phytologist, 177:60-76, see page 61 and 62), comparing pollinated ovaries with gibberellic acid (GA$_3$) treated ovaries. A differentially expressed fragment of 326 bp was cut out from the gel and the eluted DNA was re-amplified under the same conditions as used for the selective amplification. The fragment was ligated in a T-tailed EcoRV digested phagemid pBluescriptII SK(+) (Stratagene, La Jolla, Calif., USA) and sequenced using the CEQ DTCS Quick Start Kit and CEQ2000 DNA Analysis System (Beckman Coulter, Fullerton, Calif., USA).

For quantitative PCR analysis RNA was isolated with the Trizol (Invitrogen, Carlsbad, Calif., USA). Photometric RNA measurements were done to equilibrate the RNA concentrations of different samples. Equal amounts of RNA were DNAse treated with RNAse free DNAse (RQ1, Promega, Madison, USA). RNA (0.5 µg) was reverse transcribed (RT) using a cDNA synthesis kit (iScript™, Bio-rad Laboratories, Hercules, Calif., USA) following protocol.

Real-time-quantitative PCR (Q-PCR) primers for quantifying SlPP2C1 mRNA transcript levels were designed using a computer program (Beacon Designer Software, Premier Biosoft International, CA, USA), and checked for cross-homology with other PP2C sequences.

```
                                        (SEQ ID NO: 3)
    Primer 1: 5'-TCGGAAGGAGAAGATTACG-3'

(SEQ ID NO: 4)
    Primer 2: 5'-TCCACAATTCGCAACAAC-3'
```

Primer pair 1 and 2 amplifies the following fragment of the SlPP2C1 transcript (174 bp):

```
                                                   (SEQ ID NO: 22)
5'TCGGAAGGAGAAGATTACGATGGGAAGAGTATTAACTGGGAGAAAGTT
ATGACGGAGAGTTTCCGTAAAATGGACGAAAAGGTGAACAAGGAAGGGGC
GGAGATGGCGACGATAGGATCAACGGCGGTGGTAGCGGTGGTGGGAGTGG
AGGAATTTGTTGTTGCGAATTGTGGA 3'
```

PCR reactions were preformed in a 96-well thermocycler (Bio-Rad iCycler, Bio-rad laboratories) using SYBR green mix (iB-SYBR Green supermix, Bio-rad laboratories). The PCR program started with 3 minutes at 95° C. then 40 cycles consisting of 15 second at 95° C. and 45 seconds at 57° C. and finally the melting temperature of the amplified product was determined to verify the presence of a specific product. Five microliter of 25-fold diluted cDNA was used per sample. Technical and biological replicates were always preformed.

Both actin mRNA and ubiquitin were used as internal control genes.

```
                                        (SEQ ID NO: 5)
Actin primer 1: 5'-GGACTCTGGTGATGGTGTTAG-3'

(SEQ ID NO: 6)
Actin primer 2: 5'-CCGTTCAGCAGTAGTGGTG-3'

(SEQ ID NO: 7)
Ubiquitin primer 1: 5'-CCCTGGCTGATTACAACATTC-3'

(SEQ ID NO: 8)
Ubiquitin primer 2: 5'-TGGTGTCAGTGGGTTCAATG-3'
```

Diluted DNase treated RNA was also included in the Q-PCR as a control for genomic DNA contamination.

1.1.3 Plant Transformation

To generate transgenic SlPP2C1-lines, the coding region of SlPP2C1 (SEQ ID NO: 1) was PCR amplified and cloned in pDONR vector. PCR primers used for amplifying the complete SlPP2C1 cDNA were designed as follows:

```
    Primer 1 (forward):
                                        (SEQ ID NO: 9)
    5'CACCTGCAGTCACCGTCTTCACATTAAAAT 3'

Primer 2 (reverse):
                                        (SEQ ID NO: 10)
    5'ATTTGTATGGGAAGCTTAACTATCA 3'
```

Using Gateway cloning the SlPP2C1 was cloned behind the Cauliflower Mosaic Virus 35S promoter in the pAD625 vector (de Folter et al. 2006, The Plant Journal 47: 934-946) which also contains a nopaline synthase terminator (3' nos). Transgenic tomato plants were generated by *Agrobacterium tumefaciens*-mediated transformation and tissue culture as described in De Jong et al. (2008, supra).

1.1.4 Water Stress Experiment

The pots of wild type and SlPP2C1 transgenic lines of the same age and size, were saturated with water at the start of the experiment. Several plants were used per line. Plants were withheld from water for ten days. Wilting of leaves was assessed visually when the first signs of wilting (slight wilting or moderate wilting) was seen in the wild type control at day 8 and 9, respectively. A scale of 1-4 was used, with 4 being severely wilted, 3 being moderately wilted, 2 being slightly wilted and 1 showing no signs of leaf wilting.

Photographs depicted in FIG. 2D were taken nine days after start of the experiment.

1.1.5 Seed Germination Assay and Root Growth Assay

Seed Germination:

Seeds of the transgenic lines were harvested, dried and stored at 4 degrees Celsius. Seeds were sterilized in diluted bleach (4% (w/v) hypochlorite) containing 0.1% (v/v) Tween-20, washed and sown on ½MS media (2.25 mg MS basal salts supplied with 1% (w/v) sucrose, and Nitsch vitamins, Duchefa, Haarlem, the Netherlands) containing, 0, 1, 3, 10, or 30 WI ABA (Acros, Geel, Belgium). At least 40 seeds per ABA concentration were used.

The plates were placed in a growth chamber at 25° C. under 16/8 h day-night rhythm. Seed germination (radicle protrusion) was scored after ten days and seed germination percentages were calculated.

Root Growth:

Seeds were sterilized as described above and sown in water containing 1 µl $GA_3$. After radicle protrusion ten seeds of each line were placed on ½MS media containing either 0, 5, 10, or 40 µM ABA. The roots were measured and the plates were placed in vertical position and grown under conditions described above. Seven days after transfer the length of the root was measured again and root growth was calculated as a percentage of root growth compared to ½MS media without ABA (100%). Experiments were carried out three times and mean values plus SD are shown. Student's t-tests were performed to test for significance (p<0.05).

1.2. Results 1.2.1 Expression of SlPP2C1 During Fruit Set (Data not Shown)

The SlPP2C1 gene is differentially expressed during fruit set (Vriezen et al. 2008, supra). SlPP2C1 is expressed highest in the pericarp of unpollinated ovaries and lower after pollination and $GA_3$-treatment. The expression in ovules/placenta does not seem to change. We confirmed the expression of SlPP2C1 within the tissues of the tomato ovary by quantitative PCR. Again it was observed that the mRNA levels of SlPP2C1 are higher in the pericarp than in the ovules or placenta in control tissue. In the pericarp, but also in the placenta, a lower mRNA level of SlPP2C1 was found three days after pollination. In ovules mRNA levels did not change. The SlPP2C1 gene is expressed in mature unpollinated ovaries at anthesis at a relatively high level compared to vegetative tissues such as leaf, root and hypocotyl. In flower buds and in ovaries three days before anthesis the SlPP2C1 mRNA level is comparable to leaf, and it is much lower than in ovaries at anthesis (control, Ct). Three days after pollination SlPP2C1 mRNA levels in the ovary were reduced to approximately 50% of the level in unpollinated ones.

1.2.2 Functional Analysis of SlPP2C1

Overexpression of SlPP2C1

The over-expression (OE) approach resulted in three transgenic tomato lines with on average 25-fold higher mRNA levels of SlPP2C1 in leaves (overexpressing lines $T6_{OE}$, $T34_{OE}$ and $T55_{OE}$, FIG. 1A). In pollinated ovaries the SlPP2C1 mRNA levels of these lines were not higher as in wild type (FIG. 1B). On the contrary, $T6_{OE}$ and $T34_{OE}$ displayed a strong reduction in SlPP2C1 mRNA levels as compared to wild type. $T55_{OE}$ had mRNA levels similar to wild type in pollinated ovaries. The SlPP2C1 mRNA levels in unpollinated ovaries of these transgenic lines were comparable to the mRNA levels in pollinated ovaries and are not depicted here.

Silencing of SlPP2C1

Additionally, two lines (co-suppression lines $T12_{CS}$ and $T35_{CS}$) were obtained that had lower SlPP2C1 mRNA levels in leaves and unpollinated ovaries, as compared to wild type (FIG. 1C), indicating that the overexpression construct led to co-suppression of SlPP2C1 in these lines. Line T18 has mRNA levels that are comparable to wild type in both tissues.

Sensitivity to ABA

Phenotypic characterization of the transgenic lines revealed changed sensitivity for ABA. FIG. 2A shows the percentage of seed germination on media containing different concentrations of ABA. The co-suppression lines $T12_{CS}$ and $T35_{CS}$ have lower germination percentages on 1 µM and 3 µM ABA, while the overexpressing lines $T6_{OE}$ and $T55_{OE}$ have slightly higher germination percentages than wild type. Line $T34_{OE}$, which is an over-expression line in leaves, behaved differently from the other over-expression lines and showed lower seed germination on ABA as compared to wild type.

Root growth after germination is reduced by ABA in wild type. In FIG. 2B it can be seen that root growth in co-suppression lines $T12_{CS}$ and $T35_{CS}$ was inhibited more strongly than in wild type or T18. Overexpression line $T34_{OE}$ was less sensitive to root growth inhibition by ABA than wild type (FIG. 2C). Root growth of lines $T6_{OE}$ and $T55_{OE}$ was more sensitive to ABA.

Thus, co-suppression of SlPP2C1 leads to plants having a significantly enhanced ABA sensitivity than wild type (seed germination is inhibited more and root growth is inhibited more than in wild type), while overexpression leads to plants having a reduced ABA sensitivity, indicating that SlPP2C1 encodes a negative regulator of ABA.

Drought Tolerance

FIG. 2 D shows that at 9 days wild type plants having moderate wilting, co-suppressing lines showing no wilting and over expressing lines showing severe wilting. At 9 days, the over-expressing lines were severely wilted (average wilting score=3.6), while co-suppressing lines showed little wilting (score 1.25) and controls showed moderate wilting (score=3.0). The experiment was repeated once (data not shown). Thus, wilting was reduced in the co-suppressing lines by 58% compared to wild type control.

These data indicate that down-regulation of SlPP2C1 leads to plants having significantly enhanced drought tolerance compared to wild type.

Discussion

Two of the transgenic lines harbouring an over-expression construct had lower levels of SlPP2C1 mRNA in both leaves and ovaries. RNA silencing by co-suppression is a well accepted phenomenon although the mechanism is not fully understood. It has been suggested that co-suppression is induced by hairpin-RNA transcripts from inverted-repeat transgene copies, resulting in siRNAs that are incorporated into the RNAi pathway (Tomita et al. 2004, FEBS Lett. 2004 Aug. 27; 573(1-3):117-20; Wang and Metzlaff 2005, Curr Opin Plant Biol. 8(2): 216-22). Southern blot analysis (data not shown) revealed that in the two co-suppression lines of SlPP2C1 multiple insertions were present, which might have resulted in a hairpin-like structure that could silence the endogenous SlPP2C1 gene.

The three lines with a 25-fold higher mRNA level of SlPP2C1 in leaf did not have higher SlPP2C mRNA levels in ovaries. This might be partly explained by the relatively high mRNA level of the endogenous gene in ovaries, which is seven fold higher than in leaf. The contribution of the transgene to the total expression levels of SlPP2C1 in ovaries might therefore have been very small. Remarkable is that in line $T6_{OE}$ and $T34_{OE}$ the mRNA level of SlPP2C1 in ovary is even lower (10-50%) than in wild type. Tissue specific control of endogenous mRNA levels by a transgene has however been reported before. Tomita et al. (2004, supra) showed that in the same plant the NtFAD3 gene was co-suppressed in leaf but over-expressed in root, resulting in the equivalent phenotypes in leaves and roots. The mechanisms by which tissue specific regulation of co-suppression occurs are unknown, but the level of endogenous transcript seems to be important (Tomita et al. 2004, supra).

The two tomato transgenic lines with reduced mRNA levels in leaf and ovary also displayed ABA-hypersensitive responses during seed germination and root growth and enhanced tolerance to water stress. This indicates that the SlPP2C1 gene is a negative regulator of the ABA signalling cascade in tomato. Moreover, the three transgenic lines with relative high mRNA levels of SlPP2C1 in leaf also wilted stronger.

Example 2

TILLING Mutants Comprising Enhanced Drought Tolerance and Comprising Mutant SlPP2C1 Alleles 2.1 Tomato TILLING Population A highly homozygous inbred line used in commercial processing tomato breeding was used for mutagenesis treatment with the following protocol. After seed germination on damp Whatman® paper for 24 h, ~20,000 seeds, divided in 8 batches of 2500 respectively, were soaked in 100 ml of ultra pure water and ethyl methanesulfonate (EMS) at a concentration of 1% in conical flasks. The flasks were gently shaken for 16 h at room temperature. Finally, EMS was rinsed out under flowing water. Following EMS treatment, seeds were directly sown in the greenhouse. Out of the 60% of the seeds that germinated, 10600 plantlets were transplanted in the field. From the 8810 M1 lines that gave fruits, two fruits per plant were harvested. DNA was isolated from seeds coming from the first fruit, constituting the M2 population DNA stock. These were selfed and M3 seeds were isolated from the fruits and the seeds were used for DNA isolation and constitute the M3 population DNA bank.

2.2 Target SlPP2C1 Gene for PCR Amplification from TILLING Population

Genomic sequence containing the complete transcribed region including coding region (COD), untranslated 5' end region (5' UTR) and 3' end region (3' UTR) was determined using PCR with genomic tomato DNA as template and primers designed on the flanks of the tomato SlPP2C1 sequence. By comparison of the genomic gene sequence with the SlPP2C1 cDNA sequence the location, number and size of introns and exons in this gene was determined.

The genomic sequence is depicted in SEQ ID NO: 11. The primary RNA (transcribed region) is from nucleotide 2591-5050, comprising a 5' UTR (2591-2675), exon 1 (2676-3419), intron 1 (3420-4246), exon 2 (4247-4351), intron 2 (4352-4631), exon 3 (4632-4975) and the 3' UTR (4976-5050).

DNA of the tomato TILLING population described above was then screened for single nucleotide polymorphisms in the SlPP2C1 target gene. For this purpose PCR primer pairs were designed to amplify overlapping fragments of about 400-500 bp from the coding (exon) sequences of the SlPP2C1 gene (SEQ ID NO: 1) or a sequence comprising all or part of the nucleic acid which encodes the C-terminus of the SlPP2C1 protein (as mutations in the catalytic domain are likely to result in reduced function or loss of function of the protein), i.e. encoding amino acids 84-391 of SEQ ID NO: 2. See Example 4 below, where mutations in amino acids 101-192 were identified.

The primer pairs were used to amplify target sequences from the M2 or M3 DNA of the TILLING population and heteroduplexes between mutant and wild type target sequences were detected using CSCE or HRM as described below. The ID number of the DNA samples is linked to seed batches of plants carrying the wild type allele or the mutated allele either in heterozygous or in homozygous form.

Seeds were germinated and the presence of the particular mutation in individual plants was confirmed by PCR using primers flanking the mutated site and genomic DNA of these plants as templates. DNA sequencing of the fragments identified mutants homozygous and heterozygous for the expected mutation. Homozygous mutants are selected or obtained after selfing and subsequent selection and the effect of the mutation on the corresponding protein and phenotype of the plant is determined.

Plants comprising one or more mutations in the target sequences are screened phenotypically for drought tolerance using e.g. the assay described above and/or field assessment.

2.3 Conformation Sensitive Capillary Electrophoresis (CSCE)

Multiplex PCR reactions are performed in 10 µl volume with 0.15 ng, 4 times pooled genomic DNA. Labeled primers are added to the PCR master mix to a concentration 5 times lower (1 µM) than that of the unlabeled primers. Post PCR, samples are diluted 10 times. Before the CSCE run, 2 µl of the diluted products are added to 38 µl of MQ water.

The samples are loaded on 50 cm capillaries (injection time and voltage: 16 seconds, 10 KVolts; Run voltage: 15 KVolts) from the ABI 3130xl apparatus filled with semi-denaturating polymers of the following composition: 5 g Conformation Analysis Polymer (CAP) (Applied Biosystems, 434037, 9%), 2.16 g Ureum, 0.45 g 20×TTE (national diagnostics, EC-871), completed with MQ water up to 9 g. The running buffer is prepared with 1× diluted TTE and 10% glycerol. The oven temperature is set to 18° C.)

Raw data is analysed with the HeteroDuplex Analysis (HDA) software from BioNumerics, The program differentiates peak patterns of hetero-duplexes (mutant) and homoduplex molecules (wild type) thus providing the possibility of selecting DNA-pools containing an individual line mutated in the target gene.

2.4 High Resolution Melt Curve Analysis (HRM)

The LCgreen PCRs are performed on 8× flat pools in FramStar 96-wells plates (4titude, UK). 2 µl (15 ng) of pooled DNA is mixed with 2 µl of F-524 Phire™ 5× reaction buffer (FINNZYMES, Finland), 0.1 µl Phire™ Hot Start DNA Polymerase (FINNZYMES, Finland), 1 µl LCGreen™ Plus+ (BioChem, USA), 0.25 µl of 5 mM primers, and completed to 10 µl with MQ water) according to manufacturer recommendations. Pools containing a mutation are screened using a LightScanner® System (Idaho Technology Inc., USA). Positive pools are selected by analyzing the melting temperature profiles; when the pool contains a mutation it will show a lower melting temperature.

Example 3

Transfer of Mutant SlPP2C1 Alleles into Tomato Cultivars

TILLING mutants comprising a mutant SlPP2C1 allele are crossed with different tomato lines in order to transfer the mutant allele into these lines, generating tomato plants with good agronomic characteristics and significantly enhanced drought tolerance.

A TaqMan® SNP Genotyping Assays (Applied Biosystems) marker is developed to identify the presence of the modified nucleotide. This assay is used for Marker-assisted foreground selection which is effective for the transfer of recessive genes to a required background, for example commercial tomato parent lines, since their classical transfer requires additional recurrent selfing generations (Ribaut et al. Plant Molecular Biology Reporter 15:154-162).

Example 4

DNA of the M2 TILLING population described in Example 2.1 was screened for single nucleotide polymorphisms in the SlPP2C1 target gene (as described in 2.2), in particular for mutations in the sequence encoding amino acids 101 to 192.

For this purpose the following PCR primer pair was designed to amplify a 277 bp fragment of nucleotides 301-577 of SEQ ID NO: 1:

```
Foward primer: "3863"
                              (SEQ ID NO: 12)
5'-GTGACGTGCTGTTCACATGGATC-3'

Reverse primer: "3861"
                              (SEQ ID NO: 13)
5'-TACGGAAACTCTCCGTCATAAC-3'
```

The primer pair was used to amplify target sequences from the M2 DNA of the Tilling population. The amplified target sequence comprises nucleotide 301 to 577 of SEQ ID NO: 1, i.e. the region encoding amino acids 101 to 192 of SEQ ID NO: 2. Heteroduplexes between mutant and wild type target sequence were identified using HRM as described in Example 2.3 (or 2.4).

Ten plants comprising a SNP in the target region were identified and the PCR product of the target sequence was sequenced in order to determine the nature and position of the SNP. The results are shown in Table 2 below.

TABLE 2

| Plant number (M2, heterozygous) | SNP in target sequence | Mutation effect on protein sequence (SEQ ID NO: 2) | SIFT prediction on protein function |
|---|---|---|---|
| 1 | T → A at nucleotide 372 of SEQ ID NO: 1 (atT → atA) | Ile 124 → Ile | silent |
| 2 | G → A at nucleotide 442 of SEQ ID NO: 1 (Ggg → Agg) | Gly 148 → Arg | deleterious |
| 3 | C → T at nucleotide 512 of SEQ ID NO: 1 (tCg → tTg) | Ser 171 → Leu | tolerated |
| 4 | G → A at nucleotide 504 of SEQ ID NO: 1 (caG → caA) | Gln 168 → Gln 168 | silent |
| 5 | G → A at nucleotide 463 of SEQ ID NO: 1 (Gcg → Acg) | Ala 155 → Thr | deleterious |
| 6 | G → A at nucleotide 465 of SEQ ID NO: 1 (gcG → gcA) | Ala 155 → Ala | silent |
| 7 | G → A at nucleotide 394 of SEQ ID NO: 1 (Ggc → Agc) | Gly 132 → Ser | tolerated |
| 8 | To be determined | To be determined | To be determined |
| 9 | To be determined | To be determined | To be determined |

TABLE 2-continued

| Plant number (M2, heterozygous) | SNP in target sequence | Mutation effect on protein sequence (SEQ ID NO: 2) | SIFT prediction on protein function |
|---|---|---|---|
| 10 | G → A at nucleotide 463 of SEQ ID NO: 1 (Gcg → Acg) | Ala 155 → Thr | deleterious |

Based on SIFT analysis (Pauline C. Ng and Henikoff 2003, Nucleic Acid Research Vol. 31, pp 3812-3814) the effect on protein function was predicted, see Table 2.

Three plants (plants number 1, 4 and 6) contained a silent mutation in the SlPP2C1 gene, while five plants (number 2, 3, 5, 7 and 10) contained SNPs that lead to amino acid substitutions. Plants 5 and 10 contained identical mutations. Based on SIFT analysis, it is predicted that plants number 2, 5 and 10 comprise mutations in the SlPP2C1 allele which reduce or abolish PP2C1 protein function and therefore confer enhanced drought tolerance. It is noted that the mutant SlPP2C1 allele found in plant 2 is in the Asp-Gly-His (DGH) domain.

Plants number 3 and 7 may also comprise a mutant allele which may confer enhanced drought tolerance.

To test the response of plants 2, 3, 5, 7 and 10 to drought and/or other abiotic stresses, 14-d-old seedlings are subjected to various forms of stress treatments selected from one or more of the following treatments.

1. Drought stress can be imposed as described in the general description, the Examples above and/or by growing seedlings for 21 days in vitro on MS (to obtain homogenous populations) after which they are transferred to pots containing sandy soil. Two weeks after transfer water is withheld for 6 days after which 50 ml water/plant is added once. Results are scored when the azygous and control plants turn yellow (modified from The Plant Journal, 2004, 41, 95-106).
2. Salinity stress is imposed by growing seedlings on MS medium containing 250 mM NaCl for 0 to 48 h.
3. Osmotic stress can be imposed by growing seedlings on MS medium with added mannitol at 75 mM or ABA at 0.1 or 1.0 mM. Total root length and the amount of lateral roots developing during plant growth is a measure for osmotic stress tolerance and ABA sensitivity, respectively (modified from Xion et al., Plant Physiology, 2006, 142, 1065-1074).

DEPOSIT FORMATION

A representative sample of seeds of the *Solanum lycopersicum* plant number 2 (as referred to in Table 2) (Gly148Arg mutant) comprising a substitution of the glycine at amino acid position 148 into arginine, was deposited by Nunhems B. V. and accepted for deposit on Jun. 23, 2016 at the NCIMB Ltd. (Ferguson Building, Craibstone Estate, Bucksburn Aberdeen, Scotland AB21 9YA. UK) according to the Budapest Treaty, under the Expert Solution (EPC 2000, Rule 32(1)). The seed of the Gly148Arg mutant was given the following deposit number: NCIMB 42602.

A representative sample of seeds of the *Solanum lycoperiscum* plant number 5 (as referred to in Table 2) (Ala155Thr mutant) comprising a substitution of the alanine at amino acid position 155 into threonine, was deposited by Nunhems B.V. and accepted for deposit on Jun. 23, 2016 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). The seed of the Ala155Thr mutant was given the following deposit number NCIMB 42604.

A representative sample of seed of the *Solanum lycopersicum* plant number 7 (as referred to in Table 2) (Gly132Ser mutant) comprising a substitution of the glycine at amino acid position 132 into serine, was deposited by Nunhems B.V. and accepted for deposit on Jun. 23, 2016 at the NCIMB Ltd. (Ferguson Building, Craibstone Estate Bucksburn Aberdeen, Scotland AB21 9YA, UK) according to the Budapest Treaty. under the Expert Solution (EPC 2000, Rule 32(1)). The seed of the Gly132Ser mutant was given the following deposit number: NCIMB 42603.

Access to the deposits will be available during the pendency of this application to persons determined by the Director of the Patent and Trademark Office to be entitled thereto upon request. Applicant requests that samples of the seeds and any material derived from said samples, be only released to a designated Expert in accordance with Rule 32(1) EPC or related legislation of countries or treaties having similar rules and regulation. Subject to 37 C.F.R. §1.808(b), all restrictions imposed by the depositor on the availability to the public of one or more deposits will be irrevocably removed upon the granting of the patent. The deposit will be maintained for a period of 30 years. or 5 years after the most recent request, or for the enforceable life of the patent whichever is longer, and will be replaced if it ever becomes nonviable during that period. Applicant does not waive any rights granted under this patent on this application or under the Plant Variety Protection Act (7 U.S.C. 2321 et seq.).

Plants comprising significantly enhanced stress tolerance, especially drought tolerance, compared to controls are used to generate tomato cultivars with good agronomic characteristics as e.g. described in Example 3. Plants with significantly enhanced drought tolerance may also in addition or alternatively comprise significantly enhanced salinity and/or osmotic stress tolerance compared to controls.

The invention claimed is:

1. A non-transgenic *Solanum lycopersicum* F1 hybrid plant homozygous for a mutant SlPP2C1 allele in its genome, wherein said mutant allele encodes a polypeptide having one or more of the mutations selected from the group consisting of Gly148Arg, Ala155Thr, and Gly132Ser relative to the wild type polypeptide set forth in SEQ ID NO: 2, wherein said plant has enhanced drought tolerance as compared to a *Solanum lycopersicum* plant comprising the wild type SlPP2C1 allele.

2. A *Solanum lycopersicum* seed having a mutant SlPP2C1 allele in its genome, representative samples of said seed having been deposited under NCIMB Accession Numbers 42602, 42603, or 42604.

3. A fruit, seed, or a plant part of the F1 hybrid plant according to claim 1, wherein said fruit, seed, or plant part comprises said mutant SlPP2C1 allele.

4. The F1 hybrid plant of claim 1, wherein said SlPP2C1 allele encodes a protein comprising the amino acid substitution at position Ala155 as compared to SEQ ID NO: 2.

5. The F1 hybrid plant of claim 1, wherein said SlPP2C1 allele encodes a protein comprising the amino acid substitution at position Gly148 as compared to SEQ ID NO: 2.

6. The F1 hybrid plant of claim 1, wherein said SlPP2C1 allele encodes a protein comprising the amino acid substitution at position Gly132 as compared to SEQ ID NO: 2.

7. The F1 hybrid plant of claim 1, wherein the mutant SlPP2C1 allele is obtainable by TILLING.

8. An inbred tomato plant homozygous for a mutant SlPP2C1 allele in its genome, wherein said mutant allele encodes a SlPP2C1 polypeptide having one or more of the mutations selected from the group consisting of Gly148Arg, Ala155Thr, and Gly132Ser relative to the wild type polypeptide set forth in SEQ ID NO: 2.

9. A method of generating non-transgenic *Solanum lycopersicum* plants with enhanced drought tolerance comprising inducing one or more mutations in the wild-type SlPP2C1 allele of SEQ ID NO: 2 to produce a mutant SlPP2C1 allele, wherein said mutant SlPP2C1 allele encodes a polypeptide having one or more mutations selected from the group consisting of Gly148Arg, Ala155Thr, and Gly132Ser relative to the wild type polypeptide set forth in SEQ ID NO: 2.

10. The method of claim 9, wherein representative samples of seeds of said plant having enhanced drought tolerance and comprising said mutant SlPP2C1 allele having been deposited under NCIMB Accession Numbers 42602, 42603, or 42604.

11. The method of claim 9, wherein said SlPP2C1 allele encodes a protein comprising the amino acid substitution at position Ala155 as compared to SEQ ID NO: 2.

12. The method of claim 9, wherein said SlPP2C1 allele encodes a protein comprising the amino acid substitution at position Gly148 as compared to SEQ ID NO: 2.

13. The method of claim 9, wherein said SlPP2C1 allele encodes a protein comprising the amino acid substitution at position Gly132 as compared to SEQ ID NO: 2.

14. The method of claim 9 further comprising selecting a *Solanum lycopersicum* plant for enhanced drought tolerance as compared to a *Solanum lycopersicum* plant comprising the wild type SlPP2C1 allele.

15. The method of claim 9, further comprising crossing said *Solanum lycopersicum* plant having enhanced drought tolerance with itself or a second plant.

16. The method of claim 14 further comprising crossing said *Solanum lycopersicum* plant selected for enhanced drought tolerance with itself or a second plant.

17. The method of claim 16, wherein the crossing comprises crossing the *Solanum lycopersicum* plant comprising the mutant SlPP2C1 allele selected for enhanced drought tolerance with another *Solanum lycopersicum* plant.

18. The method of claim 16, wherein the crossing comprises crossing the *Solanum lycopersicum* plant comprising the mutant SlPP2C1 allele with itself.

19. A *Solanum lycopersicum* plant grown from the seed of claim 2.

20. An F1 hybrid seed produced by crossing the plant of claim 19 with a second plant, wherein said F1 hybrid seed comprises the mutant SlPP2C1 allele.

* * * * *